United States Patent
Breitfelder et al.

(10) Patent No.: US 7,517,995 B2
(45) Date of Patent: *Apr. 14, 2009

(54) THIAZOLYL-DIHYDRO-CYCLOPENTAPYRAZOLE

(75) Inventors: Steffen Breitfelder, Assmannshardt (DE); Udo Maier, Senden (DE); Christoph Hoenke, Ingelheim (DE); Anne T. Joergensen, Biberach (DE); Alexander Pautsch, Ulm (DE); Trixi Brandl, Basel (CH); Matthias Grauert, Biberach (DE); Matthias Hoffmann, Mittelbiberach (DE); Stefan Scheuerer, Warthausen (DE); Klaus Erb, Mittelbiberach (DE); Michael Pieper, Biberach (DE); Ingo Pragst, Munich (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/690,356

(22) Filed: Mar. 23, 2007

(65) Prior Publication Data

US 2007/0238730 A1 Oct. 11, 2007

(30) Foreign Application Priority Data

Apr. 6, 2006 (EP) .................................. 06112298

(51) Int. Cl.
*A61K 31/429* (2006.01)
*C07D 513/04* (2006.01)
(52) U.S. Cl. ........................................ 548/151; 514/366
(58) Field of Classification Search .................. 548/151
See application file for complete search history.

(56) References Cited

U.S. PATENT DOCUMENTS

| 2002/0151544 A1 | 10/2002 | Hayakawa et al. |
| 2006/0100254 A1 | 5/2006 | Betzemeier et al. |
| 2006/0106013 A1 | 5/2006 | Breitfelder et al. |

FOREIGN PATENT DOCUMENTS

| CA | 2539767 A1 | 4/2005 |
| CA | 2579279 A1 * | 4/2006 |
| CA | 2579288 A1 | 4/2006 |
| DE | 10344223 A1 | 4/2005 |
| WO | WO 01/57008 A1 | 8/2001 |
| WO | WO 03/072557 A1 | 9/2003 |
| WO | WO 2004/007491 A1 | 1/2004 |
| WO | WO 2004/029055 A1 | 4/2004 |
| WO | WO 2004/052373 A1 | 6/2004 |
| WO | WO 2004/056820 A1 | 7/2004 |
| WO | WO 2005/005438 A1 | 1/2005 |
| WO | WO 2005/016245 A2 | 2/2005 |
| WO | 2004040281 A1 | 4/2006 |
| WO | WO 2006/040279 A1 | 4/2006 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
G. Y. Oudit, et al., "Phosphoinositide 3-Kinase γ-Deficient Mice are Protected from Isoproterenol-Induced Heart Failure", Circulation, 2003, vol. 108, No. 17, p. 2147-2152.
B. Vanhaesebroeck, et al., "Synthesis and Function of 3-Phosphorylated Inositol Lipids", Annual Review of Biochemistry, 2001, vol. 70, p. 535-602.
S. Ward, et al., "Isoform-specific phosphoinositide 3-kinase inhibitors as therapeutic agents", Current Opinion in Pharmacology, 2003, vol. 3, p. 426-434.

* cited by examiner

*Primary Examiner*—Laura L. Stockton
(74) *Attorney, Agent, or Firm*—Michael P. Morris; Mary-Ellen M. Devlin; Anthony P. Bottino

(57) ABSTRACT

Disclosed are compounds of general formula (I),

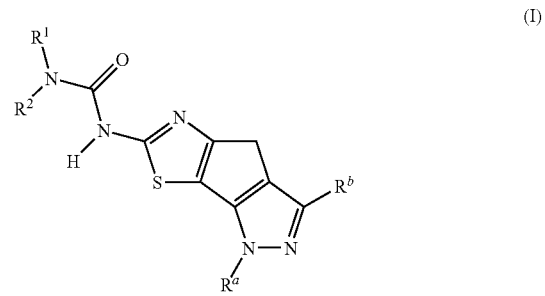

wherein the groups $R^1$, $R^2$, $R^a$ and $R^b$ have the meanings given in the claims and specification, the tautomers, racemates, enantiomers, diastereomers and the mixtures thereof, and optionally the pharmacologically acceptable acid addition salts, solvates and hydrates thereof, and processes for preparing these thiazolyl-dihydro-cyclopentapyrazoles and the use thereof as pharmaceutical compositions.

11 Claims, No Drawings

THIAZOLYL-DIHYDRO-CYCLOPENTAPYRAZOLE

This application claims priority benefit to EP 06112298, filed Apr. 6, 2006, which is encorporated herein in its entirety.

The present invention relates to new thiazolyl-dihydro-cyclopentapyrazoles of general formula (I)

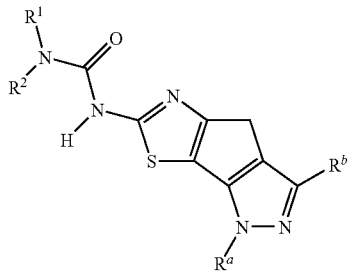

(I)

wherein the groups $R^1$, $R^2$, $R^a$ and $R^b$ have the meanings given in the claims and specification, the tautomers, racemates, enantiomers, diastereomers and the mixtures thereof, and optionally the pharmacologically acceptable acid addition salts, solvates and hydrates thereof, and processes for preparing these thiazolyl-dihydro-cyclopentapyrazoles and the use thereof as pharmaceutical compositions.

BACKGROUND TO THE INVENTION

Phosphatidylinositol-3-kinases (PI3-kinases) are a sub-family of the lipid kinases which catalyse the transfer of a phosphate group to the 3'-position of the inositol ring of phosphoinositides.

They have a role in numerous cell processes such as e.g. cell growth and differentiation processes, the control of cytoskeletal changes and the regulation of intracellular transport processes (Vanhaesebroeck et al., Annu Rev Biochem. 2001; 70:535-602).

PI3-kinases may play a part in numerous tumours, such as e.g. breast cancer, ovarian or pancreatic carcinoma, in tumour types such as carcinomas of the colon, breast or lungs, but particularly in autoimmune diseases such as Crohn's disease or rheumatoid arthritis, for example, or in the cardiovascular system, e.g. in the development of cardiac hypertrophy (Oudit et al., Circulation. 2003 Oct. 28; 108(17):2147-52). PI3-kinase modulators may represent a possible method of anti-inflammatory therapy with comparatively minor side effects (Ward and Finan, Curr Opin Pharmacol. 2003 August; 3(4): 426-34).

PI3-kinase inhibitors for treating inflammatory diseases are known in the literature. Thus, WO 03/072557 discloses 5-phenylthiazole derivatives, WO 04/029055 discloses annelated azolpyrimidines and WO 04/007491 discloses azolidi-none-vinyl linked benzene derivatives. Moreover, the two specifications WO 04/052373 and WO 04/056820 disclose benzoxazine and benzoxazin-3-one derivatives.

The aim of the present invention is to provide new compounds which by virtue of their pharmaceutical activity as PI3-kinase modulators may be used therapeutically for the treatment of inflammatory or allergic diseases. Examples of these include inflammatory and allergic respiratory complaints, inflammatory and allergic skin complaints, inflammatory eye diseases, diseases of the nasal mucosa, inflammatory or allergic illnesses which involve autoimmune reactions or kidney inflammation.

DETAILED DESCRIPTION OF THE INVENTION

Surprisingly it has been found that the above problem is solved by means of compounds of formula (I), wherein A and the groups $R^1$, $R^2$, $R^a$ and $R^b$ have the meanings given hereinafter.

It has been found, in particular, that compounds of formula (I) act as inhibitors of PI3-kinase, particularly as inhibitors of PI3-kinase gamma. Thus the compounds according to the invention may be used for example for the treatment of respiratory complaints.

The present invention therefore relates to compounds of general formula (I),

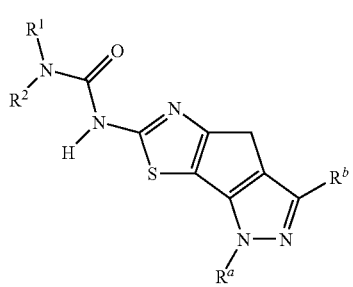

(I)

wherein $R^a$ denotes hydrogen or an optionally substituted group selected from among $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, $C_9$-$C_{13}$-spiro, $C_3$-$C_8$-heterocycloalkyl and $C_3$-$C_8$-heterocycloalkyl-$C_1$-$C_4$-alkyl, $R^b$ denotes hydrogen, $NH_2$ or $OH$, or an optionally substituted group selected from among $C_1$-$C_8$-alkyl, $C_3$-$C_8$-cycloalkyl, $C_2$-$C_8$-alkenyl, $C_2$-$C_8$-alkynyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, $C_9$-$C_{13}$-spiro, $C_3$-$C_8$-heterocycloalkyl, $CONH_2$, $C_6$-$C_{14}$-aryl-NH, $C_3$-$C_8$-heterocycloalkyl-NH— and OMe, $R^1$ denotes hydrogen or an optionally substituted group selected from among $C_1$-$C_8$-alkyl, $C_3$-$C_8$-cycloalkyl, $C_2$-$C_8$-alkenyl, $C_2$-$C_8$-alkynyl and $C_6$-$C_{14}$-aryl-$C_1$-$C_5$-alkyl, $R^2$ denotes hydrogen or an optionally substituted group selected from among $C_1$-$C_8$ alkyl, $C_3$-$C_8$-cycloalkyl, $C_2$-$C_8$-alkenyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_6$-alkyl, $C_9$-$C_{13}$-spiro, $C_3$-$C_8$-heterocycloalkyl, $C_3$-$C_8$-heterocycloalkyl-$C_1$-$C_6$-alkyl- and $C_6$-$C_{14}$-aryl-$C_1$-$C_6$-alkyl, or $R^1$ and $R^2$ together form an optionally substituted five-, six- or seven-membered ring consisting of carbon atoms and optionally 1 to 2 heteroatoms, selected from among oxygen, sulphur and nitrogen, or $R^1$ and $R^2$ together form an optionally substituted nine- to thirteen-membered spirocyclic ring, or $R^2$ denotes a group selected from among general formulae (A1) to (A18)

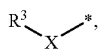
(A1)

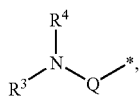
(A2)

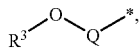
(A3)

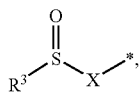
(A4)

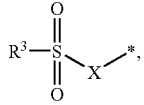
(A5)

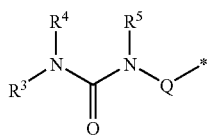
(A6)

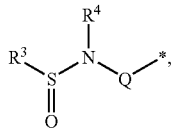
(A7)

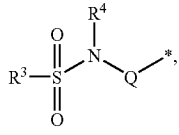
(A8)

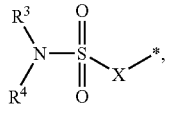
(A9)

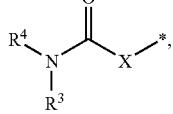
(A10)

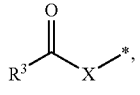
(A11)

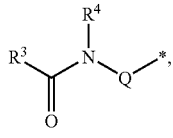
(A12)

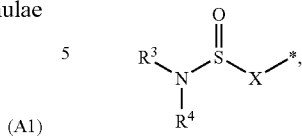
(A13)

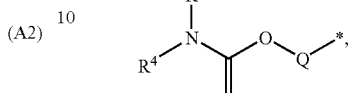
(A14)

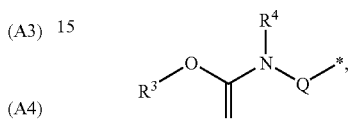
(A15)

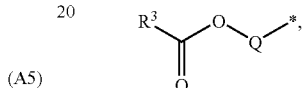
(A16)

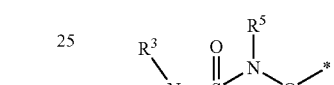
(A17) and

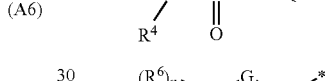
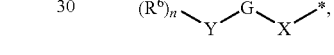
(A18)

wherein

X and Y may be linked to the same or different atoms of G, and

X denotes a bond or an optionally substituted group selected from among $C_1$-$C_7$-alkylene, $C_3$-$C_7$-alkenylene and $C_3$-$C_7$-alkynylene, or X together with $R^1$, $R^3$ or $R^4$ may form a $C_1$-$C_7$-alkylene bridge;

Y denotes a bond or optionally substituted $C_1$-$C_4$-alkylene;

Q denotes an optionally substituted group selected from among $C_1$-$C_7$-alkylene, $C_3$-$C_7$-alkenylene and $C_3$-$C_7$-alkynylene, Q together with $R^1$, $R^3$ or $R^4$ may form a $C_1$-$C_7$-alkylene bridge;

$R^3$, $R^4$, $R^5$ which may be identical or different, denote hydrogen or an optionally substituted group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_4$-alkyl, $NR^7R^8$, $NR^7R^8$—$C_1$-$C_4$-alkyl, $C_1$-$C_4$-alkoxy, $C_1$-$C_4$-alkoxy-$C_1$-$C_4$-alkyl, $C_6$-$C_{14}$-aryl and $C_5$-$C_{10}$-heteroaryl, or in each case two of the substituents $R^3$, $R^4$, $R^5$ together form an optionally substituted five-, six- or seven-membered ring, consisting of carbon atoms and optionally 1-2 heteroatoms, selected from among oxygen, sulphur and nitrogen;

G denotes a saturated, partially saturated or unsaturated ring system consisting of 3-10 C atoms, wherein optionally up to 6 C atoms are replaced by heteroatoms selected from among nitrogen, oxygen and sulphur;

$R^6$ which may be identical or different, denote hydrogen or an optionally substituted group selected from among $C_1$-$C_8$-alkyl, $C_2$-$C_6$-alkenyl, $C_3$-$C_8$-cycloalkyl, $C_2$-$C_6$-haloalkyl, $C_6$-$C_{14}$-aryl, $C_5$-$C_{10}$-heteroaryl and $C_3$-$C_8$-heterocycloalkyl, or a group selected from among =O, NR$^7$R$^8$, OR$^7$, —CO—C$_1$-C$_3$-alkyl-NR$^7$R$^8$, —O—C$_1$-C$_3$-alkyl-NR$^7$R$^8$, CONR$^7$R$^8$, NR$^7$COR$^8$, —CO—C$_1$-C$_3$-alkyl-NR$^7$(CO)OR$^8$, —O(CO)NR$^7$R$^8$, NR$^7$(CO)NR$^8$R$^9$, NR$^7$(CO)OR$^8$, (CO)OR$^7$, —O(CO)R$^7$, COR$^7$, (SO)R$^7$, (SO$_2$)R$^7$, (SO$_2$)NR$^7$R$^8$, NR$^7$(SO$_2$)R$^8$, NR$^7$(SO$_2$)NR$^8$R$^9$, CN, —C$_1$-C$_3$-alkyl-C$_6$-C$_{14}$-aryl, —NH—CO—NH—C$_1$-C$_3$-alkyl, and halogen;

n denotes 1, 2 or 3

R$^7$, R$^8$, R$^9$ which may be identical or different, denote hydrogen or an optionally substituted group selected from among C$_1$-C$_8$-alkyl, C$_3$-C$_8$-cycloalkyl, C$_2$-C$_6$-haloalkyl, C$_1$-C$_4$-alkyl-C$_3$-C$_8$-cycloalkyl, C$_3$-C$_8$-cycloalkyl-C$_1$-C$_3$-alkyl, C$_6$-C$_{14}$-aryl, C$_1$-C$_4$-alkyl-C$_6$-C$_{14}$-aryl, C$_6$-C$_{14}$-aryl-C$_1$-C$_4$-alkyl, C$_3$-C$_8$-heterocycloalkyl, C$_1$-C$_5$-alkyl-C$_3$-C$_8$-heterocycloalkyl, C$_3$-C$_8$-heterocycloalkyl-C$_1$-C$_4$-alkyl, C$_1$-C$_4$-alkyl(CO)— and C$_1$-C$_4$-alkyl-O(CO)—;

or in each case two of the substituents

R$^7$, R$^8$, R$^9$ together form an optionally substituted five-, six- or seven-membered ring, consisting of carbon atoms and optionally 1-2 heteroatoms, selected from among oxygen, sulphur and nitrogen;

optionally in the form of the tautomers, the racemates, the enantiomers, the diastereomers and the mixtures thereof, as well as optionally the pharmacologically acceptable acid addition salts, solvates and hydrates thereof, with the proviso that following compounds are excluded:
a) 1,1-dimethyl-3-(4-phenyl-4,7-dihydro-3-thia-1,4,5-triaza-cyclopenta[a]pentalen-2-yl)-urea
b) (4-phenyl-4,7-dihydro-3-thia-1,4,5-triaza-cyclopenta[a]pentalen-2-yl)-urea
c) 1-(2-dimethylamino-ethyl)-3-(4-phenyl-4,7-dihydro-3-thia-1,4,5-triaza-cyclopenta[a]pentalen-2-yl)-urea
d) 1-(2-dimethylamino-ethyl)-1-methyl-3-(4-phenyl-4,7-dihydro-3-thia-1,4,5-triaza-cyclopenta[a]pentalen-2-yl)-urea
e) 4-methyl-piperazine-1-carboxylic acid (4-phenyl-4,7-dihydro-3-thia-1,4,5-triaza-cyclopenta[a]pentalen-2-yl)-amide
f) 1-[4-(2-chloro-phenyl)-4,7-dihydro-3-thia-1,4,5-triaza-cyclopenta[a]pentalen-2-yl]-3-(2-dimethylamino-ethyl)-urea
g) 3-[4-(2-chloro-phenyl)-4,7-dihydro-3-thia-1,4,5-triaza-cyclopenta[a]pentalen-2-yl]-1-(2-dimethylamino-ethyl)-1-methyl-urea
h) 1-[4-(2-chloro-phenyl)-4,7-dihydro-3-thia-1,4,5-triaza-cyclopenta[a]pentalen-2-yl]-3-methyl-urea
i) 1-[4-(2-chloro-phenyl)-4,7-dihydro-3-thia-1,4,5-triaza-cyclopenta[a]pentalen-2-yl]-3-(2-imidazol-1-yl-ethyl)-urea
j) 3-[4-(2-chloro-phenyl)-4,7-dihydro-3-thia-1,4,5-triaza-cyclopenta[a]pentalen-2-yl]-1,1-dimethyl-urea, and
k) piperidine-1-carboxylic acid (4-phenyl-4,7-dihydro-3-thia-1,4,5-triaza-cyclopenta[α]pentalen-2-yl)-amide Preferred are compounds of formula (I), wherein X, Y, Q and G may have the meaning specified and R$^a$ denotes hydrogen or a group selected from among C$_1$-C$_8$-alkyl, C$_2$-C$_8$-alkenyl, C$_2$-C$_8$-alkynyl, C$_3$-C$_8$-cycloalkyl, C$_3$-C$_8$-cycloalkenyl, C$_1$-C$_6$-haloalkyl, C$_6$-C$_{14}$-aryl, C$_6$-C$_{14}$-aryl-C$_1$-C$_5$-alkyl, C$_5$-C$_{10}$-heteroaryl, C$_3$-C$_8$-cycloalkyl-C$_1$-C$_4$-alkyl, C$_3$-C$_8$-cycloalkenyl-C$_1$-C$_4$-alkyl, C$_5$-C$_{10}$-heteroaryl-C$_1$-C$_4$-alkyl, C$_9$-C$_{13}$-spiro, C$_3$-C$_8$-heterocycloalkyl and C$_3$-C$_8$-heterocycloalkyl-C$_1$-C$_4$-alkyl, which may optionally be substituted by one or more of the groups, which may be identical or different, selected from among C$_1$-C$_6$-alkyl, C$_2$-C$_6$-alkenyl, C$_2$-C$_6$-alkynyl, C$_3$-C$_8$-cycloalkyl, C$_1$-C$_6$-haloalkyl, halogen, OH, C$_1$-C$_4$-alkoxy, CN, NO$_2$, NR$^{10}$R$^{11}$, OR$^{10}$, COR$^{10}$, COOR$^{10}$, CONR$^{10}$R$^{11}$, NR$^{10}$COR$^{11}$, NR$^{10}$(CO)NR$^{11}$R$^{12}$, O(CO)NR$^{10}$R$^{11}$, NR$^{10}$(CO)OR$^{11}$, SO$_2$R$^{10}$, SOR$^{10}$, SO$_2$NR$^{10}$R$^{11}$, NR$^{10}$SO$_2$NR$^{11}$R$^{12}$ and NR$^{10}$SO$_2$R$^{11}$;

R$^{10}$, R$^{11}$, R$^{12}$ which may be identical or different, denote hydrogen or a group selected from among C$_1$-C$_6$-alkyl, C$_2$-C$_6$-alkenyl, C$_2$-C$_6$-alkynyl, C$_3$-C$_8$-cycloalkyl and C$_1$-C$_6$ haloalkyl; or in each case two of the groups R$^{10}$, R$^{11}$, R$^{12}$ together form a five-, six- or seven-membered ring, consisting of carbon atoms and optionally 1-2 heteroatoms, selected from among oxygen, sulphur and nitrogen;

R$^b$ denotes hydrogen, NH$_2$ or OH, or an optionally substituted group selected from among C$_1$-C$_8$-alkyl, C$_3$-C$_8$-cycloalkyl, C$_2$-C$_8$-alkenyl, C$_2$-C$_8$-alkynyl, C$_3$-C$_8$-cycloalkenyl, C$_1$-C$_6$-haloalkyl, C$_6$-C$_{14}$-aryl, C$_6$-C$_{14}$-aryl-C$_1$-C$_5$-alkyl, C$_5$-C$_{10}$-heteroaryl, C$_3$-C$_8$-cycloalkyl-C$_1$-C$_4$-alkyl, C$_3$-C$_8$-cycloalkenyl-C$_1$-C$_4$-alkyl, C$_5$-C$_{10}$-heteroaryl-C$_1$-C$_4$-alkyl, C$_9$-C$_{13}$-spiro, C$_3$-C$_8$-heterocycloalkyl, CONH$_2$, C$_6$-C$_{14}$-aryl-NH, C$_3$-C$_8$-heterocycloalkyl-NH— and OMe which may optionally be substituted by one or more of the groups, which may be identical or different, selected from among C$_1$-C$_6$-alkyl, C$_2$-C$_6$-alkenyl, C$_2$-C$_6$-alkynyl, C$_3$-C$_8$-cycloalkyl, C$_1$-C$_6$-haloalkyl, halogen, OH, OMe, CN, NH$_2$, NHMe and NMe$_2$;

R$^1$ denotes hydrogen or a group selected from among C$_1$-C$_8$-alkyl, C$_3$-C$_8$-cycloalkyl, C$_2$-C$_8$-alkenyl, C$_2$-C$_8$-alkynyl and C$_6$-C$_{14}$-aryl-C$_1$-C$_5$-alkyl, which may optionally be substituted by one or more of the groups, which may be identical or different, selected from among halogen, NH$_2$, OH, CN, C$_1$-C$_6$-alkyl, OMe, —NH(CO)-alkyl and —(CO)O-alkyl, R$^2$ denotes hydrogen or a group selected from among C$_1$-C$_8$ alkyl, C$_3$-C$_8$-cycloalkyl, C$_2$-C$_8$-alkenyl, C$_3$-C$_8$-cycloalkenyl, C$_1$-C$_6$-haloalkyl, C$_6$-C$_{14}$-aryl, C$_6$-C$_{14}$-aryl-C$_1$-C$_5$-alkyl, C$_5$-C$_{10}$-heteroaryl, C$_3$-C$_8$-cycloalkyl-C$_1$-C$_4$-alkyl, C$_3$-C$_8$-cycloalkenyl-C$_1$-C$_4$-alkyl, C$_5$-C$_{10}$-heteroaryl-C$_1$-C$_6$-alkyl, C$_9$-C$_{13}$-spiro, C$_3$-C$_8$-heterocycloalkyl, C$_3$-C$_8$-heterocycloalkyl-C$_1$-C$_6$-alkyl- and C$_6$-C$_{14}$-aryl-C$_1$-C$_6$-alkyl, which may optionally be substituted by one or more of the groups, which may be identical or different, selected from among halogen, NH$_2$, OH, CN, C$_1$-C$_6$-alkyl, OMe, —NH(CO)-alkyl and —(CO)O-alkyl, or R$^1$ and R$^2$ together form a five-, six- or seven-membered ring consisting of carbon atoms and optionally 1 to 2 heteroatoms, selected from among oxygen, sulphur and nitrogen, which may optionally be substituted by one or more of the groups, which may be identical or different, selected from among heterocycloalkyl, halogen, NH$_2$, OH, CN, C$_1$-C$_6$-alkyl, OMe, —NH(CO)-alkyl, and —(CO)O-alkyl, or R$^1$ and R$^2$ together form an optionally substituted nine- to thirteen-membered spirocyclic ring, or R$^2$ denotes a group selected from among general formulae (A1) to (A18)

(A1)

-continued

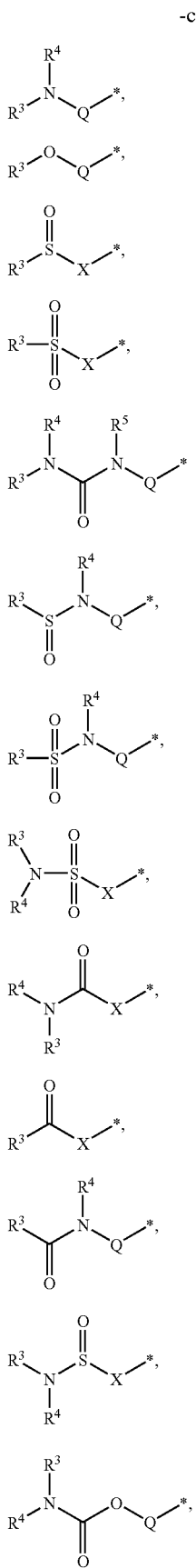

(A2)
(A3)
(A4)
(A5)
(A6)
(A7)
(A8)
(A9)
(A10)
(A11)
(A12)
(A13)
(A14)

-continued

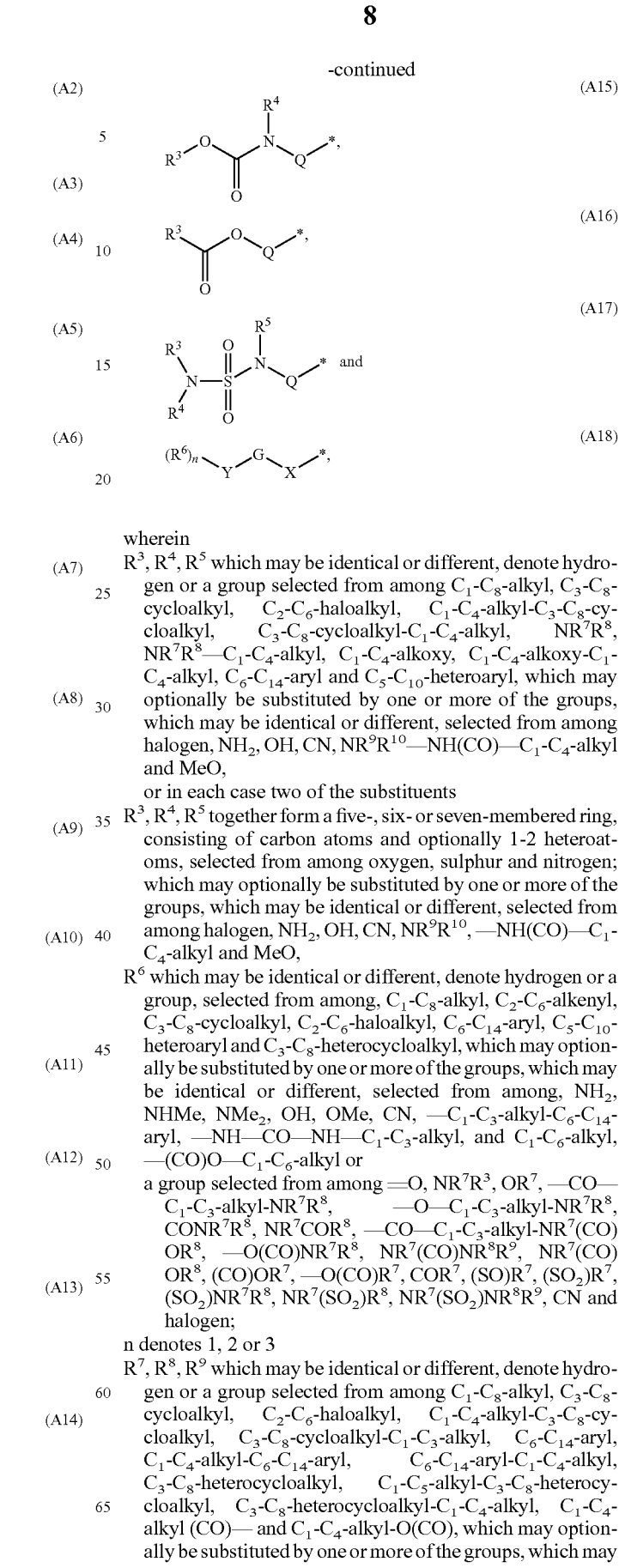

(A15)
(A16)
(A17)
(A18)

wherein $R^3$, $R^4$, $R^5$ which may be identical or different, denote hydrogen or a group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_4$-alkyl, $NR^7R^8$, $NR^7R^8$—$C_1$-$C_4$-alkyl, $C_1$-$C_4$-alkoxy, $C_1$-$C_4$-alkoxy-$C_1$-$C_4$-alkyl, $C_6$-$C_{14}$-aryl and $C_5$-$C_{10}$-heteroaryl, which may optionally be substituted by one or more of the groups, which may be identical or different, selected from among halogen, $NH_2$, OH, CN, $NR^9R^{10}$—NH(CO)—$C_1$-$C_4$-alkyl and MeO, or in each case two of the substituents $R^3$, $R^4$, $R^5$ together form a five-, six- or seven-membered ring, consisting of carbon atoms and optionally 1-2 heteroatoms, selected from among oxygen, sulphur and nitrogen; which may optionally be substituted by one or more of the groups, which may be identical or different, selected from among halogen, $NH_2$, OH, CN, $NR^9R^{10}$, —NH(CO)—$C_1$-$C_4$-alkyl and MeO, $R^6$ which may be identical or different, denote hydrogen or a group, selected from among, $C_1$-$C_8$-alkyl, $C_2$-$C_6$-alkenyl, $C_3$-$C_8$-cycloalkyl, $C_2$-$C_6$-haloalkyl, $C_6$-$C_{14}$-aryl, $C_5$-$C_{10}$-heteroaryl and $C_3$-$C_8$-heterocycloalkyl, which may optionally be substituted by one or more of the groups, which may be identical or different, selected from among, $NH_2$, NHMe, $NMe_2$, OH, OMe, CN, —$C_1$-$C_3$-alkyl-$C_6$-$C_{14}$-aryl, —NH—CO—NH—$C_1$-$C_3$-alkyl, and $C_1$-$C_6$-alkyl, —(CO)O—$C_1$-$C_6$-alkyl or a group selected from among =O, $NR^7R^3$, $OR^7$, —CO—$C_1$-$C_3$-alkyl-$NR^7R^8$, —O—$C_1$-$C_3$-alkyl-$NR^7R^8$, $CONR^7R^8$, $NR^7COR^8$, —CO—$C_1$-$C_3$-alkyl-$NR^7$(CO)$OR^8$, —O(CO)$NR^7R^8$, $NR^7$(CO)$NR^8R^9$, $NR^7$(CO)$OR^8$, (CO)$OR^7$, —O(CO)$R^7$, $COR^7$, (SO)$R^7$, ($SO_2$)$R^7$, ($SO_2$)$NR^7R^8$, $NR^7$($SO_2$)$R^8$, $NR^7$($SO_2$)$NR^8R^9$, CN and halogen;

n denotes 1, 2 or 3

$R^7$, $R^8$, $R^9$ which may be identical or different, denote hydrogen or a group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_3$-alkyl, $C_6$-$C_{14}$-aryl, $C_1$-$C_4$-alkyl-$C_6$-$C_{14}$-aryl, $C_6$-$C_{14}$-aryl-$C_1$-$C_4$-alkyl, $C_3$-$C_8$-heterocycloalkyl, $C_1$-$C_5$-alkyl-$C_3$-$C_8$-heterocycloalkyl, $C_3$-$C_8$-heterocycloalkyl-$C_1$-$C_4$-alkyl, $C_1$-$C_4$-alkyl (CO)— and $C_1$-$C_4$-alkyl-O(CO), which may optionally be substituted by one or more of the groups, which may be identical or different, selected from among halogen, $NH_2$, OH, CN, OMe, NHMe, $NMe_2$, $C_1$-$C_6$-alkyl and (CO)O $C_1$-$C_6$-alkyl, or in each case two of the substituents $R^7$, $R^8$, $R^9$ together form a five-, six- or seven-membered ring, consisting of carbon atoms and optionally 1-2 heteroatoms, selected from among oxygen, sulphur and nitrogen; which may optionally be substituted by one or more of the groups, which may be identical or different, selected from among halogen, $NH_2$, OH, CN, OMe, NHMe, $NMe_2$, $C_1$-$C_6$-alkyl and (CO)O $C_1$-$C_6$-alkyl.

Also preferred are compounds of formula (I), wherein $R^a$ and $R^1$ to $R^{12}$ may have the meaning specified and $R^b$ denotes hydrogen.

Also preferred are compounds of formula (I), wherein $R^1$ to $R^{12}$ may have the meaning specified and $R^a$ denotes $C_6$-$C_{14}$-aryl or a saturated ring system consisting of 5-6 C atoms, wherein optionally up to 4 C atoms are replaced by nitrogen atoms, wherein $R^a$ may optionally be substituted by one or more of the groups, which may be identical or different, selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, $C_1$-$C_4$-alkoxy, CN, $NO_2$, $NR^{10}R^{11}$, $OR^{10}$, $COR^{10}$, $COOR^{10}$, $CONR^{10}R^{11}$, $NR^{10}COR^{11}$, $NR^{10}(CO)NR^{11}R^{12}$, $O(CO)NR^{10}R^{11}$, $NR^{10}(CO)OR^{11}$, $SO_2R^{10}$, $SOR^{10}$, $SO_2NR^{10}R^{11}$, $NR^{10}SO_2NR^{11}R^{12}$ and $NR^{10}SO_2R^{11}$;

$R^b$ denotes hydrogen, $NH_2$ or OH, or a group selected from among $C_3$-$C_8$-cycloalkyl, $C_6$-$C_{14}$-aryl, $C_5$-$C_{10}$-heteroaryl, $C_6$-$C_{14}$-aryl-NH, $C_1$-$C_8$-alkyl, $C_2$-$C_8$-alkenyl, $C_2$-$C_8$-alkynyl and $C_1$-$C_6$ haloalkyl, which may optionally be substituted by one or more of the groups, which may be identical or different, selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, OMe, CN, $NH_2$, NHMe and $NMe_2$.

Also preferred are compounds of formula (I), wherein $R^a$ and $R^b$ may have the meaning specified and $R^1$ denotes hydrogen, $C_1$-$C_5$-alkyl or $C_3$-$C_8$-cycloalkyl, $R^2$ denotes hydrogen, $C_1$-$C_5$-alkyl or $C_3$-$C_8$-cycloalkyl, or $R^1$ and $R^2$ together form an optionally substituted five- or six-membered ring consisting of carbon atoms and optionally 1 to 2 nitrogen atoms, or $R^1$ and $R^2$ together form an optionally substituted nine- to thirteen-membered spirocyclic ring, or $R^1$, $R^2$ which may be identical or different, denote a group selected from among general formulae (A2), (A3), (A8), (A10), (A11) and (A12), wherein X denotes a bond or an optionally substituted $C_1$-$C_3$-alkylene, or X together with $R^1$, $R^3$ or $R^4$ may form a 5- or 6-membered heterocyclic group;

Q denotes an optionally substituted $C_1$-$C_3$-alkylene, or

Q together with $R^1$, $R^3$ or $R^4$ may form a $C_1$-$C_7$-alkylene bridge;

$R^3$, $R^4$, $R^5$ which may be identical or different, denote hydrogen or an optionally substituted group selected from among $C_1$-$C_4$-alkyl, $C_1$-$C_4$-alkoxy, $C_3$-$C_6$-cycloalkyl and $C_5$-$C_{10}$-heteroaryl or in each case two of the substituents $R^3$, $R^4$, $R^5$ together form an optionally substituted five- or six-membered ring, consisting of carbon atoms and optionally 1-2 heteroatoms, selected from among oxygen and nitrogen.

Particularly preferred are compounds of formula (I), wherein $R^a$ and $R^b$ may have the meaning specified and $R^1$ denotes H, Me $R^2$ denotes hydrogen or a group of general formulae (A18), wherein X denotes a bond or an optionally substituted group selected from among $C_1$-$C_7$-alkylene, $C_3$-$C_7$-alkenylene and $C_3$-$C_7$-alkynylene, or X together with $R^1$ may form a $C_1$-$C_7$-alkylene bridge;

Y denotes a bond or methylene, ethylene;

X and Y may be linked to the same or different atoms of G, and

G denotes a saturated, partially saturated or unsaturated ring system consisting of 3-10 C atoms, wherein optionally up to 6 C atoms are replaced by heteroatoms selected from among nitrogen, oxygen and sulphur;

$R^6$ which may be identical or different, denote hydrogen or an optionally substituted group selected from among =O, $C_1$-$C_4$-alkyl, $C_3$-$C_6$-cycloalkyl, $C_6$-$C_{14}$-aryl, $C_5$-$C_6$-heterocycloalkyl and $C_5$-$C_6$-heteroaryl or a group selected from among $OR^7$, $NR^7R^8$, —O—$C_1$-$C_3$-alkyl-$NR^7R^8$, $CONR^7R^8$, CO—$C_1$-$C_3$-alkyl-$NR^7R^8NR^7COR^8$, $NR^7(CO)OR^8$, —CO—$C_1$-$C_3$-alkyl-$NR^7(CO)OR^8$, $NR^7(CO)NR^8R^9$, $NR^7(CO)OR^8$, (CO)$OR^7$, $COR^7$, $(SO_2)R^7$ and CN, n denotes 1 or 2

$R^7$, $R^8$, $R^9$ which may be identical or different, denote hydrogen or an optionally substituted group selected from among $C_1$-$C_5$-alkyl, $C_1$-$C_4$-alkyl-$C_6$-$C_{14}$-aryl, $C_3$-$C_6$-heterocycloalkyl and $C_1$-$C_5$-alkyl-$C_3$-$C_8$-heterocycloalkyl, or in each case two of the substituents $R^7$, $R^8$, $R^9$ together form an optionally substituted five- or six-membered ring, consisting of carbon atoms and optionally 1-2 heteroatoms, selected from among oxygen and nitrogen.

The invention further relates to compounds of formula (I) for use as pharmaceutical compositions.

The invention further relates to the use of the compounds of formula (I) for preparing a pharmaceutical composition for the treatment of diseases in whose pathology an activity of PI3-kinases is implicated, wherein therapeutically effective doses of the compounds of formula (I) may confer a therapeutic benefit.

The invention further relates to the use of the compounds of formula (I), for preparing a pharmaceutical composition for the treatment of inflammatory and allergic diseases of the airways.

The invention further relates to the use of the compounds of formula (I), for preparing a pharmaceutical composition for the treatment of a disease, which is selected from among chronic bronchitis, bronchitis caused by bacterial or viral infections or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha1-antitrypsin deficiency, coughing, pulmonary emphysema, interstitial lung diseases, alveolitis, hyperreactive airways, nasal polyps, pulmonary oedema, pneumonitis of various causes, such as radiation-induced or caused by aspiration or infection, collagenosis such as lupus erythematodes, systemic scleroderma, sarcoidosis and Boeck's disease.

The invention further relates to the use of the compounds of formula (I), for preparing a pharmaceutical composition for the treatment of inflammatory and allergic diseases of the skin.

The invention further relates to the use of the compounds of formula (I), for preparing a pharmaceutical composition for the treatment of a disease which is selected from among psoriasis, contact dermatitis, atopical dermatitis, alopecia areata (circular hair loss), erythema exsudativum multiforme (Stevens-Johnson Syndrome), dermatitis herpetiformis, sclerodermy, vitiligo, nettle rash (urticaria), lupus erythematodes, follicular and surface pyoderma, endogenous and exogenous acne, acne rosacea and other inflammatory and allergic or proliferative skin complaints.

The invention further relates to the use of the compounds of formula (I), for preparing a pharmaceutical composition for the treatment of inflammation of the eye.

The invention further relates to the use of the compounds of formula (I), for preparing a pharmaceutical composition for the treatment a disease which is selected from among conjunctivitis of various kinds, such as e.g. caused by fungal or bacterial infections, allergic conjunctivitis, irritable conjunctivitis, conjunctivitis caused by drugs, keratitis and uveitis.

The invention further relates to the use of the compounds of formula (I), for preparing a pharmaceutical composition for the treatment of diseases of the nasal mucosa.

The invention further relates to the use of the compounds of formula (I), for preparing a pharmaceutical composition for the treatment of a disease, which is selected from among allergic rhinitis, allergic sinusitis and nasal polyps.

The invention further relates to the use of the compounds of formula (I), for preparing a pharmaceutical composition for the treatment of inflammatory or allergic conditions involving autoimmune reactions.

The invention further relates to the use of the compounds of formula (I), for preparing a pharmaceutical composition for the treatment of a disease which is selected from among Crohn's disease, ulcerative colitis, systemic lupus erythematodes, chronic hepatitis, multiple sclerosis, rheumatoid arthritis, psoriatric arthritis, osteoarthritis, rheumatoid spondylitis.

The invention further relates to the use of the compounds of formula (I), for preparing a pharmaceutical composition for the treatment of kidney inflammation.

The invention further relates to the use of the compounds of formula (I), for preparing a pharmaceutical composition for the treatment of a disease which is selected from among glomerulonephritis, interstitial nephritis and idiopathic nephrotic syndrome.

Of particular importance according to the invention is a pharmaceutical formulation containing a compound of formula (I).

Preferred is an inhaled pharmaceutical formulation containing a compound of formula (I).

Also preferred is an orally administered pharmaceutical formulation containing a compound of formula (I).

Terms and Definitions Used

By alkyl groups as well as alkyl groups which are part of other groups are meant branched and unbranched alkyl groups with 1 to 10 carbon atoms, preferably 1-6, particularly preferably 1-4 carbon atoms, are meant for example: methyl, ethyl, propyl, butyl, pentyl, hexyl, heptyl, octyl, nonyl and decyl. Unless stated otherwise, the above terms propyl, butyl, pentyl, hexyl, heptyl, octyl, nonyl and decyl include all the possible isomeric forms. For example the term propyl includes the two isomeric groups n-propyl and iso-propyl, the term butyl includes n-butyl, iso-butyl, sec. butyl and tert.-butyl, the term pentyl includes isopentyl, neopentyl etc. In the above-mentioned alkyl groups, unless otherwise specified, one or more hydrogen atoms may be replaced by other groups. For example these alkyl groups may be substituted by the halogen atoms fluorine, chlorine, bromine or iodine. The substituents fluorine or chlorine are preferred. It is also possible for all the hydrogen atoms of the alkyl group to be replaced.

By alkyl bridge is meant, unless stated otherwise, branched and unbranched double-bonded alkyl groups with 4 to 7 carbon atoms, for example, n-butylene, iso-butylene, sec. butylene and tert.-butylene, pentylene, iso-pentylene, neopentylene, etc. bridges. Particularly preferred are n-butylene or n-pentylene bridges. In the above-mentioned alkyl bridges 1 to 2 C atoms may optionally be replaced by one or more heteroatoms selected from among oxygen or sulphur.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Preferred are alkylene groups with 1 to 4 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

Examples of alkenyl groups (including those which are part of other groups) are branched and unbranched alkenyl groups with 2 to 10 carbon atoms, preferably 2-6 carbon atoms, particularly preferably 2-3 carbon atoms, provided that they have at least one double bond. Examples include: ethenyl, propenyl, butenyl, pentenyl etc. Unless stated otherwise, the above-mentioned terms propenyl, butenyl etc. include all the possible isomeric forms. For example the term butylene includes n-butenyl, 1-methylpropenyl, 2-methylpropenyl, 1,1-dimethylethenyl, 1,2-dimethylethenyl etc.

In the above-mentioned alkenyl groups, unless otherwise stated, optionally one or more hydrogen atoms may optionally be replaced by other groups. For example these alkyl groups may be substituted by the halogen atoms fluorine, chlorine, bromine or iodine. The substituents fluorine and chlorine are preferred. Particularly preferred is the substituent chlorine. Optionally all the hydrogen atoms of the alkenyl group may be replaced.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

Examples of alkynyl groups (including those which are part of other groups) are branched and unbranched alkynyl groups with 2 to 10 carbon atoms, provided that they have at least one triple bond, for example ethynyl, propargyl, butynyl, pentynyl, hexynyl etc., preferably ethynyl or propynyl.

Preferred are alkynyl groups with 2 to 4 carbon atoms. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus, for example propynyl includes 1-propynyl and 2-propynyl, butynyl includes 1-, 2- and 3-butynyl, 1-methyl-1-propynyl, 1-methyl-2-propynyl etc.

In the above-mentioned alkynyl groups one or more hydrogen atoms may optionally be substituted by other groups unless stated otherwise. For example these alkyl groups may be substituted by the halogen atoms fluorine, chlorine, bromine or iodine. The substituents fluorine and chlorine are preferred. Optionally all the hydrogen atoms of the alkynyl group may be replaced.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus, for example propynyl also includes 1-methylethynylene and butynylene includes 1-methylpropynylene, 1,1-dimethylethynylene, 1,2-dimethylethynylene.

By cycloalkyl groups (including those which are part of other groups) are meant saturated cycloalkyl groups with 3-8 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally carry one or more substituents or be anellated to a benzene ring. Moreover the cycloalkyl groups may form, in addition to monocyclic groups, bicyclic, bridged or spirocyclic ring systems.

By cycloalkenyl (including those which are part of other groups) are meant cyclic alkyl groups with 5 to 8, preferably 5 or 6 carbon atoms, which contain one or two double bonds. Examples include: cyclopentenyl, cyclopentadienyl, cyclohexenyl, cyclohexadienyl, cycloheptenyl, cycloheptadienyl, cyclooctenyl or cyclooctadienyl. Moreover the cycloalkenyl groups may form, in addition to monocyclic groups, bicyclic, bridged or spirocyclic ring systems.

By cycloalkynyl (including those which are part of other groups) are meant cyclic alkyl groups with 5 to 8, preferably 5 or 6 carbon atoms, which contain one or two triple bonds. Examples of these include: cyclopentynyl, cyclopentadiynyl, cyclohexynyl, cyclohexadiynyl, cycloheptynyl, cycloheptadiynyl, cyclooctynyl or cyclooctadiynyl. Moreover the cycloalkynyl groups may form, in addition to monocyclic ring systems, bicyclic, bridged or spirocyclic ring systems.

By haloalkyl (including those which are part of other groups) are meant branched and unbranched alkyl groups with 1 to 6 carbon atoms, wherein one or more hydrogen atoms are replaced by a halogen atom selected from among fluorine, chlorine or bromine, preferably fluorine and chlorine. By the term "$C_{1-4}$-haloalkyl" are meant correspondingly branched and unbranched alkyl groups with 1 to 4 carbon atoms, wherein one or more hydrogen atoms are replaced as described above. $C_{1-4}$-haloalkyl is preferred. Examples of these include: $CH_2F$, $CHF_2$, $CF_3$.

The term aryl denotes an aromatic ring system with 6 to 14 carbon atoms, preferably 6 or 10 carbon atoms, for example phenyl or naphthyl, preferably phenyl, which, unless otherwise described, may have one or more substituents, for example. Moreover each of the above-mentioned aryl systems may optionally be anellated to a heterocycloalkyl group or a cycloalkyl group. Examples include: 2,3-dihydro-benzo[1,4]dioxine, benzo[1,3]dioxole, 1,2,3,4-tetrahydro-naphthalene and 3,4-dihydro-1H-quinolin-2-one.

By heterocycloalkyl groups are meant, unless otherwise described in the definitions, 5-, 6- or 7-membered, saturated or unsaturated, bridged, mono- or bicyclic heterocycles wherein up to four C atoms may be replaced by one or more heteroatoms selected from among oxygen, nitrogen or sulphur, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole, pyrazolidine, preferably pyrazolyl, pyrrolidinyl, piperidinyl, piperazinyl or tetrahydro-oxazinyl, while the heterocycle may optionally be substituted, preferably by fluorine or methyl. The ring may be linked to the molecule through a carbon atom or if available through a nitrogen atom.

Unless otherwise mentioned, a heterocyclic ring may be provided with a keto group. Examples of these include.

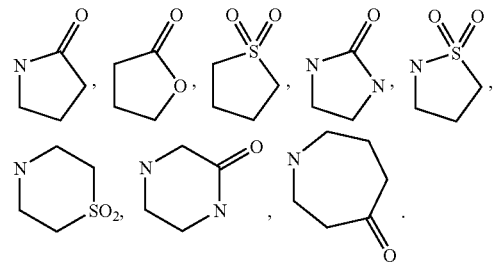

Examples of 5-10-membered bicyclic heterorings include pyrrolizine, indole, indolizine, isoindole, indazole, purine, quinoline, isoquinoline, benzimidazole, benzofuran, benzopyran, benzothiazole, benzothiazole, benzisothiazole, pyridopyrimidine, pteridine, pyrimidopyrimidine,

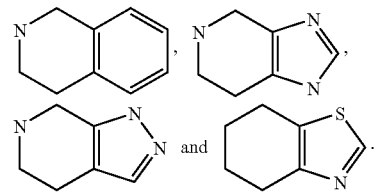

and

Examples of heteroaryl include 5-10-membered mono- or bicyclic heteroaryl rings in which up to three C atoms may be replaced by one or more heteroatoms selected from among oxygen, nitrogen or sulphur, while these may contain so many conjugated double bonds that an aromatic system is formed. Each of the above-mentioned heterocycles may optionally also be anellated to a benzene ring. Preferred examples of anellated heteraryl groups are: benzimidazole, indole and pyrimidopyrimidine. Moreover each of the above-mentioned heterocycles may optionally be anellated to a heterocycloalkyl group or a cycloalkyl group.

The heteroaryl rings may, for example, unless otherwise described, carry one or more substituents, preferably halogen or methyl.

The ring may be linked to the molecule through a carbon atom or if present through a nitrogen atom. The following are examples of five- or six-membered heterocyclic aromatic groups:

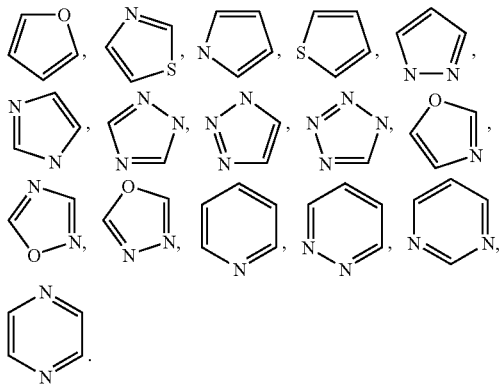

Examples of 5-10-membered bicyclic heteroaryl rings include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine.

By the term heterocyclic spiro rings ("spiro") are meant 5-13-membered, preferably 9-10-membered, spirocyclic rings which may optionally contain one, two or three heteroatoms, selected from among oxygen, sulphur and nitrogen, while the ring may be connected to the molecule via a carbon atom or, if present, via a nitrogen atom. Unless otherwise stated, a spirocyclic ring may be provided with a keto group. Examples include:

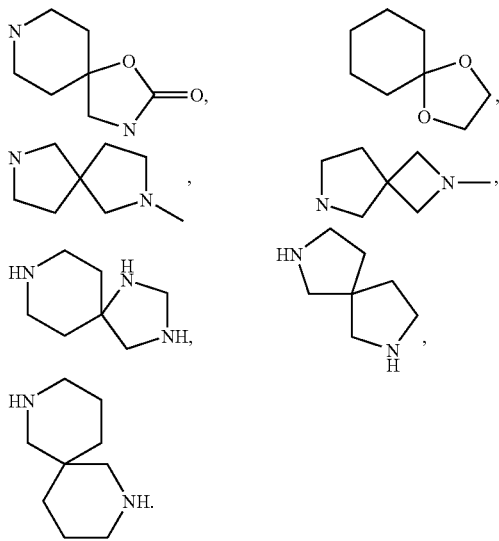

By the term "optionally substituted" is meant, unless stated otherwise, within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

"=O" denotes an oxygen atom linked by a double bond.

The term halogen generally denotes fluorine, chlorine, bromine or iodine.

The compounds according to the invention may occur in the form of the individual optical isomers, mixtures of the individual enantiomers, diastereomers or racemates, in the form of the tautomers as well as in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic or methanesulphonic acid.

Where a hyphen open on one side "-" is used in the structural formula of a substituent, this hyphen is to be understood as the linkage point to the remainder of the molecule. The substituent replaces the corresponding groups $R^2$, $R^6$, etc. If no hyphen open on one side is used in the structural formula of a substituent, the linkage point to the remainder of the molecule is clear from the structural formula itself.

The substituent $R^a$ may be hydrogen or an optionally substituted group selected from among $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, $C_9$-$C_{13}$-spiro, $C_3$-$C_8$-heterocycloalkyl and $C_3$-$C_8$-heterocycloalkyl-$C_1$-$C_4$-alkyl, preferably phenyl, wherein $R^a$ may preferably be substituted by a group selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, $C_1$-$C_4$-alkoxy, CN, $NO_2$, $NR^{10}R^{11}$, $OR^{10}$, $COR^{10}$, $COOR^{10}$, $CONR^{10}R^{11}$, $NR^{10}COR^{11}$, $NR^{10}(CO)NR^{11}R^{12}$, $O(CO)NR^{10}R^{11}$, $NR^{10}(CO)OR^{11}$, $SO_2R^{10}$, $SOR^{10}$, $SO_2NR^{10}R^{11}$, $NR^{10}SO_2NR^{11}R^{12}$ and $NR^{10}SO_2R^{11}$, preferably $C_1$-$C_6$-haloalkyl, halogen and $CONR10R^{11}$, particularly preferably $CF_3$, F, Cl, Br and $CONHCH_3$.

Particularly preferably $R^a$ denotes phenyl, optionally substituted by one or more of the groups selected from among $CF_3$, F, Cl, Br and $CONHCH_3$.

The substituents $R^{10}$, $R^{11}$, $R^{12}$, which may be identical or different, may denote hydrogen or a group selected from among $C_1$-$C_6$-alkyl, $C_2$-$C_6$-alkenyl, $C_2$-$C_6$-alkynyl, $C_3$-$C_8$-cycloalkyl and $C_1$-$C_6$ haloalkyl; or in each case two of the groups R$^{10}$, R$^{11}$, R$^{12}$ together form a five-, six- or seven-membered ring, consisting of carbon atoms and optionally 1-2 heteroatoms, selected from among oxygen, sulphur and nitrogen.

The substituent R$^b$ may represent hydrogen, NH$_2$ or OH, or an optionally substituted group selected from among C$_1$-C$_8$-alkyl, C$_3$-C$_8$-cycloalkyl, C$_2$-C$_8$-alkenyl, C$_2$-C$_8$-alkynyl, C$_3$-C$_8$-cycloalkenyl, C$_1$-C$_6$-haloalkyl, C$_6$-C$_{14}$-aryl, C$_6$-C$_{14}$-aryl-C$_1$-C$_5$-alkyl, C$_5$-C$_{10}$-heteroaryl, C$_3$-C$_8$-cycloalkyl-C$_1$-C$_4$-alkyl, C$_3$-C$_8$-cycloalkenyl-C$_1$-C$_4$-alkyl, C$_5$-C$_{10}$-heteroaryl-C$_1$-C$_4$-alkyl, C$_{9-13}$-spiro, C$_3$-C$_8$-heterocycloalkyl, CONH$_2$, C$_6$-C$_{14}$-aryl-NH, C$_3$-C$_8$-heterocycloalkyl-NH— and O-Me, which is preferably unsubstituted or substituted by one or more of the groups, which may be identical or different, selected from among C$_1$-C$_6$-alkyl, C$_2$-C$_6$-alkenyl, C$_2$-C$_6$-alkynyl, C$_3$-C$_8$-cycloalkyl, C$_1$-C$_6$-haloalkyl, halogen, OH, OMe, CN, NH$_2$, NHMe and NMe$_2$.

Preferably R$^b$ denotes hydrogen, NH$_2$ or OH, or a group selected from among C$_3$-C$_8$-cycloalkyl, C$_6$-C$_{14}$-aryl, C$_5$-C$_{10}$-heteroaryl, C$_6$-C$_{14}$-aryl-NH, C$_1$-C$_8$-alkyl, C$_2$-C$_8$-alkenyl, C$_2$-C$_8$-alkynyl, C$_1$-C$_6$ haloalkyl, which may optionally be substituted by one or more of the groups, which may be identical or different, selected from among C$_1$-C$_6$-alkyl, C$_2$-C$_6$-alkenyl, C$_2$-C$_6$-alkynyl, C$_3$-C$_8$-cycloalkyl, C$_1$-C$_6$-haloalkyl, halogen, OH, OMe, CN, NH$_2$, NHMe and NMe$_2$.

Particularly preferably R$^b$ denotes hydrogen.

The substituent R$^1$ may represent hydrogen or an optionally substituted group selected from among C$_1$-C$_8$-alkyl, C$_3$-C$_8$-cycloalkyl, C$_2$-C$_8$-alkenyl, C$_2$-C$_8$-alkynyl and C$_6$-C$_{14}$-aryl-C$_1$-C$_5$-alkyl. Preferably R$^1$ denotes hydrogen, C$_1$-C$_5$-alkyl or C$_3$-C$_8$-cycloalkyl. Particularly preferably the substituent R$^1$ denotes hydrogen or a group selected from among methyl, ethyl, propyl, cyclopropyl and piperidine; particularly preferably R$^1$ denotes hydrogen or methyl.

The substituent R$^1$ may preferably be substituted by one or more of the groups, which may be identical or different, selected from among halogen, NH$_2$, OH, CN, C$_1$-C$_6$-alkyl, OMe, —NH(CO)alkyl and —(CO)O—C$_1$-C$_4$-alkyl.

The substituent R$^2$ may represent hydrogen or an optionally substituted group selected from among C$_1$-C$_8$ alkyl, C$_3$-C$_8$-cycloalkyl, C$_2$-C$_8$-alkenyl, C$_3$-C$_8$-cycloalkenyl, C$_1$-C$_6$-haloalkyl, C$_6$-C$_{14}$-aryl, C$_6$-C$_{14}$-aryl-C$_1$-C$_5$-alkyl, C$_5$-C$_{10}$-heteroaryl, C$_3$-C$_8$-cycloalkyl-C$_1$-C$_4$-alkyl, C$_3$-C$_8$-cycloalkenyl-C$_1$-C$_4$-alkyl, C$_5$-C$_{10}$-heteroaryl-C$_1$-C$_6$-alkyl, C$_9$-C$_{13}$-spiro, C$_3$-C$_8$-heterocycloalkyl, C$_3$-C$_8$-heterocycloalkyl-C$_1$-C$_6$-alkyl- and C$_6$-C$_{14}$-aryl-C$_1$-C$_6$-alkyl-. Preferably R$^2$ denotes hydrogen or a group selected from among C$_1$-C$_5$-alkyl, C$_3$-C$_8$-cycloalkyl-C$_1$-C$_4$-alkyl, C$_6$-C$_{14}$-aryl-C$_1$-C$_5$-alkyl, C$_3$-C$_8$-heterocycloalkyl-C$_1$-C$_6$-alkyl- and C$_5$-C$_{10}$-heteroaryl-C$_1$-C$_6$-alkyl-. Particularly preferably R$^2$ denotes hydrogen or a group selected from among methyl, ethyl, propyl, butyl, pentyl, —CH$_2$—C$_3$-C$_6$-cycloalkyl, —CH$_2$-phenyl, —CH$_2$—C$_5$-C$_6$-heteroaryl and —CH$_2$—C$_3$-C$_6$-heterocycloalkyl.

The substituent R$^2$ may preferably be substituted by one or more of the groups, which may be identical or different, selected from among halogen, NH$_2$, OH, CN, C$_1$-C$_6$-alkyl, OMe, —NH(CO)alkyl and —(CO)O—C$_1$-C$_4$-alkyl.

The substituents R$^1$ and R$^2$ may together form an optionally substituted, five-, six- or seven-membered ring consisting of carbon atoms and optionally 1 to 2 heteroatoms, selected from among oxygen, sulphur and nitrogen, preferably nitrogen. Particularly preferably the group NR$^1$R$^2$ denotes an optionally substituted pyrrolidinyl group.

The ring formed from the substituents R$^1$ and R$^2$ may preferably be substituted by one or more of the groups, which may be identical or different, selected from among heterocycloalkyl, halogen, NH$_2$, OH, CN, C$_1$-C$_6$-alkyl, OMe, —NH(CO)alkyl and —(CO)O—C$_1$-C$_4$-alkyl.

The substituents R$^1$ and R$^2$ may together form an optionally substituted nine- to thirteen-membered spirocyclic ring, preferably

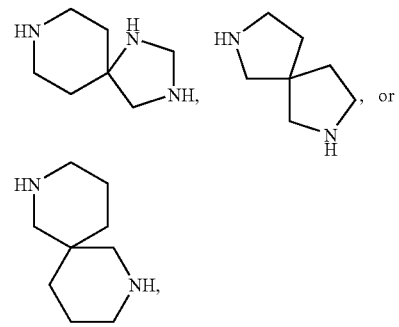

which is preferably substituted by a group selected from among methyl, ethyl, OH, =O and phenyl.

The substituent R$^2$ may furthermore denote a group selected from among general formulae (A1) to (A18)

(A1)

(A2)

(A3)

(A4)

(A5)

(A6)

(A7)

(A8)

-continued

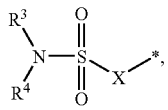 (A9)

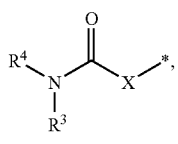 (A10)

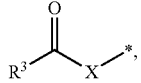 (A11)

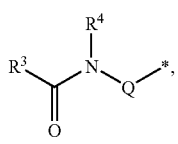 (A12)

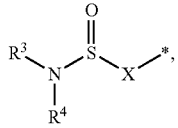 (A13)

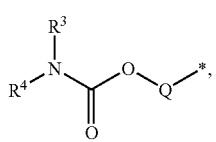 (A14)

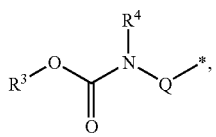 (A15)

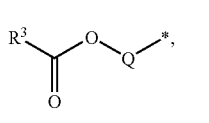 (A16)

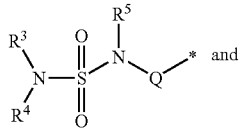 (A17) and

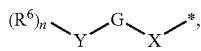 (A18)

preferably (A1), (A10), (A11) and (A18).

X and Y may be linked to the same or different atoms of G.

X may denote a bond or an optionally substituted group selected from among $C_1$-$C_7$-alkylene, $C_3$-$C_7$-alkenylene and $C_3$-$C_7$-alkynylene, preferably a bond, methyl, ethyl and propyl, most preferably a bond or methyl.

X may form together with $R^1$, $R^3$ or $R^4$ a 5- or 6-membered heterocyclic group, particularly preferably may form a piperidinone or pyrrolidinone ring with $R^3$ or $R^4$, which may optionally be substituted. The substituent $R^1$ and X preferably form a pyrrolidine or piperidine group.

Y may represent a bond or optionally substituted $C_1$-$C_4$-alkylene, preferably a bond, methylene or ethylene.

Q may denote an optionally substituted group selected from among $C_1$-$C_7$-alkylene, $C_3$-$C_7$-alkenylene and $C_3$-$C_7$-alkynylene; preferably optionally substituted $C_1$-$C_3$-alkylene, particularly preferably ethyl and propyl.

Q together with $R^1$, $R^3$ or $R^4$ may form a $C_1$-$C_7$-alkylene bridge.

The substituents $R^3$, $R^4$, $R^5$ which may be identical or different, may denote hydrogen or an optionally substituted group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_4$-alkyl, $NR^7R^8$, $NR^7R^8$—$C_1$-$C_4$-alkyl, $C_1$-$C_4$-alkoxy, $C_1$-$C_4$-alkoxy-$C_1$-$C_4$-alkyl, $C_6$-$C_{14}$-aryl and $C_5$-$C_{10}$-heteroaryl; preferably hydrogen, or an optionally substituted group selected from among $C_1$-$C_4$-alkyl, $C_1$-$C_4$-alkoxy and $C_3$-$C_6$-cycloalkyl, particularly preferably hydrogen, methyl, methoxy, ethoxy, butyloxy and cyclopropyl.

Two of the substituents $R^3$, $R^4$, $R^5$ may together form an optionally substituted five-, six- or seven-membered ring, preferably a 5- or 6-membered ring, consisting of carbon atoms and optionally 1-2 heteroatoms, selected from among oxygen, sulphur and nitrogen; preferably from oxygen or nitrogen. Preferably the group $NR^3R^4$ denotes pyrrolidine or dihydroimidazolidinone.

The substituents $R^3$, $R^4$, $R^5$ or the ring formed from them may preferably be substituted by one or more of the groups, which may be identical or different, selected from among halogen, $NH_2$, OH, CN, $NR^9R^{10}$, —NH(CO)—$C_1$-$C_4$-alkyl and MeO.

G may represent a saturated, partially saturated or unsaturated ring system consisting of 3-10 C atoms, wherein optionally up to 4 C atoms are replaced by heteroatoms selected from among nitrogen, oxygen and sulphur. Preferably G may represent a saturated, partially saturated or unsaturated ring system consisting of 3-8 C atoms, particularly preferably 5-6 C atoms, wherein optionally up to 6 C atoms, particularly preferably up to 4 C atoms are replaced by heteroatoms selected from among nitrogen, oxygen and sulphur. Preferably G denotes a ring system consisting of one or two 5-6-membered rings, particularly preferably selected from among cyclohexyl, phenyl, pyrrolidine, piperidine, piperazine, pyrazole, pyridine, imidazole, thiazole, triazole, oxazole, oxadiazole, tetrazole, benzimidazole, benzopyrrole and dihydro-benzo[1,4]dioxine, particularly preferably benzimidazole, cyclohexyl, phenyl, pyrrolidine, piperidine, pyrazole, imidazole, thiazole, oxazole, oxadiazole and tetrazole.

The substituent $R^6$, which may be identical or different, may denote hydrogen or an optionally substituted group, selected from among $C_1$-$C_8$-alkyl, $C_2$-$C_6$-alkenyl, $C_3$-$C_8$-cycloalkyl, $C_2$-$C_6$-haloalkyl, $C_6$-$C_{14}$-aryl, $C_5$-$C_{10}$-heteroaryl, $C_3$-$C_8$-heterocycloalkyl, preferably hydrogen or an optionally substituted group selected from among $C_1$-$C_4$-alkyl, $C_3$-$C_6$-cycloalkyl, $C_6$-$C_{14}$-aryl, $C_5$-$C_6$-heterocycloalkyl, and $C_5$-$C_6$-heteroaryl, particularly preferably hydrogen or an optionally substituted group selected from among $C_1$-$C_4$-alkyl, $C_3$-$C_6$-cycloalkyl, $C_5$-$C_6$-heterocycloalkyl, $C_5$-$C_6$-heteroaryl and phenyl, particularly preferably methyl, phenyl, imidazole, imidazolidine, pyrazole, cyclopropyl, cyclopentyl and cyclohexyl, or denotes a group selected from among =O, $NR^7R^8$, $OR^7$, —CO—$C_1$-$C_3$-alkyl-$NR^7R^8$, —O—$C_1$-$C_3$-alkyl-$NR^7R^8$, $CONR^7R^8$, $NR^7COR^8$, $NR^7(CO)OR^8$, —CO—$C_1$-$C_3$-alkyl-$NR^7(CO)OR^8$, —O(CO)$NR^7R^8$, $NR^7(CO)NR^8R^9$, $NR^7(CO)OR^8$, $(CO)OR^7$, —O(CO)$R^7$, $COR^7$, $(SO)R^7$, $(SO_2)R^7$, $(SO_2)NR^7R^8$, $NR^7(SO_2)R^8$, $NR^7(SO_2)NR^8R^9$, CN and halogen;

preferably it denotes a group selected from among =O, $NR^7R^8$, $OR^7$, —CO—$C_1$-$C_3$-alkyl-$NR^7R^8$, $CONR^7R^8$, $NR^7(CO)OR^8$, $NR^7COR^8$, —CO—$C_1$-$C_3$-alkyl-$NR^7(CO)OR^8$, $NR^7(CO)NR^8R^9$, $NR^7(CO)OR^8$, $(CO)OR^7$, $COR^7$, $(SO_2)R^7$ und CN, particularly preferably =O, OMe, —NMe-CO—NH—$C_1$-$C_3$-alkyl, —NH—CO—$C_1$-$C_4$-alkyl, —NH—COO—$C_1$-$C_4$-alkyl, —COO—$C_1$-$C_4$-alkyl and $C_1$-$C_4$-alkyl.

The substituent $R^6$ may preferably be substituted by one or more of the groups, which may be identical or different, selected from among $NH_2$, NHMe, $NMe_2$, OH, OMe, CN, —$C_1$-$C_3$-alkyl-$C_6$-$C_{14}$-aryl, —NH—CO—NH—$C_1$-$C_3$-alkyl and —(CO)O—$C_1$-$C_4$-alkyl.

n denotes 1, 2 or 3, preferably 1 or 2, particularly preferably 1.

The substituents $R^7$, $R^8$, $R^9$ which may be identical or different, may denote hydrogen or an optionally substituted group selected from among $C_1$-$C_8$-alkyl, $C_3$-$C_8$-cycloalkyl, $C_1$-$C_6$-haloalkyl, $C_1$-$C_4$-alkyl-$C_3$-$C_8$-cycloalkyl, $C_3$-$C_8$-cycloalkyl-$C_1$-$C_3$-alkyl, $C_6$-$C_{14}$-aryl, $C_1$-$C_4$-alkyl-$C_6$-$C_{14}$-aryl, $C_6$-$C_{14}$-aryl-$C_1$-$C_4$-alkyl, $C_3$-$C_8$-heterocycloalkyl, $C_1$-$C_5$-alkyl-$C_3$-$C_8$-heterocycloalkyl, $C_3$-$C_8$-heterocycloalkyl-$C_1$-$C_4$-alkyl, $C_1$-$C_4$-alkyl(CO)— and $C_1$-$C_4$-alkyl-O(CO)—; preferably $C_1$-$C_4$-alkyl, $C_1$-$C_2$-haloalkyl, $C_1$-$C_4$-alkyl-$C_3$-$C_8$-cycloalkyl, $C_3$-$C_8$-cycloalkyl-$C_1$-$C_3$-alkyl, phenyl, $C_1$-$C_4$-alkyl-$C_6$-$C_{14}$-aryl, $C_3$-$C_8$-heterocycloalkyl, $C_1$-$C_5$-alkyl-$C_3$-$C_8$-heterocycloalkyl, $C_1$-$C_4$-alkyl(CO)— and $C_1$-$C_4$-alkyl-O(CO)—, particularly preferably $C_1$-$C_5$-alkyl, $C_1$-$C_4$-alkyl-$C_6$-$C_{14}$-aryl, $C_3$-$C_6$-heterocycloalkyl and $C_1$-$C_5$-alkyl-$C_3$-$C_8$-heterocycloalkyl, or in each case two of the substituents $R^7$, $R^8$, $R^9$ together form an optionally substituted five-, six- or seven-membered ring, consisting of carbon atoms and optionally 1-2 heteroatoms, selected from among oxygen, sulphur and nitrogen, preferably an optionally substituted five- or six-membered ring, consisting of carbon atoms and optionally 1-2 heteroatoms, selected from among oxygen and nitrogen; particularly preferably nitrogen.

The substituents $R^7$, $R^8$, $R^9$ or the ring system formed therefrom may preferably be substituted by one or more of the groups, which may be identical or different, selected from among halogen, $NH_2$, OH, CN, OMe, NHMe, $NMe_2$, $C_1$-$C_6$-alkyl and (CO)O $C_1$-$C_6$-alkyl.

Preparation Processes

The compounds of general formula (I) may be prepared according to the following synthesis plan (Diagram 1-4), wherein the substituents of general formula (I) have the meanings given above. These processes are intended as an illustration of the invention without restricting it to their content.

Diagram 1:

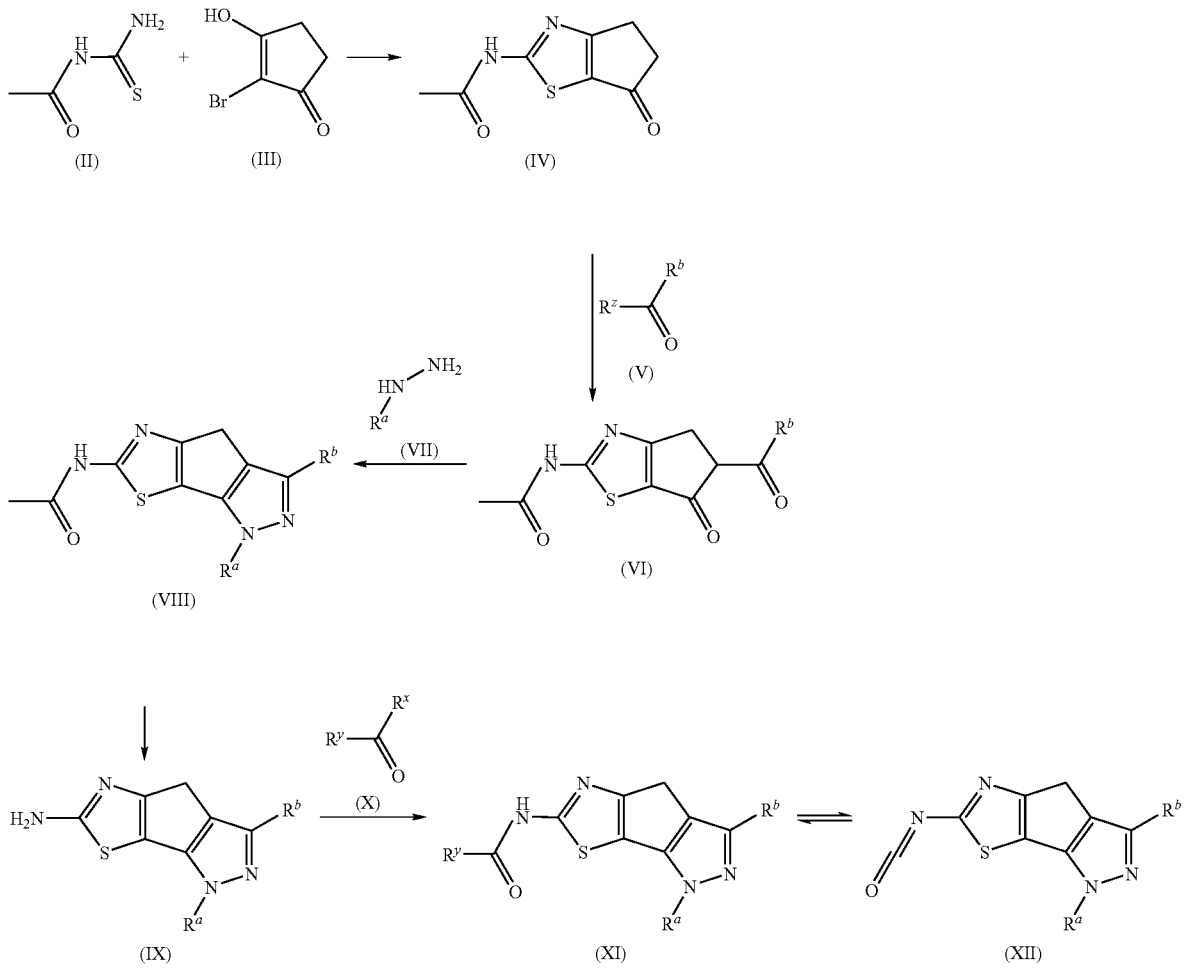

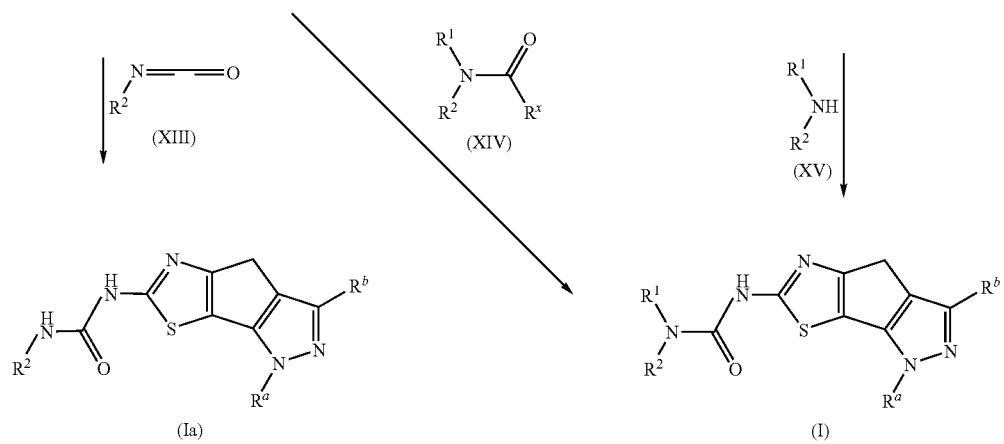

Intermediate compound (IV) is obtained by reacting 2-bromo-cyclopentan-1,3-dione (III) with acetylthiourea (II). After deprotonation with a suitable base selected from, for example, but not restricted to the group comprising sodium methoxide, sodium ethoxide, lithium hexamethylsilazide, sodium hydride this may be converted into the intermediate compound (VI) with a suitable acylating reagent (V). $R^b$ has the meanings given hereinbefore. $R^z$ is a suitable leaving group selected from, for example, but not restricted to the group comprising halogen, S-alkyl, S-aryl, O-alkylsulphonyl, O-arylsulphonyl, O-alkyl, imizazole, O-hetaryl, O-acyl, O-aryl, wherein O-aryl may optionally be substituted by suitable electron-attracting groups (e.g. nitro). The intermediate compound (VIII) is obtained by reacting with a suitable hydrazine (VII) or one of the salts thereof. $R^a$ has the meanings given hereinbefore. The compound thus obtained is then converted into the free aminothiazole (IX) by cleaving the acetyl group (e.g. by acidic or basic saponification or reaction with hydrazine hydrate). The reaction to obtain the ureas of general formula (I) or (Ia) is then carried out using one of the following methods: Direct reaction with a suitable isocyanate (XIII) leads directly to compounds of formula (Ia). Reaction with a suitable reagent (XIV) leads to compounds of formula (I), wherein $R^x$ denotes a suitable leaving group selected from, for example, but not restricted to the group comprising halogen, S-alkyl, S-aryl, O-alkylsulphonyl, O-arylsulphonyl, O-alkyl, imizazole, O-hetaryl, O-acyl, O-aryl, wherein O-aryl may optionally be substituted by suitable electron-attracting groups (e.g. nitro). Another possibility is to react the aminothiazole (IX) with a reagent of general formula (X) to form an activated intermediate compound (XI). $R^x$ and $R^y$ are identical or different suitable leaving groups e.g. selected from, but not restricted to, the group comprising halogen, S-alkyl, S-aryl, O-alkylsulphonyl, O-arylsulphonyl, O-alkyl, imizazole, O-hetaryl, O-acyl, O-aryl, wherein O-aryl may optionally be substituted by suitable electron-attracting groups (e.g. nitro). Depending on the nature of the leaving group and the temperature the intermediate compound (XI) is optionally in equilibrium with the isocyanate (XII), which can be formed by elimination of the leaving group $R^y$ from (XI). The further reaction of the intermediate compound (XI), (XII) or a mixture of the two with suitable amines of general formula (XV) leads to the desired compounds of general formula (I). $R^1$ and $R^2$ have the meanings given hereinbefore.

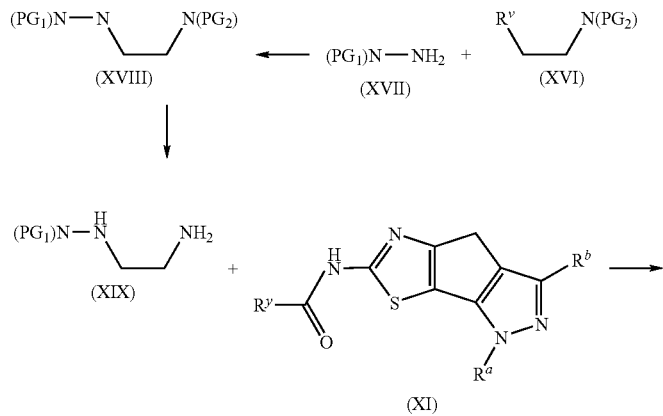

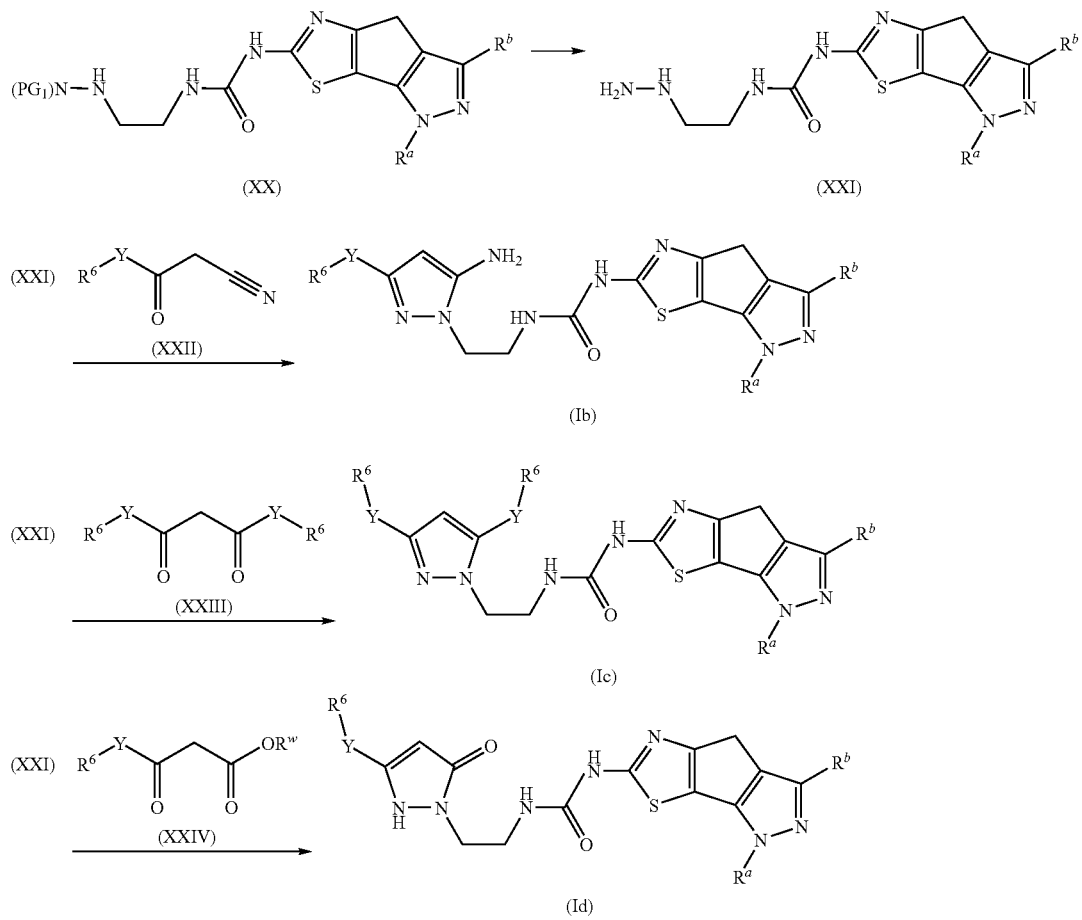

Reagents of general formula (XIX) can be prepared as follows: The reaction of a reagent of general formula (XVI) with a hydrazine of general formula (XVII) yields the intermediate compound (XVIII). Rv is a suitable leaving group, e.g. selected from, but not restricted to, the group comprising halogen, S-alkyl, S-aryl, arylsulphonyl-, alkyl-sulphonyl-. PG1 and PG2 are different (orthogonal) suitable amine-protecting groups e.g. selected from, but not restricted to, the group comprising alkylcarbonyl-(carbamates), phthalic acid imides, benzyl-(optionally substituted e.g. p-methoxybenzyl). Cleaving of the protective group PG2 under suitable conditions which leave the protective group PG1 intact leads to the reagent (XIX). The reaction of this reagent with the intermediate compound (XI) described hereinbefore yields the intermediate compound (XX), which can be converted into the intermediate compound (XXI) by suitable conditions for removal of the protective group PG2. By reacting the intermediate compound (XXI) with beta-ketonitriles of general formula (XXII) aminopyrazoles of general formula (Ib) can be obtained. Reaction of the intermediate compound (XXI) with 1,3-diketo compounds of general formula (XXIII) yields pyrazoles of formula (Ic). Pyrazolones of general formula (Id) can finally be obtained by reacting the intermediate compound (XXI) with beta-ketoesters of formula (XXIV). Y and R6 have the meanings given hereinbefore. Rw denotes an alkyl group.

Diagram 3:

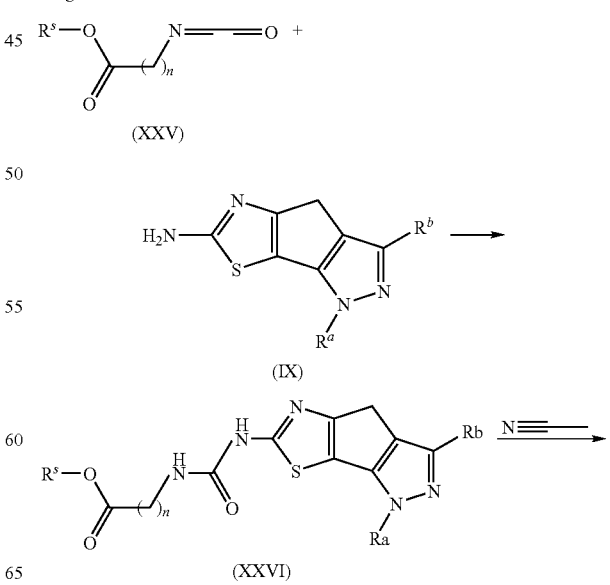

-continued

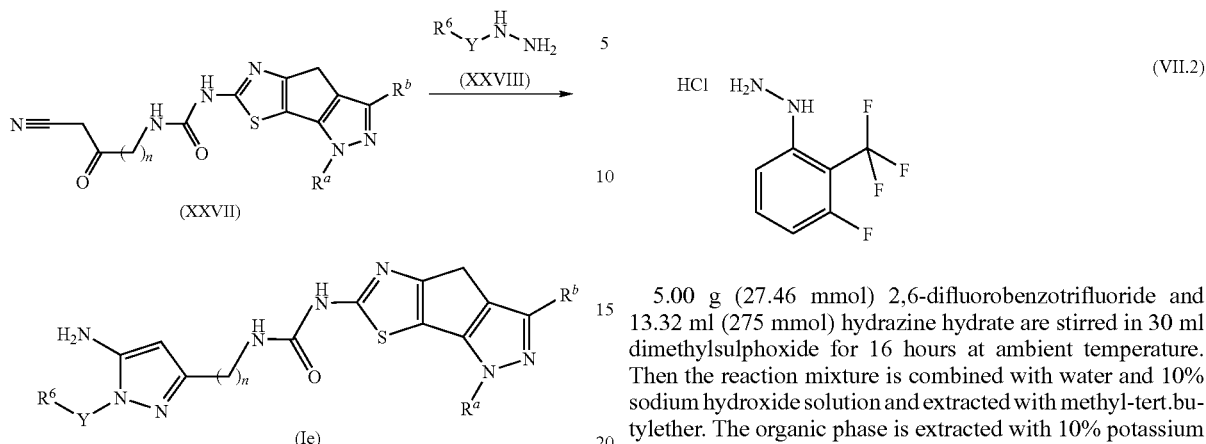

By reacting a reagent of general formula (XXV) with the intermediate compound (IX) described hereinbefore an intermediate compound of general formula (XXVI) may be obtained. R⁵ is a group selected from, for example, but not restricted to the group comprising alkyl, aryl. Reaction of the intermediate compound (XXVI) thus obtained with acetonitrile, which has previously been deprotonated with a suitable base (e.g. n-butyllithium) yields the beta-ketonitrile compound (XXVII). By reacting this compound with suitable hydrazines of general formula (XXVIII) aminopyrazoles of general formula (Ie) are obtained.

The new compounds of general formula (I) may be prepared analogously to the following Examples. The Examples described below are intended as an illustration of the invention without restricting it.

Synthesis of the Reagents (5-Fluoro-2-trifluoromethyl-phenyl)-hydrazine hydrochloride (VII.1)

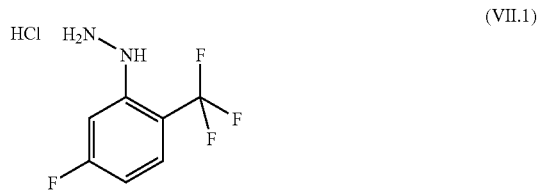

5.00 g (27.46 mmol) 2,4-difluorobenzotrifluoride and 13.32 ml (275 mmol) hydrazine hydrate are stirred in 30 ml dimethylsulphoxide for 16 hours at ambient temperature. Then the reaction mixture is combined with water and 10% sodium hydroxide solution and extracted with methyl-tert.butylether. The organic phase is evaporated to dryness. The residue is purified by chromatography, then precipitated as the hydrochloride.

Yield: 0.88 g (14% of theoretical)
HPLC-MS: method B, RT=1.46 min, MH+=195

(3-Fluoro-2-trifluoromethyl-phenyl)-hydrazine hydrochloride (VII.2)

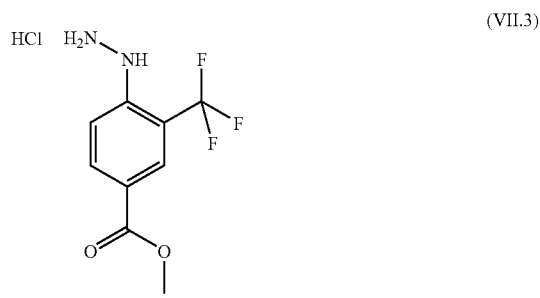

5.00 g (27.46 mmol) 2,6-difluorobenzotrifluoride and 13.32 ml (275 mmol) hydrazine hydrate are stirred in 30 ml dimethylsulphoxide for 16 hours at ambient temperature. Then the reaction mixture is combined with water and 10% sodium hydroxide solution and extracted with methyl-tert.butylether. The organic phase is extracted with 10% potassium hydrogen sulphate solution, the resulting aqueous phase is made basic and extracted with methyl-tert.butylether. The organic phase is dried and evaporated to dryness. The residue is precipitated as the hydrochloride.

Yield: 4.22 g (67% of theoretical)
HPLC-MS: method B, RT=1.39 min, MH+=195 methyl 4-hydrazino-3-trifluoromethyl-benzoate hydrochloride (VII.3)

(VII.3)

methyl 4-amino-3-trifluoromethyl-benzoate

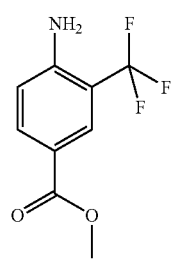

81.70 g (439 mmol) 4-amino-3-trifluoromethyl-benzonitrile are dissolved in 1000 ml of methanol, cooled to 0° C. Within 1.2 hours hydrochloric acid is added in gaseous form. Then the reaction mixture is refluxed for 5 hours with stirring, then diluted with water, cooled to 3° C. and suction filtered. The precipitate is washed with water and dried.

Yield: 73.10 g (76% of theoretical)

methyl 4-hydrazino-3-trifluoromethyl-benzoate hydrochloride (VII.3)

6.54 g (30 mmol) methyl 4-amino-3-trifluoromethyl-benzoate are suspended in 50 ml 32% hydrochloric acid and cooled to −20° C. A solution of 2.28 g (33 mmol) sodium nitrite in 20 ml of water is added dropwise. The mixture is stirred for 3 hours at −20° to −10° C., then 27.08 g (120 mmol) tin-(II)-chloride dihydrate in 30 ml hydrochloric acid are added dropwise within 0.25 hours. The reaction mixture is stirred for 2 hours at −10° C., then acidified with cooling. The suspension is suction filtered through kieselguhr and washed with chloroform. The phases of the filtrate are separated, the aqueous phase is extracted with chloroform. The combined organic phases are dried and evaporated to dryness. The residue is precipitated as the hydrochloride, then stirred with diethyl ether.

Yield: 4.02 g (50% of theoretical)

Reagents of General Formula (XV)

Synthesis of the Reagent (XV.1)

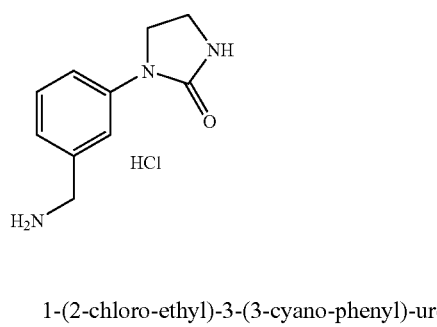

(XV.1)

1-(2-chloro-ethyl)-3-(3-cyano-phenyl)-urea

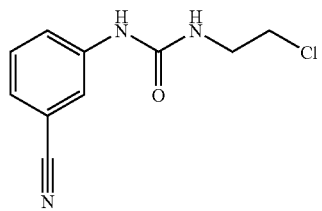

65.00 g (550 mmol) 3-amino-benzonitrile are dissolved in 450 ml dioxane, 56 ml (660 mmol) 1-chloro-2-isocyanato-ethane dissolved in 60 ml dioxane are added dropwise. The reaction mixture is stirred for 3 hours at 60° C. and for 16 hours at ambient temperature. Then the precipitate is suction filtered, washed with diethyl ether and dried.

Yield: 110.00 g (90% of theoretical)

mp: 138°-139° C.

3-(2-oxo-imidazolidin-1-yl)-benzonitrile

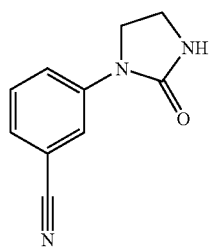

110.00 g (490 mmol) 1-(2-chloro-ethyl)-3-(3-cyano-phenyl)-urea are dissolved in 2000 ml of ethanol at 50° C. and a solution of 42.00 g (640 mmol) potassium hydroxide in 390 ml of ethanol is added within 1.5 hours. The reaction mixture is stirred for 16 hours at ambient temperature, then the precipitate formed is suction filtered, washed with water and dried.

Yield: 68.00 g (75% of theoretical)

mp: 149°-150° C.

1-(3-aminomethyl-phenyl)-imidazolidin-2-one hydrochloride (XV.1)

40.00 g (210 mmol) 3-(2-oxo-imidazolidin-1-yl)-benzonitrile are suspended in 1500 ml of methanol, 53 ml of 37% hydrochloric acid are added. The mixture is hydrogenated for 20 hours at ambient temperature under a pressure of 7 bar with 4.00 g palladium/charcoal. The catalyst is filtered off, the filtrate is concentrated and the precipitate formed is suction filtered, washed with acetone and dried.

Yield: 42.00 g (88% of theoretical)

mp: 238°-239° C.

Synthesis of the Reagent (XV.2)

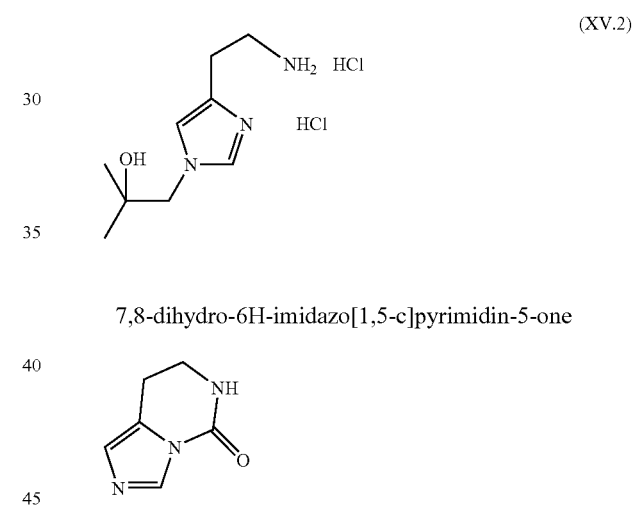

(XV.2)

7,8-dihydro-6H-imidazo[1,5-c]pyrimidin-5-one

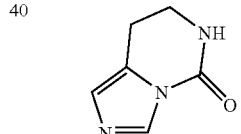

50.00 g (450 mmol) histamine are dissolved in 1500 ml dimethylformamide, 73.87 g (450 mmol) carbonyldiimidazole are added. The reaction mixture is stirred for 5 hours at 70° C. and for 16 hours at ambient temperature. Then the mixture is evaporated down, the residue is extracted hot from acetonitrile.

Yield: 53.73 g (87% of theoretical)

2-(2-methyl-allyl)-5-oxo-5,6,7,8-tetrahydro-imidazo[1,5-c]pyrimidin-2-ium; bromide

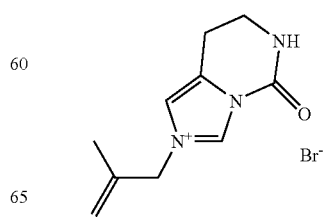

500 mg (4 mmol) 7,8-dihydro-6H-imidazo[1,5-c]pyrimidin-5-one and 1.21 ml (12 mmol) 3-bromo-2-methylpropene are stirred in 5 ml acetonitrile for 72 hours at 85° C. The mixture is evaporated down to the residue.

Yield: 1.14 g (100% of theoretical)

1-[4-(2-amino-ethyl)-imidazol-1-yl]-2-methyl-propan-2-ol dihydrochloride (XV.2)

1.14 g (4 mmol) 2-(2-methyl-allyl)-5-oxo-5,6,7,8-tetrahydro-imidazo[1,5-c]pyrimidin-2-ium; bromide are refluxed in 2 ml (12 mmol) 6 molar hydrochloric acid for 40 hours with stirring. Then the solution is lyophilised.

Yield: 1.15 g (100% of theoretical)

Synthesis of the Reagent (XV.3)

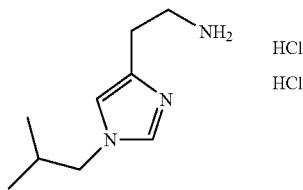

2-isobutyl-5-oxo-5,6,7,8-tetrahydro-imidazo[1,5-c]pyrimidin-2-ium; bromide

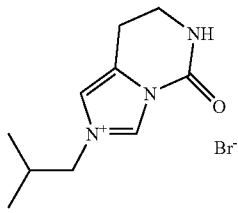

500 mg (2 mmol) 2-(2-methyl-allyl)-5-oxo-5,6,7,8-tetrahydro-imidazo[1,5-c]pyrimidin-2-ium; bromide are placed in 75 ml of methanol, 40 mg palladium/charcoal 10% are added and the mixture is hydrogenated. Then it is evaporated down to the residue.

Yield: 510 mg (100% of theoretical)

2-(1-isobutyl-1H-imidazol-4-yl)-ethylamine (XV.3)

510 mg (2 mmol) 2-isobutyl-5-oxo-5,6,7,8-tetrahydro-imidazo[1,5-c]pyrimidin-2-ium; bromide are refluxed in 1 ml (6 mmol) 6 molar hydrochloric acid for 72 hours with stirring. Then the solution is lyophilised.

Yield: 290 mg (65% of theoretical)

Synthesis of the Reagent (XV.4)

(XV.4)

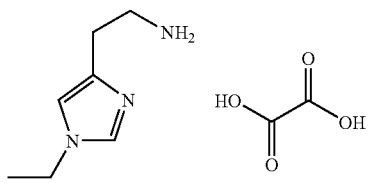

2-ethyl-5-oxo-5,6,7,8-tetrahydro-imidazo[1,5-c]pyrimidin-2-ium; bromide

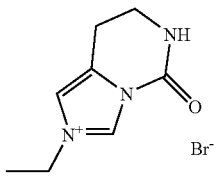

1.00 g (7 mmol) 7,8-dihydro-6H-imidazo[1,5-c]pyrimidin-5-one and 1.57 ml (21 mmol) ethylbromide are stirred in 12 ml acetonitrile for 16 hours at 80° C. After cooling the suspension is suction filtered, washed and dried.

Yield: 1.40 g (78% of theoretical)

2-(1-ethyl-1H-imidazol-4-yl)-ethylamine oxalate (XV.4)

1.16 g (5 mmol) 2-ethyl-5-oxo-5,6,7,8-tetrahydro-imidazo[1,5-c]pyrimidin-2-ium; bromide are refluxed in 7 ml (14 mmol) 2 molar hydrochloric acid for 16 hours with stirring. Then the mixture is evaporated down, the residue is recrystallised from acetonitrile/ethanol. The highly hygroscopic crystals obtained are made neutral and evaporated down. The residue is precipitated as the oxalate and recrystallised from ethanol.

Yield: 1.00 g (93% of theoretical)

Synthesis of the reagent (XV.5)

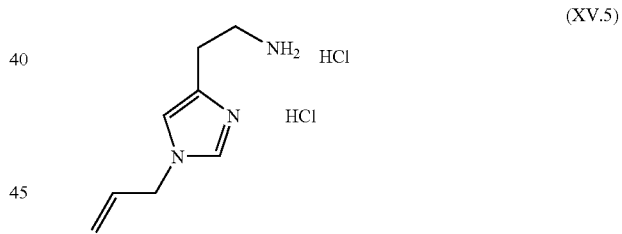

2-allyl-5-oxo-5,6,7,8-tetrahydro-imidazo[1,5-c]pyrimidin-2-ium; bromide

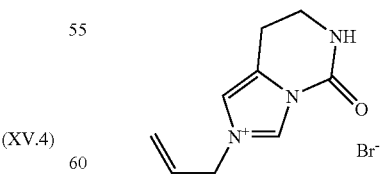

100 mg (729 mmol) 7,8-dihydro-6H-imidazo[1,5-c]pyrimidin-5-one and 189.25 µl (2.19 mmol) allylbromide are stirred in 5 ml acetonitrile for 16 hours at 85° C. After cooling the suspension is suction filtered and dried.

Yield: 113.50 mg (60% of theoretical)

2-(1-allyl-1H-imidazol-4-yl)-ethylamine dichloride (XV.5)

113 mg (438 mmol) 2-allyl-5-oxo-5,6,7,8-tetrahydro-imidazo[1,5-c]pyrimidin-2-ium; bromide are refluxed in 219 µl (1.31 mmol) 6 molar hydrochloric acid for 16 hours with stirring, 0.5 eq hydrochloric acid are added and the mixture is stirred for 16 hours at ambient temperature. Then the solution is lyophilised.
Yield: 110 mg (100% of theoretical)

Synthesis of the Reagent (XV.6)

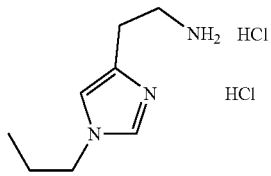
(XV.6)

5-oxo-2-propyl-5,6,7,8-tetrahydro-imidazo[1,5-c] pyrimidin-2-ium; bromide

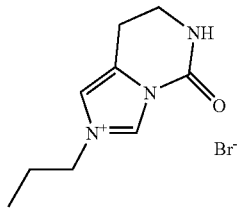

2.00 g (15 mmol) 7,8-dihydro-6H-imidazo[1,5-c]pyrimidin-5-one and 6.83 mmol) (75 mmol) propylbromide are stirred in 20 ml acetonitrile for 72 hours at 85° C. After cooling the suspension is suction filtered, washed and dried.
Yield: 3.48 g 2-(1-propyl-1H-imidazol-4-yl)-ethylamine (XV.6)

100 mg (0.384 mmol) 5-oxo-2-propyl-5,6,7,8-tetrahydro-imidazo[1,5-c]pyrimidin-2-ium; bromide are refluxed in 192 µl (1.15 mmol) 6 molar hydrochloric acid for 16 hours with stirring. Then the solution is lyophilised.
Yield: 81.30 mg (64% of theoretical)

Synthesis of the Reagent (XV.7)

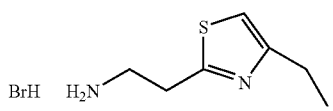
(XV.7)

2-(4-ethyl-thiazol-2-yl)-ethylamine hydrobromide (XV.7)

2.00 g (9.50 mmol) tert.butyl N(3-amino-3-thioxopropyl) carbamate and 1.58 g (10.45 mmol) 1-bromo-2-butanone are refluxed in 40 ml of ethanol for 16 hours with stirring. The reaction mixture is evaporated down, the residue is purified by chromatography.
Yield: 2.00 g (89% of theoretical)

Synthesis of the Reagent (XV.8)

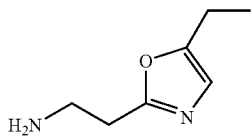
(XV.8)

benzyl [2-(2-hydroxy-butylcarbamoyl)-ethyl]-carbamate

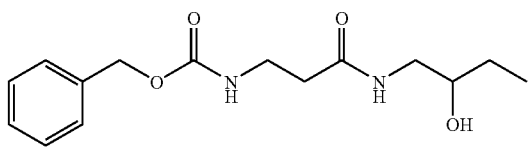

23.20 g (103.93 mmol) 3-benzyloxycarbonylamino-propionic acid, 14.10 g (104.35 mmol) 1-hydroxybenzotriazole, 18.80 ml (135.07 mmol) triethylamine and 21.00 g (135.27 mmol) (ethyl-3-(3-dimethylamino)-propylcarbodiimide hydrochloride (EDAC) are placed in 150 ml dichloromethane, cooled to 0° C. and stirred for 0.75 hours at this temperature. Then 10.50 g (114.26 mmol) 1-amino-2-butanol are added, and the mixture is stirred for 2.5 hours at 0°-5° C. The reaction mixture is extracted with water and 1 molar sodium carbonate solution, the organic phase is dried and evaporated to dryness. The residue is extracted again with dichloromethane and sodium carbonate solution.
Yield: 12.30 g (40% of theoretical)

benzyl [2-(2-oxo-butylcarbamoyl)-ethyl]-carbamate

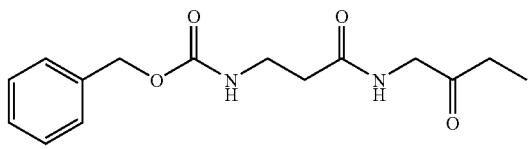

2.20 ml (26.05 mmol) oxalyl chloride are placed in 10 ml dichloromethane, the solution is cooled to −53° C. 2.45 ml (34.49 mmol) dimethylsulphoxide in 5 ml dichloromethane are slowly added dropwise, the mixture is stirred for 0.25 hours, then a solution of 6.30 g (21.40 mmol) benzyl[2-(2-hydroxy-butylcarbamoyl)-ethyl]-carbamate in 30 ml dichloromethane is added. The mixture is stirred for 1.5 hours at −60° C., then 12.60 ml triethylamine are added dropwise. The suspension is stirred for 1 hour at −50° C., then within 16 hours allowed to come up to ambient temperature. The reaction mixture is diluted with dichloromethane, extracted with 1 molar hydrochloric acid, 1 molar sodium carbonate solution and water. The organic phase is dried and evaporated to dryness.
Yield: 5.82 g (93% of theoretical)

benzyl[2-(5-ethyl-oxazol-2-yl)-ethyl]-carbamate

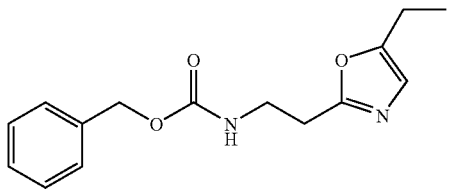

23.07 g (49.60 mmol) PS-triphenylphosphine are in 200 ml dichloromethane suspended, 12.65 g (49.82 mmol) iodine are added. It is stirred for 0.1 hours at ambient temperature, then 13.80 ml (99.28 mmol) triethylamine are added dropwise. 5.80 g (19.84 mmol) benzyl [2-(2-oxo-butylcarbamoyl)-ethyl]-carbamate dissolved in 150 ml dichloromethane are added. The reaction mixture is stirred for 72 hours at ambient temperature, then the precipitate is filtered off. The filtrate is extracted with water, the organic phase is dried and evaporated to dryness.

Yield: 3.35 g (31% of theoretical)

2-(5-ethyl-oxazol-2-yl)-ethylamine (XV.8)

2.86 g (10.43 mmol) benzyl[2-(5-ethyl-oxazol-2-yl)-ethyl]-carbamate are placed in 130 ml of methanol, 0.910 mg palladium/charcoal 10% are added, then the mixture is hydrogenated for 5 hours at ambient temperature under a pressure of 14 psi. Then the catalyst is removed by suction filtering, and the solution is evaporated down.

Yield: 1.45 g (99% of theoretical)

Synthesis of the Reagent (XV.9)

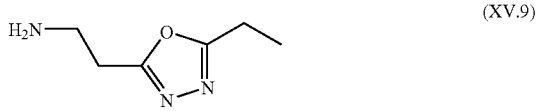

tert-butyl[3-oxo-3-(N'-propionyl-hydrazino)-propyl]-carbamate

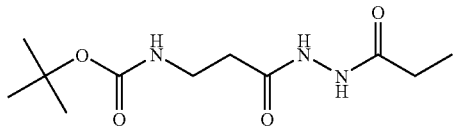

25.00 g (132 mmol) 3-tert-butoxycarbonylamino-propionic acid, 11.45 g (130 mmol) ethanoic hydrazide, 50.91 g (159 mmol) O-(1H-benzotriazol-1-yl)-N,N,N',N'-tetramethyluronium tetrafluoroborate (TBTU) and 50 ml diisopropylethylamine are stirred in 500 ml of tetrahydrofuran/dichloromethane for 24 hours at ambient temperature. Then the mixture is evaporated down, the residue is extracted with ethyl acetate and 10% potassium hydrogen carbonate solution. The organic phase is dried and evaporated to dryness. The residue is crystallised from isopropylether.

Yield: 3.20 g (9% of theoretical)

tert-butyl[2-(5-ethyl-[1,3,4]oxadiazol-2-yl)-ethyl]-carbamate

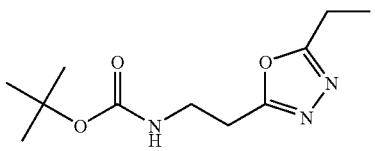

11.49 g (24.70 mmol) PS-triphenylphosphine are placed in 240 ml dichloromethane, 6.27 g (24.70 mmol) iodine are added. The mixture is stirred for 0.1 hours at ambient temperature, then 7.00 ml (50.50 mmol) triethylamine are added dropwise. 3.20 g (12.34 mmol) tert-butyl[3-oxo-3-(N'-propionyl-hydrazino)-propyl]-carbamate dissolved in 150 ml dichloromethane are added. The reaction mixture is stirred for 24 hours at ambient temperature, then the precipitate is filtered off. The filtrate is evaporated down and purified by chromatography.

Yield: 2.95 g (99% of theoretical)

2-(5-ethyl-[1,3,4]oxadiazol-2-yl)-ethylamine (XV.9)

2.95 g (12.23 mmol) tert-butyl[2-(5-ethyl-[1,3,4]oxadiazol-2-yl)-ethyl]-carbamate and 10 ml trifluoroacetic acid are stirred in 100 ml dichloromethane for 24 hours at ambient temperature. Then the mixture is evaporated down, the residue is made basic and extracted with ethyl acetate. The organic phase is dried and evaporated to dryness.

Yield: 0.410 g (24% of theoretical)

Synthesis of the Reagent (XV.10)

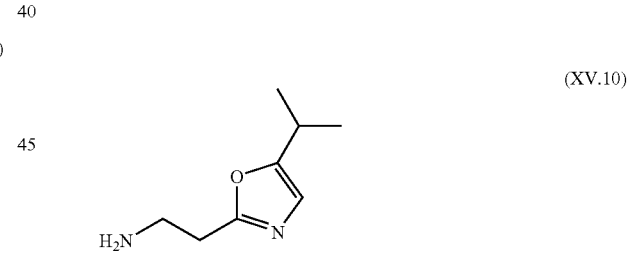

benzyl[2-(2-hydroxy-3-methyl-butylcarbamoyl)-ethyl]-carbamate

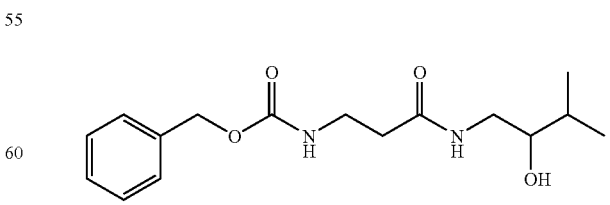

46.00 g (206.07 mmol) 3-benzyloxycarbonylamino-propionic acid, 51.37 g (267.95 mmol) 1-(3-dimethylaminopropyl)-3-ethylcarbodiimide hydrochloride, 27.85 g (206.07 mmol) hydroxybenzotriazole (HOBT) and 37.14 ml (267.95 mmol) triethylamine are placed in 700 ml dichloromethane, the mixture is stirred for 0.5 hours at 0°, then 23.70 g (229.73 mmol) 1-amino-3-methyl-butan-2-ol are added. The reaction mixture is stirred for 16 hours at ambient temperature. Then it is extracted with potassium carbonate solution and dichloromethane. The organic phase is washed with 1 molar sodium hydroxide solution, dried and evaporated to dryness. The residue is stirred with diethyl ether, then recrystallised with acetonitrile.

Yield: 32.40 g (51% of theoretical)

benzyl[2-(3-methyl-2-oxo-butylcarbamoyl)-ethyl]-carbamate

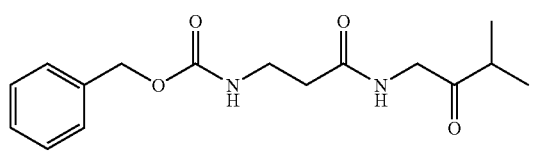

10.81 ml (126.08 mmol) oxalyl chloride are placed in 300 ml dichloromethane, cooled to −70° C. 11.94 ml (168.11 mmol) dimethylsulphoxide are slowly added dropwise. The mixture is stirred for 0.1 hours, then 32.40 g (105.07 mmol) benzyl [2-(2-hydroxy-3-methyl-butylcarbamoyl)-ethyl]-carbamate in 70 ml dichloromethane are added. The mixture is stirred for 1 hour, then 62.48 ml (450.72 mmol) triethylamine are added dropwise. The reaction mixture is stirred for 1.5 hours at −70° C., then slowly allowed to come up to ambient temperature. It is diluted with dichloromethane and washed with 1 molar hydrochloric acid, saturated sodium carbonate solution, water and saturated sodium chloride solution. The organic phase is dried and evaporated to dryness.

Yield: 30.80 g (96% of theoretical)

benzyl[2-(5-isopropyl-oxazol-2-yl)-ethyl]-carbamate

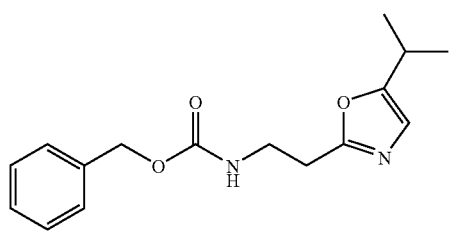

100.00 g (215 mmol) PS-triphenylphosphine are suspended in 1000 ml dichloromethane, 59.92 g (236.06 mmol) iodine are added. The mixture is stirred for 0.1 hours at ambient temperature, then 65.32 ml (470.24 mmol) triethylamine are added dropwise. 28.80 g (94.91 mmol) benzyl [2-(3-methyl-2-oxo-butylcarbamoyl)-ethyl]-carbamate dissolved in 200 ml dichloromethane are added. The reaction mixture is stirred for 16 hours at ambient temperature. As the reaction is incomplete, a further 0.1 eq triphenylphosphine and 0.1 eq iodine are added. The mixture is stirred for 16 hours at ambient temperature, then the precipitate is filtered off. The filtrate is evaporated down, the residue is extracted with water and chloroform, the organic phase is dried and evaporated to dryness. The residue is purified by chromatography.

Yield: 12.50 g (46% of theoretical)

2-(5-isopropyl-oxazol-2-yl)-ethylamine (XV.10)

6.50 g (22.54 mmol) benzyl[2-(5-isopropyl-oxazol-2-yl)-ethyl]-carbamate are placed in 130 ml of methanol, 3.50 g palladium/charcoal 10% are added, then the mixture is hydrogenated for 5 hours at ambient temperature under a pressure of 14 psi. Then the catalyst is removed by suction filtering, the solution is evaporated down. The residue is extracted with dichloromethane and potassium carbonate solution, the organic phase is dried and evaporated to dryness.

Yield: 3.20 g (92% of theoretical)

Synthesis of the Reagent (XV.11)

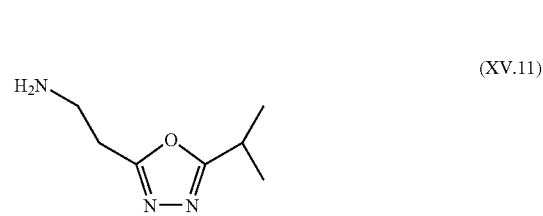

tert-butyl[3-(N'-isobutyryl-hydrazino)-3-oxo-propyl]-carbamate

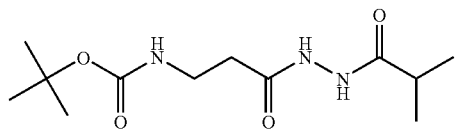

25.00 g (132 mmol) 3-tert-butoxycarbonylamino-propionic acid, 13.50 g (132 mmol) isobutyric acid hydrazide, 50.91 g (159 mmol) O-(1H-benzotriazol-1-yl)-N,N,N',N'-tetramethyluronium tetrafluoroborate (TBTU) and 50 ml diisopropylethylamine are stirred in 500 ml of tetrahydrofuran/dichloromethane for 24 hours at ambient temperature. Then the mixture is evaporated down, the residue is extracted with ethyl acetate and 10% potassium hydrogen carbonate solution. The organic phase is dried and evaporated to dryness. The residue is crystallised from toluene/isopropylether.

Yield: 16.55 g (46% of theoretical)

tert-butyl[2-(5-isopropyl-[1,3,4]oxadiazol-2-yl)-ethyl]-carbamate

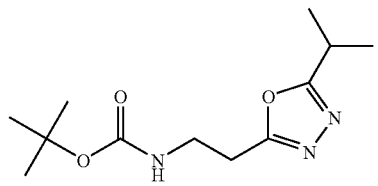

20.00 g (43.00 mmol) PS-triphenylphosphine are placed in 240 ml dichloromethane, 10.88 g (42.87 mmol) iodine are added. The mixture is stirred for 0.1 hours at ambient temperature, then 12.10 ml (87.29 mmol) triethylamine are added dropwise. 5.83 g (21.33 mmol) tert-butyl[3-(N'-isobutyryl-hydrazino)-3-oxo-propyl]-carbamate dissolved in 150 ml dichloromethane are added. The reaction mixture is stirred for 24 hours at ambient temperature, then the precipitate is filtered off. The filtrate is evaporated down and purified by chromatography.

Yield: 5.40 g (99% of theoretical)

2-(5-isopropyl-[1,3,4]oxadiazol-2-yl)-ethylamine (XV.11)

4.00 g (15.67 mmol) tert-butyl[2-(5-isopropyl-[1,3,4]oxadiazol-2-yl)-ethyl]-carbamate and 20 ml trifluoroacetic acid are stirred in 200 ml dichloromethane for 24 hours at ambient temperature. Then the mixture is evaporated down, the residue is made basic and extracted with ethyl acetate. The organic phase is dried and evaporated to dryness.

Yield: 1.440 g (59% of theoretical)

Synthesis of the reagent (XV.12)

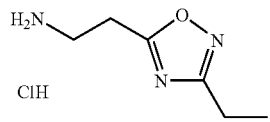

methyl 3-tert-butoxycarbonylamino-propionate

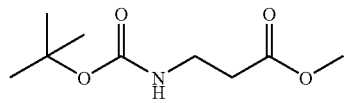

9.90 g (70.93 mmol) β-alaninemethylester hydrochloride are placed in 200 ml acetonitrile, 10 ml (72.14 mmol) triethylamine are added. The mixture is stirred for 0.3 hours at ambient temperature, first 15.48 g (70.93 mmol) Boc-anhydride, then 1.65 g (7.09 mmol) zirconium(IV) chloride are added. The reaction mixture is stirred for 2 hours at ambient temperature, then evaporated down. The residue is extracted with ethyl acetate and water. The organic phase is dried and evaporated to dryness.

Yield: 12.50 g (87% of theoretical)

N-hydroxy-propionamidine

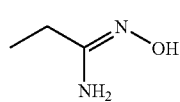

8.00 g (57.88 mmol) potassium carbonate are dissolved in 25 ml of water, 80 ml of ethanol, 4.00 g (57.56 mmol) hydroxylamine and 4.11 ml (57.56 mmol) propionitrile are added. The reaction mixture is stirred for 18 hours at ambient temperature, then evaporated down and re-evaporated with toluene. The residue is mixed with ethanol, suction filtered and the filtrate is evaporated to dryness.

Yield: 3.70 g (73% of theoretical)

tert-butyl[2-(3-ethyl-[1,2,4]oxadiazol-5-yl)-ethyl]-carbamate

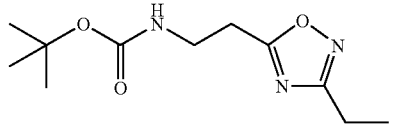

2.00 g (22.70 mmol) N-hydroxy-propionamidine are placed in 10 ml dimethylformamide and molecular sieve. 0.999 g (24.97 mmol) sodium hydride (60% in mineral oil) are added. The mixture is stirred for 0.1 hours at 50° C., then 5.00 g (24.60 mmol) methyl 3-tert-butoxycarbonylamino-propionate in 20 ml dimethylformamide are added. The reaction mixture is stirred for 3 hours at 50° C. After cooling 15 ml of water are added, and the mixture is suction filtered through Celite. The 2 phases of the filtrate are separated, the organic phase is evaporated down. The residue is purified by chromatography.

Yield: 2.05 g (37% of theoretical)

2-(3-ethyl-[1,2,4]oxadiazol-5-yl)-ethylamine hydrochloride (XV.12)

2.05 g (8.50 mmol) tert-butyl[2-(3-ethyl-[1,2,4]oxadiazol-5-yl)-ethyl]-carbamate are placed in 20 ml dichloromethane, 40 ml 1 molar ethereal hydrochloric acid are added. The reaction mixture is stirred for 16 hours at ambient temperature and for 4 hours at 40° C. After the addition of a further 10 ml ethereal hydrochloric acid the mixture is stirred for another 72 hours at ambient temperature. The suspension is evaporated down.

Yield: 1.50 g (99% of theoretical)

Synthesis of the Reagent (XV.13)

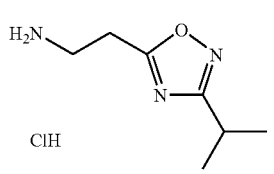

N-hydroxy-isobutyramidine

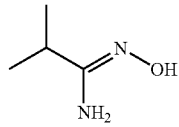

6.00 g (43.41 mmol) potassium carbonate are dissolved in 19 ml of water, 60 ml of ethanol, 3.00 g (43.17 mmol) hydroxylamine and 3.95 ml (43.44 mmol) isobutyronitrile are added. The reaction mixture is stirred for 18 hours at ambient temperature, then evaporated down and re-evaporated with toluene. The residue is mixed with ethanol, suction filtered and the filtrate is evaporated to dryness.

Yield: 3.70 g (84% of theoretical)

tert-butyl[2-(3-isopropyl-[1,2,4]oxadiazol-5-yl)-ethyl]-carbamate

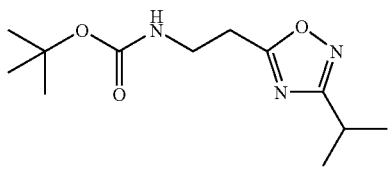

2.20 g (21.54 mmol) N-hydroxy-isobutyramidine are placed in 10 ml dimethylformamide and molecular sieve. 0.948 g (23.69 mmol) sodium hydride (60% in mineral oil) are added. The mixture is stirred for 0.1 hours at 50° C., then 6.20 g (30.51 mmol) methyl 3-tert-butoxycarbonylamino-propionate in 20 ml dimethylformamide are added. The reaction mixture is stirred for 3 hours at 50° C. After cooling 15 ml of water are added, the mixture is suction filtered through Celite. The 2 phases of the filtrate are separated, the aqueous phase is extracted with ethyl acetate, the combined organic phase is evaporated down. The residue is purified by chromatography.

Yield: 0.900 g (16% of theoretical)

2-(3-isopropyl-[1,2,4]oxadiazol-5-yl)-ethylamine hydrochloride (XV.13)

900 mg (3.53 mmol) tert-butyl[2-(3-isopropyl-[1,2,4]oxadiazol-5-yl)-ethyl]-carbamate are placed in 10 ml dichloromethane, 20 ml 1 molar ethereal hydrochloric acid are added. The reaction mixture is stirred for 16 hours at ambient temperature. After the addition of a further 10 ml ethereal hydrochloric acid the mixture is stirred for another 72 hours at ambient temperature and 4 hours at 40° C. The suspension is evaporated down. The residue is dissolved in acetone, mixed with diethyl ether and suction filtered.

Yield: 530 mg (78% of theoretical)

Synthesis of the Reagent (XV.14)

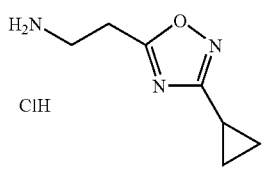

(XV.14)

ethyl 3-tert-butoxycarbonylamino-propionate

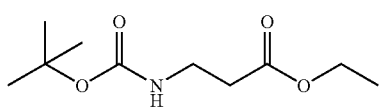

5.00 g (32.55 mmol) β-alanineethylester hydrochloride are placed in 100 ml acetonitrile, 4.75 ml (34.27 mmol) triethylamine are added. The mixture is stirred for 0.3 hours at ambient temperature, first 7.30 g (33.45 mmol) Boc-anhydride, then 0.759 g (3.26 mmol) zirconium(IV) chloride are added. The reaction mixture is stirred for 2 hours at ambient temperature, then evaporated down. The residue is extracted with ethyl acetate and water. The organic phase is dried and evaporated to dryness.

Yield: 7.50 g (100% of theoretical)

N-hydroxy-cyclopropanecarboxamidine

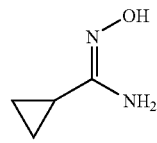

6.00 g (43.41 mmol) potassium carbonate are dissolved in 19 ml of water, 60 ml of ethanol, 3.00 g (43.17 mmol) hydroxylamine and 3.25 ml (43.25 mmol) cyclopropylcyamide are added. The reaction mixture is stirred for 18 hours at ambient temperature, then evaporated down and re-evaporated with toluene. The residue is mixed with ethanol, suction filtered and the filtrate is evaporated to dryness.

Yield: 3.47 g (80% of theoretical)

tert-butyl[2-(3-cyclopropyl-[1,2,4]oxadiazol-5-yl)-ethyl]-carbamate

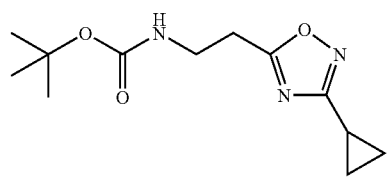

3.10 g (30.96 mmol) N-hydroxy-cyclopropanecarboxamidine are placed in 10 ml dimethylformamide and molecular sieve. 1.32 g (34.06 mmol) sodium hydride (60% in mineral oil) are added. The mixture is stirred for 0.1 hours at 50° C., then 7.40 g (34.06 mmol) ethyl 3-tert-butoxycarbonylamino-propionate in 20 ml dimethylformamide are added. The reaction mixture is stirred for 3 hours at 50° C. After cooling 15 ml of water are added, the mixture is suction filtered through Celite. The 2 phases of the filtrate are separated, the aqueous phase is extracted with ethyl acetate, the combined organic phase is evaporated down. The residue is purified by chromatography.

Yield: 4.00 g (51% of theoretical)

2-(3-cyclopropyl-[1,2,4]oxadiazol-5-yl)-ethylamine hydrochloride (XV.14)

4.00 g (15.79 mmol) tert-butyl[2-(3-cyclopropyl-[1,2,4]oxadiazol-5-yl)-ethyl]-carbamate are placed in 40 ml dichloromethane, 80 ml 1 molar ethereal hydrochloric acid are added. The reaction mixture is stirred for 3 hours at reflux temperature and 72 hours at ambient temperature, then evaporated down. The residue is dissolved in acetone, mixed with diethyl ether and suction filtered.

Yield: 1.30 g (43% of theoretical)

Synthesis of the Reagent (XIX.1)

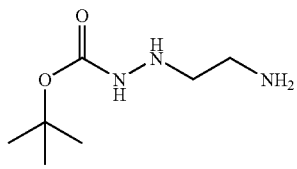

(XIX.1)

butyl N'-[2-(1,3-dioxo-1,3-dihydro-isoindol-2-yl)-ethyl]-hydrazinecarboxylate

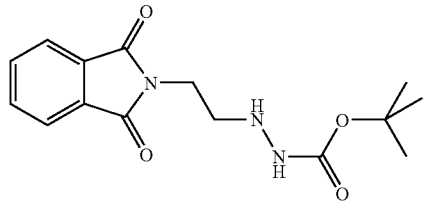

10.00 g (39.36 mmol) N-(2-bromoethyl)-phthalimide and 10.40 g (78.72 mmol) Boc-hydrazine are stirred in 80 ml dimethylformamide for 24 hours at 60° C. Then the mixture is evaporated down, the residue is extracted with ethyl acetate and potassium hydrogen sulphate solution. The organic phase is washed with water, dried and evaporated to dryness. The residue is purified by chromatography.

Yield: 6.20 g (52% of theoretical)

tert-butyl N'-(2-amino-ethyl)-hydrazinecarboxylate (XIX.1)

6.20 g (20.31 mmol) butyl N'-[2-(1,3-dioxo-1,3-dihydro-isoindol-2-yl)-ethyl]-hydrazinecarboxylate are placed in 30 ml of ethanol, 0.985 ml (20.31 mmol) hydrazine hydrate are added. The reaction mixture is refluxed for 1.5 hours with stirring, then cooled to ambient temperature. The precipitate formed is suction filtered, the filtrate is evaporated down. The residue is triturated at 5° C. with 20 ml of 5N acetic acid, then suction filtered. The filtrate is made basic and extracted with ethyl acetate, then saturated with sodium chloride and extracted with methyl-tert. butylether. The resulting organic phase is dried and evaporated to dryness.

Yield: 0.82 g (23% of theoretical)

Synthesis of Intermediate Compounds

Synthesis of intermediate compound (IV)

100 g (0.36 mol) 2-bromo-cyclopentan-1,3-dione (III) (see M. Vanderwalle et al., *Bull. Soc. Chim. Belg.* 1966, 75, 648-654) are dissolved in 370 ml dimethylformamide and combined with 43 g (0.36 mol) N-acetylthiourea (II). The mixture is stirred for 3 hours at 75° C., then at 50° C. 15 g activated charcoal are added. After filtration through kieselguhr the filtrate is cooled to 10° C. and combined with 1200 ml of water. The precipitate formed is stirred for 16 hours at ambient temperature, suction filtered and dried. Yield: 20.4 g (IV) (m.p.: 270-272° C.)

Synthesis of Intermediate Compound (VI.1)

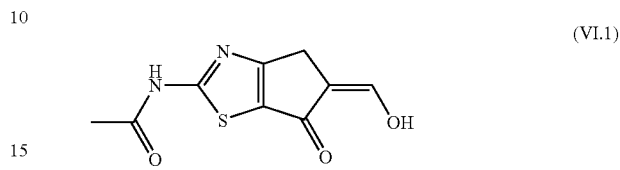

(VI.1)

27.6 g (0.51 mol) sodium methoxide are suspended in 50 ml dimethylformamide and at ambient temperature a suspension of 20.0 g (0.10 mol) (IV) in 350 ml dimethylformamide is added dropwise batchwise within 0.25 hours. The reaction mixture is stirred for 1 hour at ambient temperature, then heated to an internal temperature of 60° C. A solution of 41 ml (0.51 mol) ethyl formate in 40 ml benzene is added dropwise and the mixture is stirred for 2 hours. After cooling to 5° C. 100 ml semiconcentrated hydrochloric acid are added and the mixture is diluted with water to 3000 ml. A precipitate is formed and this is suction filtered. The filtrate is extracted with dichloromethane, the organic phase is dried and evaporated to dryness. The residue is stirred with dichloromethane/diethyl ether 1:5, suction filtered and dried. Yield: 12.3 g (VI.1).

Synthesis of Intermediate Compound (VIII.1)

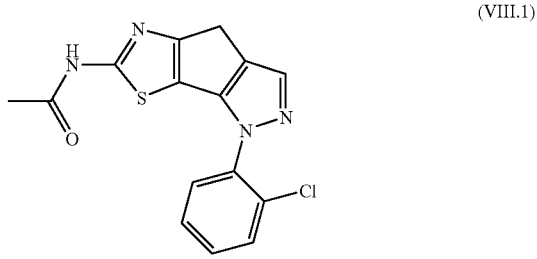

(VIII.1)

500 mg (0.00156 mol) of the intermediate compound (VI.1) are suspended in 8 ml 15 glacial acetic acid, combined with 400 mg (0.00223 mol) 2-chlorophenylhydrazine-hydrochloride. The mixture is stirred for 0.25 hours at 60° C., then cooled to ambient temperature. After the addition of 50 ml of water a precipitate is obtained. This is stirred for 5 minutes at 5° C., suction filtered and dried.

Recrystallisation from methanol.

Yield: 214 mg (=41% of theoretical) of the intermediate compound (VIII.1)

mp: 255°-260° C.

Intermediate compounds (VIII.2) to (VIII.6) and (VIII.7.1) may be prepared analogously using the intermediate compound VI.1 and the appropriate hydrazines.

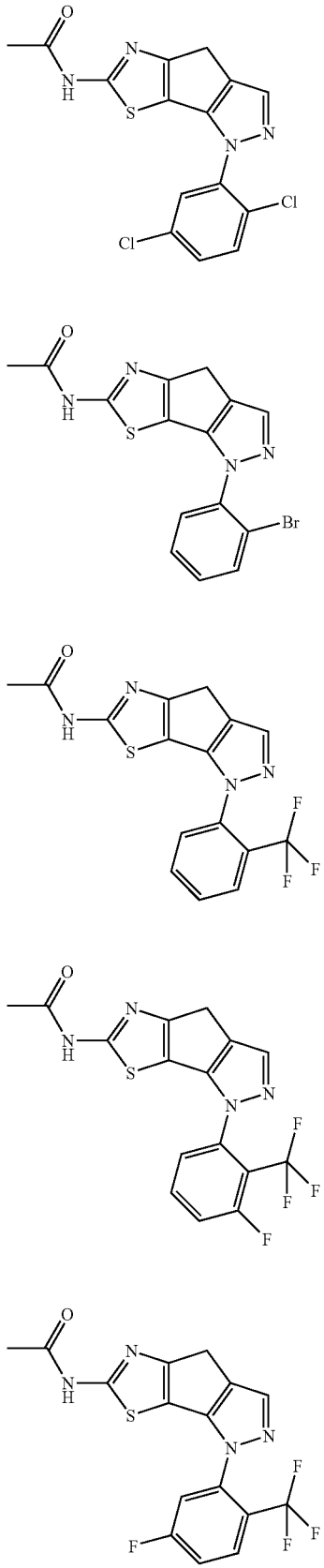

(VIII.2)

(VIII.3)

(VIII.4)

(VIII.5)

(VIII.6)

-continued

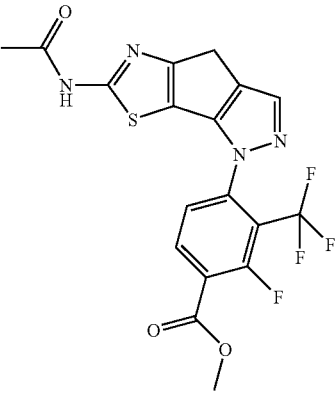

(VIII.7.1)

Synthesis of Intermediate Compound (VIII.7.2)

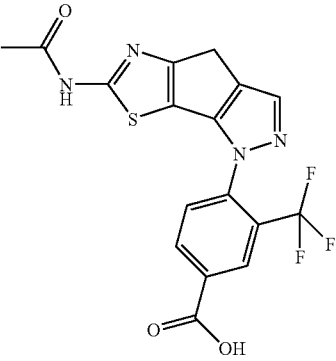

(VIII.7.2)

4.43 g (8.39 mmol) of the intermediate compound (VIII.7.1) are dissolved in 30 ml dichloromethane and 150 ml dioxane, then a solution of 0.603 g (25.17 mmol) lithium hydroxide in 30 ml of water is added. The reaction mixture is stirred for 1 hour at ambient temperature, then evaporated down. The aqueous residue is extracted with ethyl acetate. The aqueous phase is acidified, the precipitate formed is suction filtered and dried.

Yield: 3.69 g (100% of theoretical) of the intermediate compound (VIII.7.2)

Synthesis of Intermediate Compound (VIII.7.3)

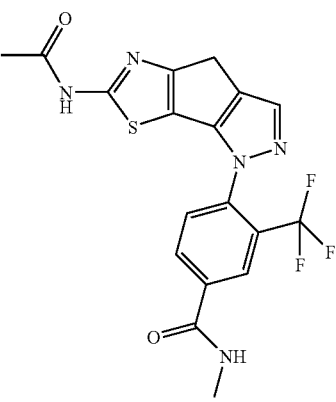

(VIII.7.3)

500 mg (1.22 mmol) of the intermediate compound (VIII.7.2) are placed in 20 ml dimethylformamide, 595.41 mg (3.67 mmol) carbonyldiimidazole are added. The mixture is stirred for 3 hours at ambient temperature, then 3 ml (6 mmol) methylamine are added. The reaction mixture is stirred for 16 hours at ambient temperature. Then it is extracted with water and dichloromethane, the organic phase is dried and evaporated to dryness. The residue is purified by chromatography, corresponding fractions are combined and evaporated down. The product is extracted from acetonitrile/diethyl ether.

Yield: 310 mg (60% of theoretical) of the intermediate compound (VIII.7.3)

HPLC-MS: method B, RT=1.63 min, MH+=422

Synthesis of Intermediate Compound (IX.1)

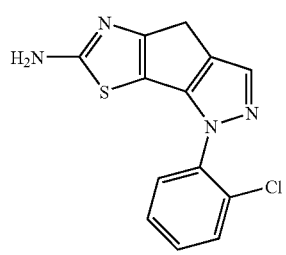
(IX.1)

3.86 g (0.0120 mol) of the intermediate compound (VIII.1) are suspended in 30 ml of water and 30 ml of 32% hydrochloric acid, and the mixture is refluxed for 2 hours with stirring. After cooling to ambient temperature it is extracted with diethyl ether, the aqueous phase is made basic. The precipitate formed is stirred for 0.25 hours at 5° C., suction filtered and dried.

The crude product is suspended in 150 ml of tetrahydrofuran and combined with 3 ml conc. hydrochloric acid, then stirred for 16 hours at 65° C. After cooling to 5° C. the precipitate is suction filtered and dried.

Yield: 2.50 g (=64% of theoretical) intermediate compound (IX.1)

The following intermediate compounds may be prepared analogously using the respective appropriate intermediate compounds (VIII.2) to (VII.6) or (VIII.7.3):

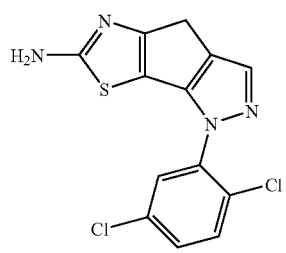
(IX.2)

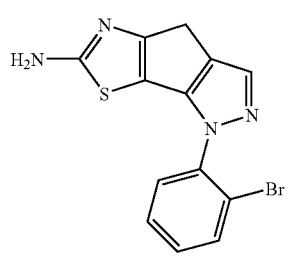
(IX.3)

-continued

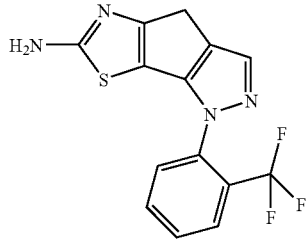
(IX.4)

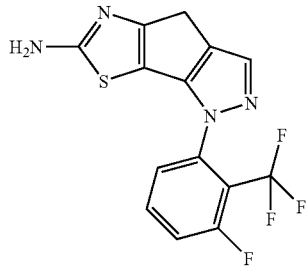
(IX5)

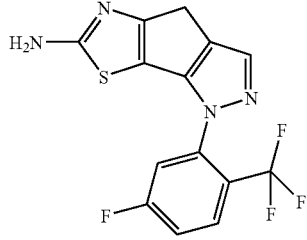
(IX.6)

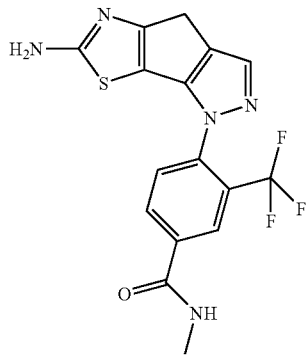
(IX.7)

Alternative Synthesis of Intermediate Compound (IX.4)

11.00 g (30.19 mmol) of the intermediate compound (VIII.4) are placed in 110 ml of tetrahydrofuran, 49.94 ml (905.73 mmol) hydrazine hydrate are added. The reaction mixture is stirred for 16 hours at 60° C. and for 24 hours at ambient temperature. After cooling the reaction mixture is diluted with ethyl acetate and extracted with saturated potassium dihydrogen phosphate solution. The organic phase is dried and evaporated to dryness. The residue is triturated with petroleum ether.

Yield: 6.80 g (70% of theoretical) of the intermediate compound (IX.4)

HPLC-MS: method A, RT=2.37 min, MH+=323

The intermediate compounds (IX.2), (IX.3) and (IX.7) may also be obtained analogously using the intermediate compounds (VIII.2), (VIII.3) and (VIII.7).

Synthesis of Intermediate Compound (XI.1)

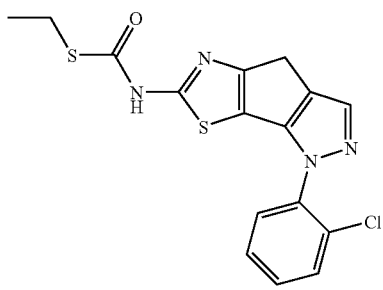
(XI.1)

A suspension of the intermediate compound (IX.1) in 40 ml of pyridine is heated to 50° C. and 0.82 ml (0.00756 mol) ethylchlorothiolformate are added dropwise. The reaction mixture is stirred for 16 hours at an internal temperature of 60° C. After cooling to ambient temperature the reaction mixture is stirred into 400 ml of water, then stirred for 1 hour at 10° C. The precipitate formed is suction filtered and dried.

Yield: 1.42 g of the intermediate compound (XI.1), purity approx. 85%

The following intermediate compounds can be prepared analogously using the respective appropriate intermediate compounds (IX.2) to (IX.6)

(XI.2)

(XI.3)

-continued (XI.4)
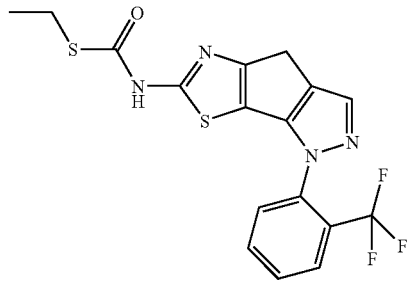

(XI.5)
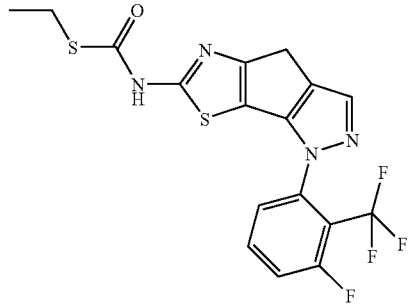

(XI.6)
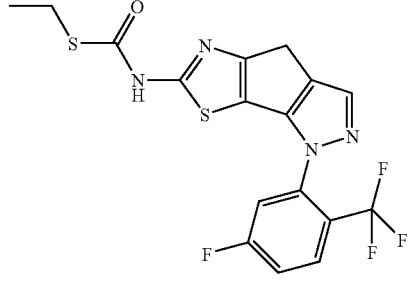

Synthesis of Intermediate Compound (XXI.1)
According to Diagram 2:

(XXI.1)
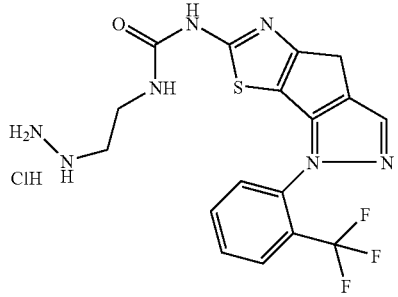

Intermediate Compound (XX.1)

(XX.1)
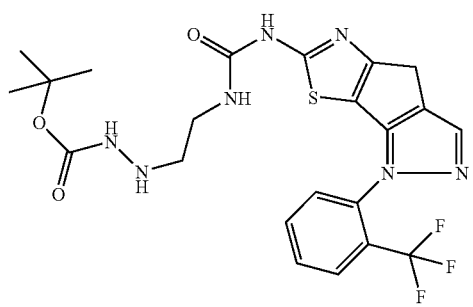

954 mg (2.33 mmol) of intermediate compound (XI.4) and 611 mg (3.49 mmol) tert-butyl N'-(2-amino-ethyl)-hydrazinecarboxylate (XIX.1) are stirred into 8 ml of ethanol for 16 hours at 70° C. Then the mixture is evaporated down and the residue is purified by chromatography.

Yield: 256 mg (21% of theoretical) of the intermediate compound (XX.1)

HPLC-MS: method A, RT=2.70 min, MH+=524

Intermediate compound (XXI.1)

256 mg (0.489 mmol) of the intermediate compound (XX.1) are dissolved in 20 ml diethyl ether and 3 ml dichloromethane, and 2.45 ml (6.54 mmol) 2 molar ethereal hydrochloric acid are added dropwise at ambient temperature. The reaction mixture is stirred for 16 hours at ambient temperature and for 4 hours at 40° C. If the reaction is incomplete a further 0.3 eq of an ethereal hydrochloric acid are added, the mixture is stirred for 2 hours at 40° C. and for 16 hours at ambient temperature. After cooling to 5° C. the suspension is suction filtered, the precipitate is washed with diethyl ether and dried.

Yield: 180 mg (80% of theoretical) of the intermediate compound (XXI.1)

Synthesis of Intermediate Compound (XXVII.1)
According to Diagram 3

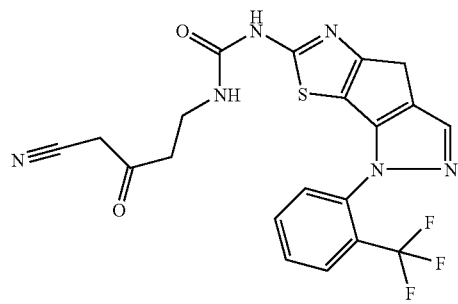

(XXVII.1)

Intermediate Compound (XXVI):

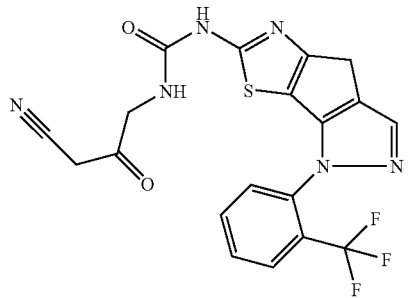

(XXVI.1)

3.00 g (8.75 mmol) of the intermediate compound (IX.4) and 1.73 ml (13.12 mmol) ethyl 3-isocyanato-propionate (XXV.1) are refluxed in 20 ml acetonitrile for 4.5 hours with stirring. Then the resulting suspension is evaporated down and the residue is purified by chromatography (MPLC). Corresponding fractions are combined and evaporated to dryness, extracted from acetonitrile/diethyl ether.

Yield: 3.17 g (78% of theoretical) intermediate compound (XXVI.1)

Intermediate Compound (XXVII.1)

0.36 ml (6.88 mmol) acetonitrile are added to a solution, chilled to −78° C., of 4.30 ml (6.88 mmol) butyllithium solution (1.6 molar in tetrahydrofuran) in 60 ml of tetrahydrofuran, then the mixture is stirred for 1.5 hours at this temperature. Then a solution of 0.800 g (1.72 mmol) of the intermediate compound (XXVI.1) in 15 ml of tetrahydrofuran is added dropwise within 0.2 hours. The reaction mixture is stirred for 1 hour at −70° C. and for 3 hours at −30° C. After the addition of 45 ml of pH7 buffer the mixture is slowly thawed, diluted with tetrahydrofuran and extracted. The organic phase is dried and evaporated to dryness. The residue is purified by chromatography (HPLC), corresponding fractions are lyophilised.

Yield: 0.197 g (24% of theoretical) of the intermediate compound (XXVII.1)

The intermediate compound (XXVII.2) can be prepared analogously using ethyl 3-isocyanato-acetate (XXV.2).

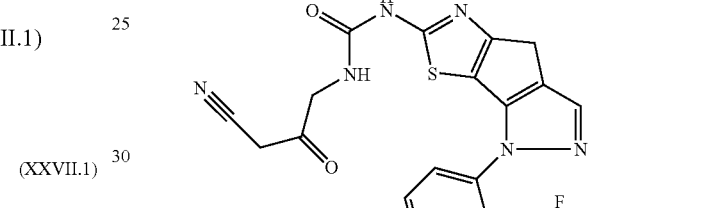

(XXVII.2)

Synthesis of the Compounds of Formula (I)

Methods A and B:

Waters ZMD, Alliance 2690/2695 HPLC, Waters 2700 Autosampler, Waters 996/2996 Diode array detector (wavelength range 210-400 nm).

Stationary phase (column temperature: constant at 25° C.):

Method A: column XTerra®, MS C$_{18}$ 2.5 µm, 4.6 mm×30 mm.

Method B: column Merck Chromolith™ SpeedROD RP-18e, 4.6 mm×50 mm.

Mobile phase: L1: water with 0.10% TFA; L2: acetonitrile with 0.10% TFA flow rates:

Method A: 1.00 mL/min
Method B: 2.00 mL/min

| time (min) | % L1 | % L2 |
|---|---|---|
| 0.0 | 95 | 5 |
| 0.1 | 95 | 5 |
| 3.1 | 2 | 98 |
| 4.5 | 2 | 98 |
| 5.0 | 95 | 5 |

Methods C and D:

Waters ZMD, Alliance 2790/2795 HPLC, Waters 2700 Autosampler, Waters 996/2996 Diode array detector (wavelength range 210-500 nm).

Stationary phase (column temperature: constant at 40° C.): column X-Terra MS C18 4.6×50 mm, 3.5 μm.

Mobile phase: L1: water with 0.10% TFA; L2: acetonitrile with 0.10% TFA flow rates: 1.00 mL/min

| time (min) | % L1 | % L2 |
|---|---|---|
| 0.0 | 95 | 5 |
| 0.1 | 95 | 5 |
| 5.1 | 2 | 98 |
| 6.5 | 2 | 98 |
| 7.0 | 95 | 5 |

The symbol X used in Table A in the structural formula of the substituent is to be understood as being the linkage point to the remainder of the molecule. The substituent replaces the groups $R^a$ and $R^b$ according to the arrangement of the columns.

EXAMPLES

Synthesis of Example 120

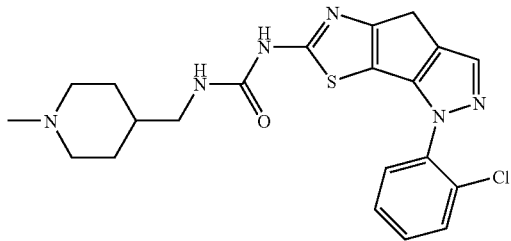

18.84 mg (0.050 mmol) of the intermediate compound (XII.7) and 22.77 mg (0.225 mmol) triethylamine are placed in 1 ml of ethanol, 9.62 mg (0.075 mmol) (1-methyl-piperidin-4-yl)-methylamine in 1 ml of ethanol are added. The reaction mixture is stirred for 16 hours at 70° C. Then the mixture is evaporated down, the residue is purified by chromatography (LCMS). Corresponding fractions are lyophilised.

Yield: 15.70 mg (56% of theoretical)

Examples 119 and 121 to 179 may be prepared analogously.

Synthesis of Example 38

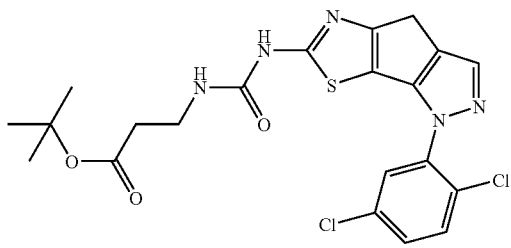

70 mg (0.170 mmol) of the intermediate compound (XI.2) are dissolved in 8 ml of ethanol, and 92.65 mg (0.510 mmol) tert-butyl 3-amino-propionate hydrochloride and 0.087 ml (0.510 mmol) diisopropylethylamine are added. The reaction mixture is stirred for 16 hours at 70° C., then evaporated down. The residue is purified by chromatography. Corresponding fractions are evaporated down and triturated with diethyl ether.

Yield: 20 mg (24% of theoretical)

mp: 275°-282° C.

The following Examples 2-37, 39 and 41-118 may be synthesised analogously using the respective appropriate intermediate products (XI.1) to (XI.7) and the respective appropriate amines (either known from the literature or described under "Synthesis of the reagents"):

Synthesis of Example 223

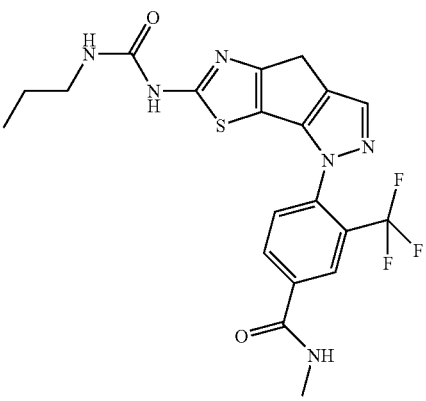

25 mg (0.060 mmol) of the intermediate compound (IX.7) and 58.37 mg (0.360 mmol) carbonyldiimidazole are suspended in 1 ml dioxane and heated to 100° C. for 1.5 hours, then cooled. 30.82 μl (0.180 mmol) diisopropylethylamine and 49.53 μl (0.600 mmol) propylamine in 1 ml of tetrahydrofuran are added. The reaction mixture is stirred for 0.5 hours at ambient temperature. Then it is extracted with water and ethyl acetate, the organic phase is dried and evaporated to dryness. The residue is purified by chromatography.

Yield: 3.7 mg (13% of theoretical)

HPLC-MS: method B, RT=1.76 min, MH+=465

Example 40 may also be prepared analogously using the corresponding amines.

Synthesis of Example 185

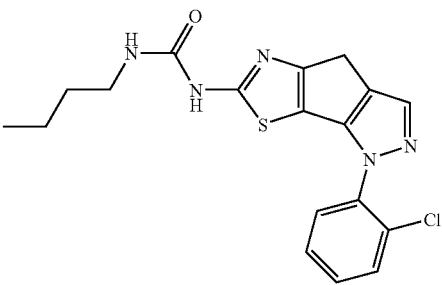

80 mg (0.277 mmol) of the intermediate compound (IX.1) and 0.942 ml (8.34 mmol) 1-isocyanato-butane are stirred in 5 ml acetonitrile for 16 hours at reflux temperature and for 8 hours at ambient temperature. Then the reaction mixture is evaporated down, the residue is triturated with diethyl ether and suction filtered, then purified by chromatography. Corresponding fractions are evaporated down and triturated with acetonitrile.

Yield: 7.4 mg (7% of theoretical)

Examples 180-184 may also be obtained analogously by reacting the respective appropriate intermediate products (IX) with the respective appropriate isocyanates.

Synthesis of Example 186

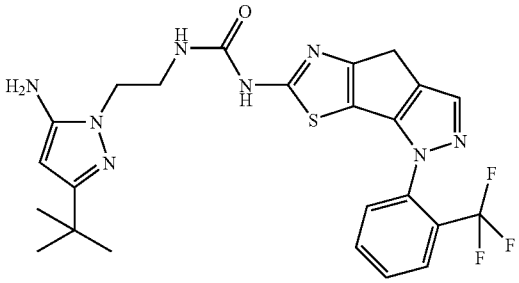

60 mg (0.130 mmol) of the intermediate compound (XXI.1) and 48.82 mg (0.390 mmol) 4,4-dimethyl-3-oxovaleric acid nitrile are stirred in 6 ml of tetrahydrofuran for 16 hours at ambient temperature and for 16 hours at 70° C. Then the mixture is evaporated down, the residue is purified by chromatography. The corresponding fraction is lyophilised.

Yield: 11 mg (16% of theoretical)

HPLC-MS: method A, RT=2.60 min, MH+=531

Example 187 may also be prepared analogously using the suitable beta-ketonitrile.

Synthesis of Example 191

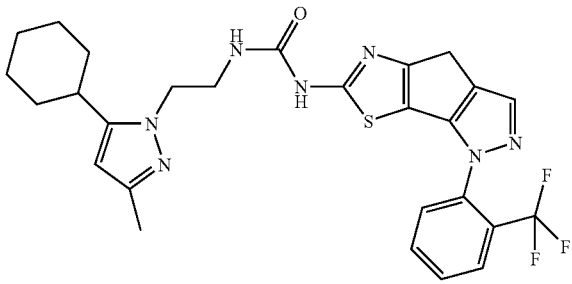

100 mg (0.217 mmol)) of the intermediate compound (XXI.1) and 109.52 mg (0.65 1 mmol) 1-cyclohexyl-butane-1,3-dione are stirred in 8 ml of tetrahydrofuran for 2 hours at ambient temperature, then a catalytic amount of p-toluenesulphonic acid hydrate is added and the mixture is stirred for 16 hours at 60° C. Then the reaction mixture is evaporated down, the residue is purified by chromatography (HPLC-MS). The corresponding fraction is lyophilised.

Yield: 52 mg (43% of theoretical)

HPLC-MS: method A, RT=2.99 min, MH+=556

Examples 188-190 and 192-195 may also be obtained analogously by reacting intermediate compound (XXI.1) with the respective appropriate 1,3-diketo compounds.

Synthesis of Example 197

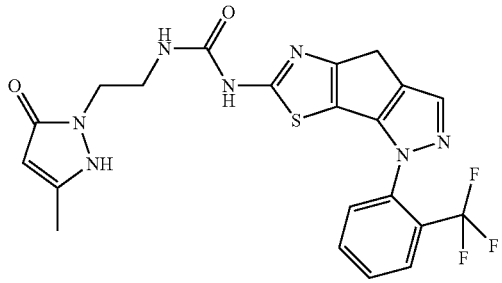

100 mg (0.217 mmol) of the intermediate compound (XXI.1), 0.0702 ml (0.651 mmol) methyl acetoacetate and 50 mg p-toluenesulphonic acid hydrate are stirred in 6 ml of tetrahydrofuran for 1 hour at ambient temperature, for 5 hours at 70° C. and for 72 hours at ambient temperature. Then the mixture is evaporated down, the residue is purified by chromatography (HPLC-MS). The corresponding fraction is lyophilised.

Yield: 30 mg (28% of theoretical)

HPLC-MS: method A, RT=2.44 min, MH+=490

Example 196 may also be prepared analogously by reacting the intermediate compound (XXI.1) with the suitable beta-ketoester.

Synthesis of Example 208

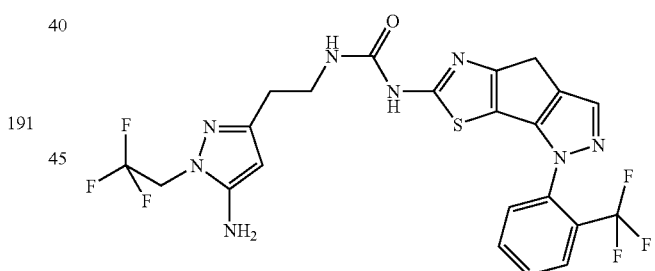

25 mg (0.054 mmol) of the intermediate compound (XXVII.1) and 62 mg (0.544 mmol) (2,2,2-trifluoro-ethyl)-hydrazine are stirred in 3 ml of tetrahydrofuran for 16 hours at ambient temperature. Then the reaction mixture is evaporated down, the residue is purified by chromatography (HPLC-MS). Corresponding fractions are combined and lyophilised.

Yield: 21.4 mg (71% of theoretical)

HPLC-MS: method A, RT=2.56 min, MH+=557

Examples 198-207 and 209-215 may also be obtained analogously by reacting intermediate compound (XXVII.1) with the respective appropriate hydrazines.

Examples 216-222 are obtained analogously by reacting intermediate compound (XXVII.2) with the respective appropriate hydrazines.

Synthesis of Example 1

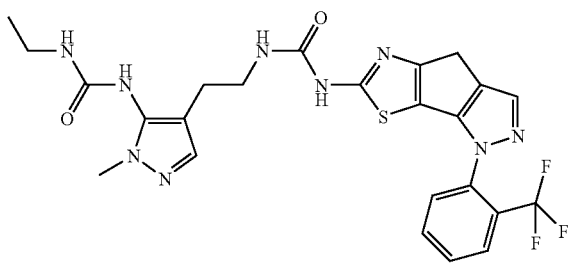

25 mg (0.051 mmol) of Example 198, 30 µl (0.03 mmol) ethylisocyanate and 42 µl (0.31 mmol) triethylamine are stirred in 2 ml of tetrahydrofuran for 2 hours at ambient temperature. The reaction mixture is refluxed for 48 hours with stirring, then evaporated down. The residue is purified by chromatography, corresponding fractions are lyophilised.

Yield: 7.80 mg (27% of theoretical)

HPLC-MS: method A, RT=2.52 min, MH+=560

The following compounds are prepared analogously:

TABLE A (IA)

| Ex. no. | $R^c$ = | $R^a$ | mp [° C.] | HPLC method | RT [min] |
|---|---|---|---|---|---|
| 1 | | | | A | 2.52 |
| 2 | | | | A | 3.02 |
| 3 | | | | B | 1.65 |

TABLE A-continued
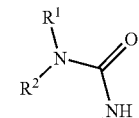
(IA)
| Ex. no. | R<sup>c</sup> = | R<sup>a</sup> | mp [° C.] | HPLC method | RT [min] |
|---|---|---|---|---|---|
| 4 | 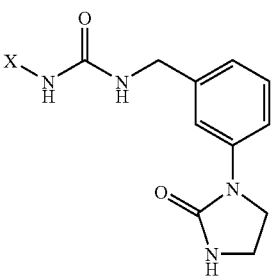 | 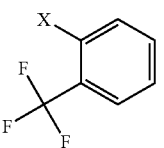 | 245-246 | A | 2.84 |
| 5 | 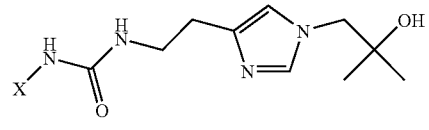 | 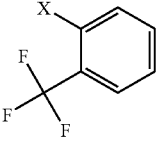 | | B | 1.59 |
| 6 | 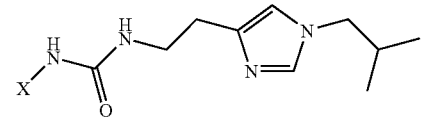 | 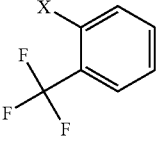 | 230-234 | A | 2.53 |
| 7 | 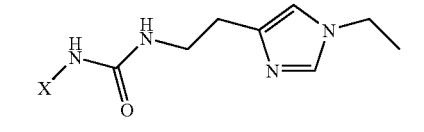 | 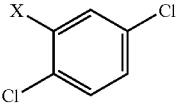 | 242-245 | | |
| 8 | 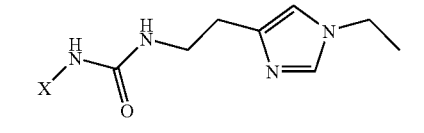 | 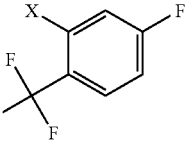 | | A | 2.49 |
| 9 | 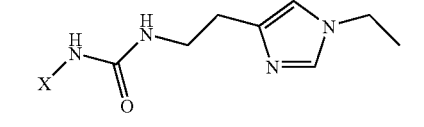 | 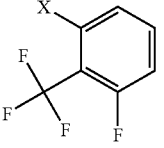 | | B | 1.72 |
| 10 | 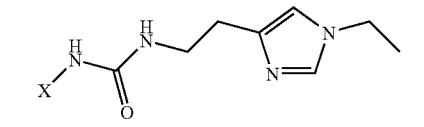 | 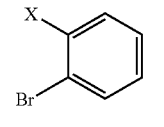 | 184-188 | | |

TABLE A-continued (IA)

| Ex. no. | Rc = | Ra | mp [° C.] | HPLC method | RT [min] |
|---|---|---|---|---|---|
| 11 | ethyl-imidazole-ethyl-NH-C(O)-NH-X | 2-CF3-phenyl-X | 258-263 | A | 2.37 |
| 12 | ethyl-imidazole-ethyl-NH-C(O)-NH-X | 2-Cl-phenyl-X | 229-234 | A | 2.37 |
| 13 | allyl-imidazole-ethyl-NH-C(O)-NH-X | 2-CF3-phenyl-X | | A | 2.39 |
| 14 | propyl-imidazole-ethyl-NH-C(O)-NH-X | 2-Br-phenyl-X | 194-200 | | |
| 15 | propyl-imidazole-ethyl-NH-C(O)-NH-X | 2-CF3-phenyl-X | 254-258 | | |
| 16 | propyl-imidazole-ethyl-NH-C(O)-NH-X | 2-Cl-phenyl-X | 198-201 | | |
| 17 | 4-ethyl-thiazole-ethyl-NH-C(O)-NH-X | 2-CF3-phenyl-X | >300 | | |
| 18 | 5-ethyl-oxazole-ethyl-NH-C(O)-NH-X | 2,5-diCl-phenyl-X | 209-211 | | |

TABLE A-continued (IA)

| Ex. no. | $R^c =$ | $R^a$ | mp [°C.] | HPLC method | RT [min] |
|---|---|---|---|---|---|
| 19 | X-NH-C(O)-NH-CH2CH2-(5-ethyl-oxazol-2-yl) | 2-Br-phenyl (X) | 168-171 | | |
| 20 | X-NH-C(O)-NH-CH2CH2-(5-ethyl-oxazol-2-yl) | 2-CF3-phenyl (X) | 100-110 | | |
| 21 | X-NH-C(O)-NH-CH2CH2-(5-ethyl-oxazol-2-yl) | 2-Cl-phenyl (X) | 110-126 | | |
| 22 | X-NH-C(O)-NH-CH2CH2-(5-ethyl-1,3,4-oxadiazol-2-yl) | 2-CF3-phenyl (X) | | B | 1.81 |
| 23 | X-NH-C(O)-NH-CH2CH2-(5-ethyl-1,3,4-oxadiazol-2-yl) | 2-Cl-phenyl (X) | 166-171 | | |
| 24 | X-NH-C(O)-NH-CH2CH2-(5-isopropyl-oxazol-2-yl) | 2-CF3-phenyl (X) | | | |
| 25 | X-NH-C(O)-NH-CH2CH2-(5-isopropyl-oxazol-2-yl) | 2-Cl-phenyl (X) | 162-165 | | |
| 26 | X-NH-C(O)-NH-CH2CH2-(5-isopropyl-1,3,4-oxadiazol-2-yl) | 2-CF3-phenyl (X) | 270-273 | | |

TABLE A-continued (IA)

| Ex. no. | R^c = | R^a | mp [°C.] | HPLC method | RT [min] |
|---|---|---|---|---|---|
| 27 | ethyl-linked 1,3,4-oxadiazole with isopropyl | 2-Cl-phenyl | 276-278 | | |
| 28 | ethyl-linked 1,2,4-oxadiazole (5-yl) with 3-ethyl | 2-CF₃-phenyl | | | |
| 29 | ethyl-linked 1,2,4-oxadiazole (5-yl) with 3-ethyl | 2-Cl-phenyl | 162-164 | | |
| 30 | ethyl-linked 1,2,4-oxadiazole (5-yl) with 3-isopropyl | 2-CF₃-phenyl | | | |
| 31 | ethyl-linked 1,2,4-oxadiazole (5-yl) with 3-isopropyl | 2-Cl-phenyl | 183-185 | | |
| 32 | ethyl-linked 1,2,4-oxadiazole (5-yl) with 3-cyclopropyl | 2-CF₃-phenyl | 187-193 | | |
| 33 | ethyl-linked 1,2,4-oxadiazole (5-yl) with 3-cyclopropyl | 2-Cl-phenyl | 137-140 | | |

TABLE A-continued (IA)

| Ex. no. | R$^c$ = | R$^a$ | mp [° C.] | HPLC method | RT [min] |
|---|---|---|---|---|---|
| 34 | X-NH-C(O)-NH-ethyl | 2,5-dichlorophenyl | >300 | | |
| 35 | X-NH-C(O)-NH$_2$ | 2,5-dichlorophenyl | >300 | | |
| 36 | X-NH-C(O)-NH-methyl | 2,5-dichlorophenyl | 270-281 | | |
| 37 | X-NH-C(O)-NH-propyl | 2,5-dichlorophenyl | >300 | | |
| 38 | X-NH-C(O)-NH-CH$_2$CH$_2$-C(O)O-tBu | 2,5-dichlorophenyl | 275-282 | | |
| 39 | X-NH-C(O)-NH-CH$_2$-C(O)-N(CH$_3$)$_2$ | 2,5-dichlorophenyl | 283-286 | | |
| 40 | X-NH-C(O)-NH-CH$_2$-(5-cyclopropyl-1H-pyrazol-3-yl) | 2-CF$_3$-4-(N-methylcarbamoyl)phenyl | | A | 2.42 |
| 41 | X-NH-C(O)-NH-propyl | 2-CF$_3$-6-F-phenyl | | A | 3.14 |
| 42 | X-NH-C(O)-NH-methyl | 2-CF$_3$-6-F-phenyl | | B | 1.84 |

TABLE A-continued (IA)

| Ex. no. | R$^c$ = | R$^a$ | mp [° C.] | HPLC method | RT [min] |
|---|---|---|---|---|---|
| 43 | X-NH-C(O)-NH-butyl | 2-CF$_3$, 6-F phenyl | | B | 2.13 |
| 44 | X-NH-C(O)-NH-CH$_2$-cyclopropyl | 2-CF$_3$, 6-F phenyl | | B | 2.05 |
| 45 | X-NH-C(O)-NH-ethyl | 2-CF$_3$, 6-F phenyl | | B | 1.93 |
| 46 | X-NH-C(O)-NH$_2$ | 2-CF$_3$, 6-F phenyl | | B | 1.75 |
| 47 | X-NH-C(O)-NH-CH$_2$-(5-cyclopropyl-1H-pyrazol-3-yl) | 2-CF$_3$, 6-F phenyl | | B | 1.81 |
| 48 | X-NH-C(O)-NH$_2$ | 2-Br phenyl | >300 | | |
| 49 | X-NH-C(O)-N(CH$_3$)$_2$ | 2-Br phenyl | 216-218 | | |
| 50 | X-NH-C(O)-NH-CH$_3$ | 2-Br phenyl | 280-300, | | |

TABLE A-continued (IA)

| Ex. no. | R$^c$ = | R$^a$ | mp [° C.] | HPLC method | RT [min] |
|---|---|---|---|---|---|
| 51 | X-NH-C(O)-NH-Et | 2-Br-phenyl | >230 | | |
| 52 | X-NH-C(O)-NH-CH$_2$CH$_2$-C(O)O-tBu | 2-Br-phenyl | 187-189 | | |
| 53 | X-NH-C(O)-NH-CH$_2$CH$_2$-C(O)O-Et | 2-Br-phenyl | 186-188 | A | 2.88 |
| 54 | X-NH-C(O)-NH-CH$_2$-(5-cyclopropyl-1H-pyrazol-3-yl) | 2-Br-phenyl | | A | 2.57 |
| 55 | X-NH-C(O)-NH-CH$_2$-(1H-tetrazol-5-yl) | 2-Br-phenyl | | B | 1.63 |
| 56 | X-NH-C(O)-NH$_2$ | 2-CF$_3$-phenyl | >300 | | |
| 57 | X-NH-C(O)-NH-Me | 2-CF$_3$-phenyl | 295-299 | | |
| 58 | X-NH-C(O)-N(Me)$_2$ | 2-CF$_3$-phenyl | 255-258 | | |

TABLE A-continued

| Ex. no. | R$^c$ = | R$^a$ | mp [° C.] | HPLC method | RT [min] |
|---|---|---|---|---|---|
| 59 | X-NH-C(O)-NH-Et | 2-CF$_3$-C$_6$H$_4$ | >300 | | |
| 60 | X-NH-C(O)-NH-propyl | 2-CF$_3$-C$_6$H$_4$ | >200 | | |
| 61 | X-NH-C(O)-NH-iPr | 2-CF$_3$-C$_6$H$_4$ | 250-265 | | |
| 62 | X-NH-C(O)-NH-CH$_2$CH$_2$-N(CH$_3$)$_2$ | 2-CF$_3$-C$_6$H$_4$ | 200-203 | | |
| 63 | X-NH-C(O)-NH-CH$_2$CH$_2$-C(O)-O-tBu | 2-CF$_3$-C$_6$H$_4$ | 204-208 | | |
| 64 | X-NH-C(O)-NH-CH$_2$-C(O)-N(CH$_3$)$_2$ | 2-CF$_3$-C$_6$H$_4$ | 247-249 | | |
| 65 | X-NH-C(O)-NH-CH$_2$CH$_2$-OH | 2-CF$_3$-C$_6$H$_4$ | 204-208 | | |

TABLE A-continued

| Ex. no. | R$^c$ = | R$^a$ | mp [°C.] | HPLC method | RT [min] |
|---|---|---|---|---|---|
| 66 | (2-pyrrolidinylmethyl urea, N-Boc) | 2-(trifluoromethyl)phenyl | | | |
| 67 | (2-pyrrolidinylmethyl urea, N-Boc, other enantiomer) | 2-(trifluoromethyl)phenyl | | | |
| 68 | (3-carbamoylbenzyl urea) | 2-(trifluoromethyl)phenyl | | | |
| 69 | ((1-methyl-1H-pyrazol-4-yl)methyl urea) | 2-(trifluoromethyl)phenyl | 199-202 | A | 2.63 |
| 70 | (cyclopropylmethyl urea) | 2-(trifluoromethyl)phenyl | | A | 3.00 |
| 71 | ((1,3-dimethyl-1H-pyrazol-4-yl)methyl urea) | 2-(trifluoromethyl)phenyl | 212-215 | A | 2.55 |

TABLE A-continued

| Ex. no. | R^c = | R^a | mp [°C.] | HPLC method | RT [min] |
|---|---|---|---|---|---|
| 72 | (2-(1H-pyrazol-4-yl)ethyl)urea-X | 2-(trifluoromethyl)phenyl-X | | A | 2.46 |
| 73 | (2-(1-methyl-1H-pyrazol-4-yl)ethyl)urea-X | 2-(trifluoromethyl)phenyl-X | | A | 2.65 |
| 74 | butylurea-X | 2-(trifluoromethyl)phenyl-X | | A | 3.21 |
| 75 | (3-carboxypropyl)urea-X | 2-(trifluoromethyl)phenyl-X | | A | 2.58 |
| 76 | (furan-2-ylmethyl)urea-X | 2-(trifluoromethyl)phenyl-X | | A | 3.08 |
| 77 | (furan-3-ylmethyl)urea-X | 2-(trifluoromethyl)phenyl-X | | A | 3.07 |
| 78 | (thiophen-2-ylmethyl)urea-X | 2-(trifluoromethyl)phenyl-X | | A | 3.18 |

TABLE A-continued

| Ex. no. | R$^c$ = X | R$^a$ | mp [° C.] | HPLC method | RT [min] |
|---|---|---|---|---|---|
| 79 | (urea-CH2-thiophene-CN) | 2-CF3-phenyl | | A | 3.14 |
| 80 | (urea-CH2-3-thienyl) | 2-CF3-phenyl | | A | 3.18 |
| 81 | (urea-CH2-(5-cyclopropyl-pyrazole)) | 2-CF3-phenyl | | A | 2.68 |
| 82 | (urea-CH2-pyrazole) | 2-CF3-phenyl | | B | 1.72 |
| 83 | (urea-CH2-thiazole) | 2-CF3-phenyl | | B | 1.83 |
| 84 | (urea-CH2-(2-phenyl-thiazole)) | 2-CF3-phenyl | | A | 3.40 |
| 85 | (urea-CH2-(furan-2-carboxylic acid ethyl ester)) | 2-CF3-phenyl | | A | 3.16 |

TABLE A-continued
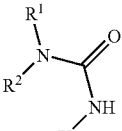
(IA)
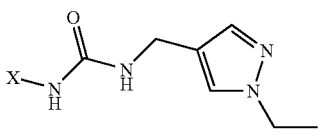
| Ex. no. | $R^c$ = | $R^a$ | mp [°C.] | HPLC method | RT [min] |
|---|---|---|---|---|---|
| 86 | 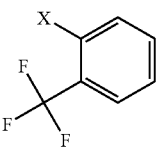 | 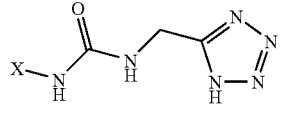 | | B | 1.83 |
| 87 | 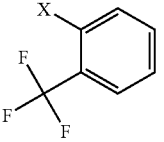 | 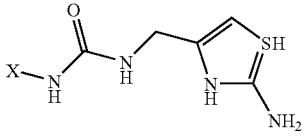 | | A | 2.59 |
| 88 | 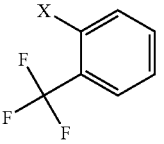 | 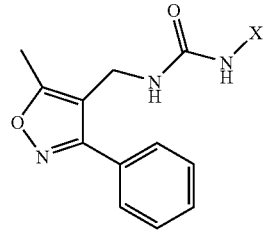 | | A | 2.43 |
| 89 | 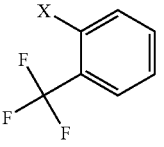 | 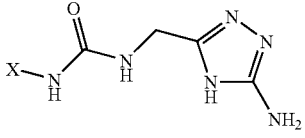 | | A | 3.31 |
| 90 | 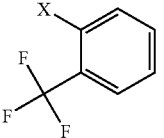 | 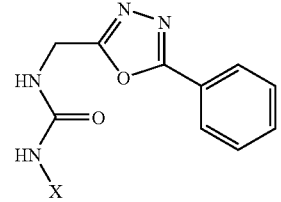 | | A | 2.37 |
| 91 | 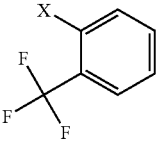 | | | B | 1.98 |

TABLE A-continued
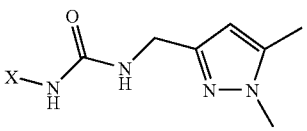
(IA)
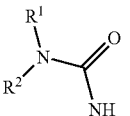
| Ex. no. | R$^c$ = | R$^a$ | mp [°C.] | HPLC method | RT [min] |
|---|---|---|---|---|---|
| 92 | 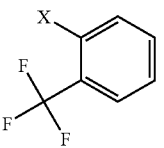 | 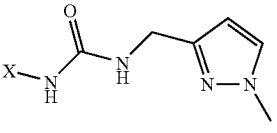 | | B | 1.80 |
| 93 | 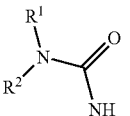 | 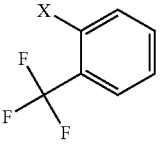 | | A | 2.75 |
| 94 | 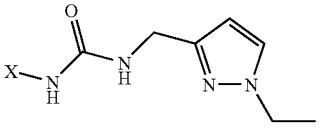 | 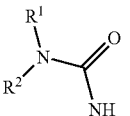 | | B | 1.86 |
| 95 | 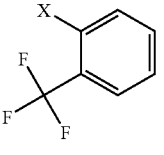 | 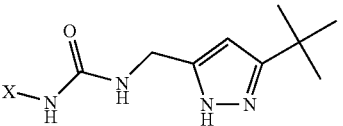 | | A | 2.78 |
| 96 | 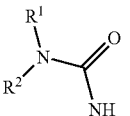 | 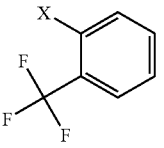 | | B | 1.80 |
| 97 | 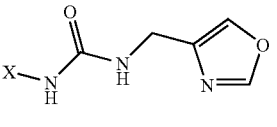 | 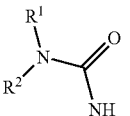 | | A | 2.98 |
| 98 | 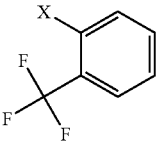 | 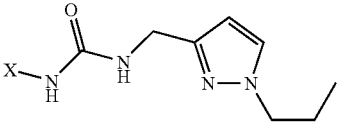 | | A | 2.57 |

TABLE A-continued (IA)

| Ex. no. | R$^c$ = | R$^a$ | mp [° C.] | HPLC method | RT [min] |
|---|---|---|---|---|---|
| 99 | (N-methyl-N-((1-methyl-1H-pyrazol-4-yl)methyl) urea, X-NH-C(O)-) | 2-(trifluoromethyl)phenyl | | A | 2.79 |
| 100 | (N-methyl-N-(furan-2-ylmethyl) urea) | 2-(trifluoromethyl)phenyl | | B | 2.05 |
| 101 | (N-methyl-N-(thiophen-2-ylmethyl) urea) | 2-(trifluoromethyl)phenyl | | B | 2.13 |
| 102 | (N-(pyridin-2-ylmethyl) urea) | 2-(trifluoromethyl)phenyl | | B | 1.63 |
| 103 | (N-(pyridin-3-ylmethyl) urea) | 2-(trifluoromethyl)phenyl | | B | 1.62 |
| 104 | (N-(pyridin-4-ylmethyl) urea) | 2-(trifluoromethyl)phenyl | | B | 1.63 |
| 105 | (N-benzyl urea) | 2-(trifluoromethyl)phenyl | | B | 2.07 |
| 106 | (N-propyl urea) | 2-chlorophenyl | 207-209 | | |

TABLE A-continued
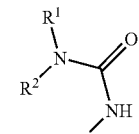
(IA)
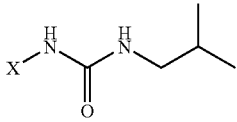
| Ex. no. | $R^c$ = | $R^a$ | mp [° C.] | HPLC method | RT [min] |
|---|---|---|---|---|---|
| 107 | 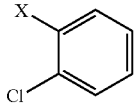 | 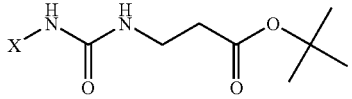 | 202-206 | | |
| 108 | 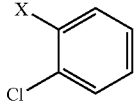 | 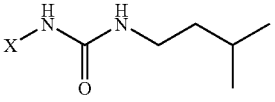 | 191-193 | | |
| 109 | 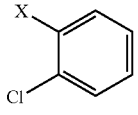 | 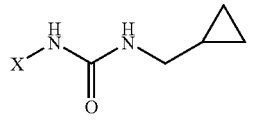 | | | |
| 110 | 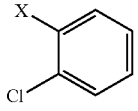 | 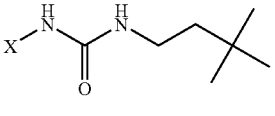 | 220-243 | | |
| 111 | 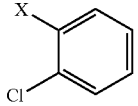 | 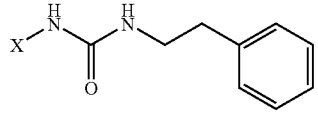 | | | |
| 112 | 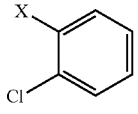 | 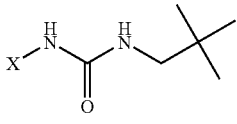 | 156-169 | | |
| 113 | 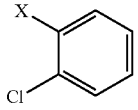 | 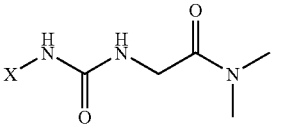 | | | |
| 114 | 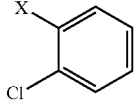 | 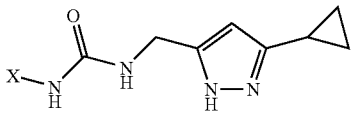 | | | |
| 115 | 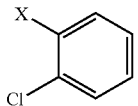 | | | A | 2.59 |

TABLE A-continued (IA)

| Ex. no. | R$^c$ = | R$^a$ | mp [°C.] | HPLC method | RT [min] |
|---|---|---|---|---|---|
| 116 | (urea-CH2-tetrazole) | 2-Cl-phenyl | | B | 1.64 |
| 117 | (urea-CH2CH2-pyrrolidine) | 2-Br-phenyl | 206-212 | | |
| 118 | (urea-CH2CH2-morpholine) | 2-Br-phenyl | 132-135 | | |
| 119 | (urea-C(CH3)2-dihydroquinoxalinone) | 2-Cl-phenyl | | C | 4.28 |
| 120 | (urea-CH2-(1-methylpiperidin-4-yl)) | 2-Cl-phenyl | | C | 3.27 |
| 121 | (N-acyl 2-ethyl-2,7-diazaspiro[4.4]nonane) | 2-Cl-phenyl | | C | 3.32 |
| 122 | (N-acyl hydroxy-methyl-diazaspiro piperidine) | 2-Cl-phenyl | | C | 3.31 |

TABLE A-continued
(IA)
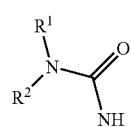
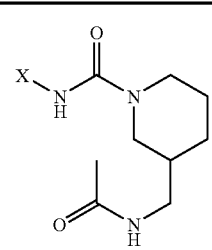
| Ex. no. | R$^c$ = | R$^a$ | mp [° C.] | HPLC method | RT [min] |
|---|---|---|---|---|---|
| 123 | 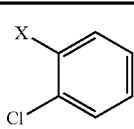 | 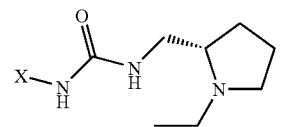 | | C | 3.87 |
| 124 | 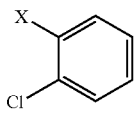 | 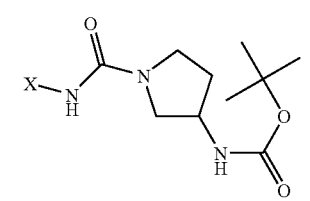 | | C | 3.37 |
| 125 | 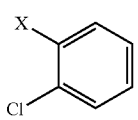 | 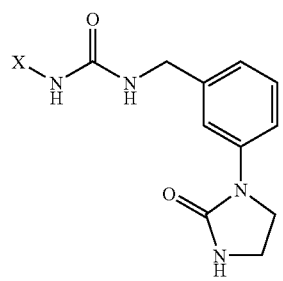 | | C | 4.45 |
| 126 | 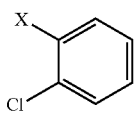 | 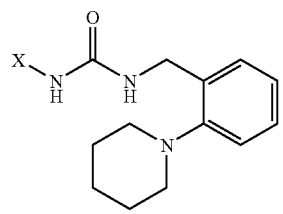 | | C | 4.07 |
| 127 | 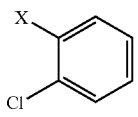 | | | C | 3.81 |

TABLE A-continued

| Ex. no. | R$^c$ = | R$^a$ | mp [°C.] | HPLC method | RT [min] |
|---|---|---|---|---|---|
| 128 | | 2-Cl-C$_6$H$_4$ | | C | 4.58 |
| 129 | | 2-Cl-C$_6$H$_4$ | | C | 3.64 |
| 130 | | 2-Cl-C$_6$H$_4$ | | C | 3.67 |
| 131 | | 2-Cl-C$_6$H$_4$ | | C | 4.71 |
| 132 | | 2-Cl-C$_6$H$_4$ | | C | 4.77 |

TABLE A-continued

| Ex. no. | R$^c$ = X | R$^a$ | mp [°C.] | HPLC method | RT [min] |
|---|---|---|---|---|---|
| 133 | | 2-Cl-C$_6$H$_4$ | | C | 4.75 |
| 134 | | 2-Cl-C$_6$H$_4$ | | C | 4.77 |
| 135 | | 2-Cl-C$_6$H$_4$ | | C | 4.78 |
| 136 | | 2-Cl-C$_6$H$_4$ | | C | 4.43 |
| 137 | | 2-Cl-C$_6$H$_4$ | | C | 4.51 |
| 138 | | 2-Cl-C$_6$H$_4$ | | C | 4.74 |

TABLE A-continued (IA)

| Ex. no. | $R^c =$ | $R^a$ | mp [° C.] | HPLC method | RT [min] |
|---|---|---|---|---|---|
| 139 | (1-ethylpyrrolidin-2-yl)methyl urea | 2-chlorophenyl | | C | 3.37 |
| 140 | 2-(Boc-aminomethyl)phenyl urea | 2-chlorophenyl | | C | 4.96 |
| 141 | 2-((2-oxoimidazolidin-1-yl)methyl)phenyl urea | 2-chlorophenyl | | C | 4.41 |
| 142 | (1-(4-methylbenzyl)-5-oxopyrrolidin-3-yl)methyl urea | 2-chlorophenyl | | C | 4.38 |
| 143 | 1-phenyl-4-oxo-1,3,8-triazaspiro[4.5]decane-8-carboxamide | 2-chlorophenyl | | C | 4.46 |

TABLE A-continued
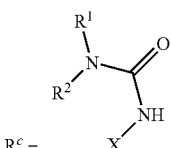
(IA)
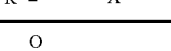
| Ex. no. | R$^c$ = | R$^a$ | mp [° C.] | HPLC method | RT [min] |
|---|---|---|---|---|---|
| 144 | 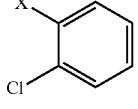 | 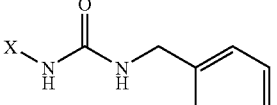 | | C | 4.81 |
| 145 | 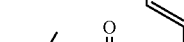 | 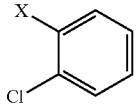 | | C | 4.72 |
| 146 | 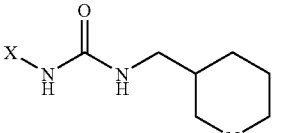 |  | | C | 4.85 |
| 147 | 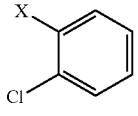 | 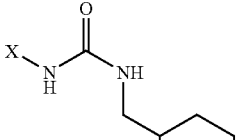 | | C | 4.86 |
| 148 |  | 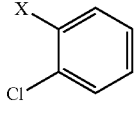 | | C | 3.78 |

TABLE A-continued

| Ex. no. | R^c = | R^a | mp [° C.] | HPLC method | RT [min] |
|---|---|---|---|---|---|
| 149 | (pyrrolidine-2-carboxylic acid, 3-phenyl, N-carboxamide) | 2-Cl-phenyl | | C | 4.36 |
| 150 | (benzyl urea with 4-(2-oxoimidazolidin-1-ylmethyl)) | 2-Cl-phenyl | | C | 4.01 |
| 151 | (pyrrolidine-carboxamide with 3,4-dihydroquinazolin-2(1H)-one) | 2-Cl-phenyl | | C | 4.3 |
| 152 | (urea-ethyl-1-methylpyrrole) | 2-Cl-phenyl | | C | 4.45 |
| 153 | (piperidine-1-carboxamide, 4-hydroxy, 4-(tert-butoxycarbonylmethyl)) | 2-Cl-phenyl | | C | 4.56 |
| 154 | (benzyl urea with 5,5-dimethylhydantoin) | 2-Cl-phenyl | | D | 3.91 |

TABLE A-continued
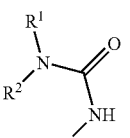
(IA)
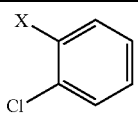
| Ex. no. | R^c = | R^a | mp [° C.] | HPLC method | RT [min] |
|---|---|---|---|---|---|
| 155 | 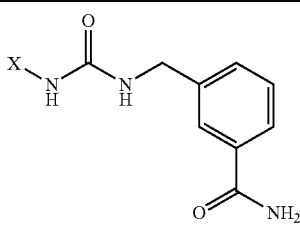 | 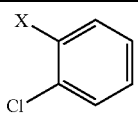 | | C | 3.84 |
| 156 | 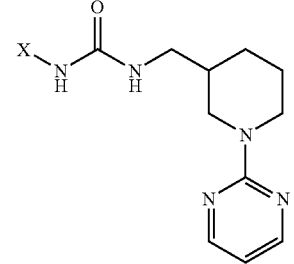 | 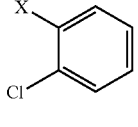 | | C | 3.76 |
| 157 | 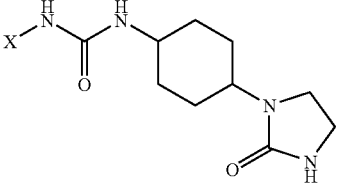 | 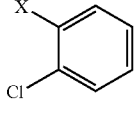 | | C | 3.92 |
| 158 | 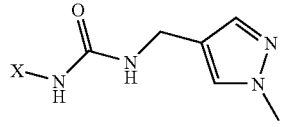 | 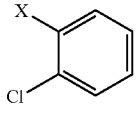 | | C | 3.77 |
| 159 | 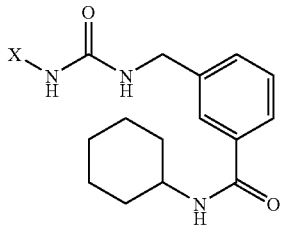 | 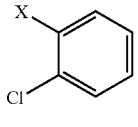 | | C | 4.69 |
| 160 | 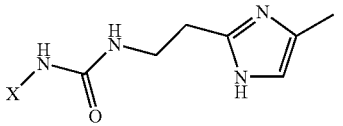 | 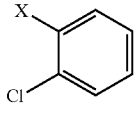 | | C | 3.28 |

TABLE A-continued (IA)

| Ex. no. | R$^c$ = X | R$^a$ | mp [° C.] | HPLC method | RT [min] |
|---|---|---|---|---|---|
| 161 | (pyrrolidine-1-carboxamide with 3-acetamido) | 2-chlorophenyl | | C | 3.6 |
| 162 | (pyrrolidine-1-carboxamide with 3-(2-methoxyphenyl)) | 2-chlorophenyl | | C | 5.02 |
| 163 | (urea linked to 3-amino-2-phenyl-6-oxopiperidine) | 2-chlorophenyl | | C | 3.98 |
| 164 | (urea-CH2-cyclohexyl-NH-Boc) | 2-chlorophenyl | | C | 4.8 |
| 165 | (urea linked to 5-amino-2-oxopiperidine) | 2-chlorophenyl | | C | 3.53 |

TABLE A-continued

| Ex. no. | R$^c$ = | R$^a$ | mp [°C.] | HPLC method | RT [min] |
|---|---|---|---|---|---|
| 166 | (3-{[(tert-butoxycarbonyl)amino]}phenyl)ethyl urea derivative | 2-Cl-phenyl | | C | 4.91 |
| 167 | 2-methyl-2-{[4-(tert-butyl)phenyl]amino methyl} urea derivative | 2-Cl-phenyl | | C | 4.51 |
| 168 | 3-(2-oxoimidazolidin-1-yl)propyl urea derivative | 2-Cl-phenyl | | C | 3.69 |
| 169 | 4-(1H-benzimidazol-1-yl)piperidine-1-carboxamide | 2-Cl-phenyl | | C | 3.62 |
| 170 | 2-(pyridin-2-yl)ethyl urea | 2-Cl-phenyl | | C | 3.25 |
| 171 | 2-(pyridin-3-yl)ethyl urea | 2-Cl-phenyl | | C | 3.26 |

TABLE A-continued
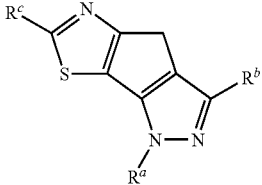
(IA)
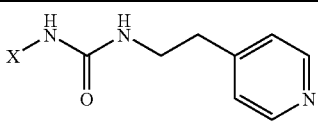
| Ex. no. | R^c = | R^a | mp [°C.] | HPLC method | RT [min] |
|---|---|---|---|---|---|
| 172 | 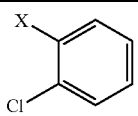 | 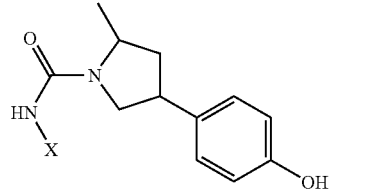 | | C | 3.26 |
| 173 | 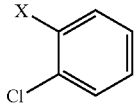 | 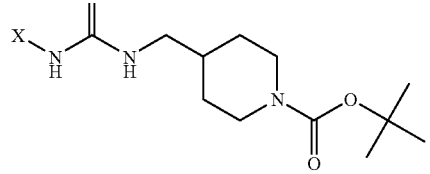 | | D | 4.29 |
| 174 | 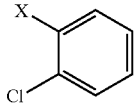 | 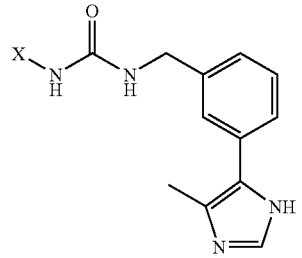 | | C | 4.8 |
| 175 | 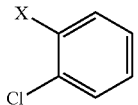 | 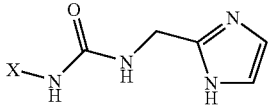 | | C | 3.61 |
| 176 | 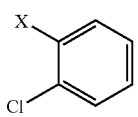 | 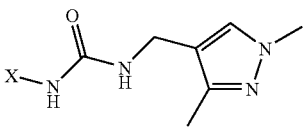 | | C | 3.16 |
| 177 | 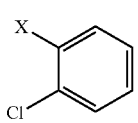 | 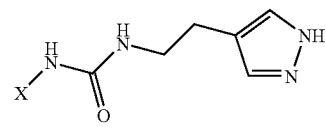 | | C | 3.7 |
| 178 | 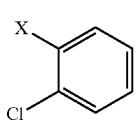 |  | | C | 3.51 |

TABLE A-continued
(IA)
| Ex. no. | R$^c$ = | R$^a$ | mp [° C.] | HPLC method | RT [min] |
|---|---|---|---|---|---|
| 179 | 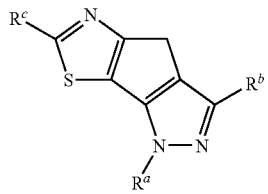 | 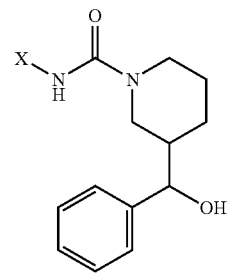 | | D | 4.36 |
| 180 | 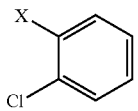 | 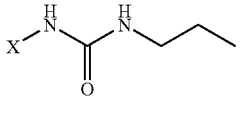 | 275-283 | | |
| 181 | 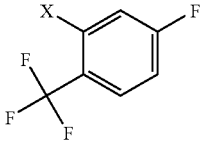 | 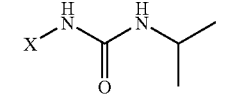 | >300 | | |
| 182 | 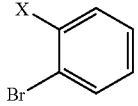 | 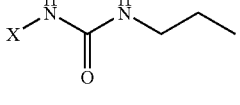 | 219-222 | | |
| 183 | 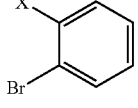 | 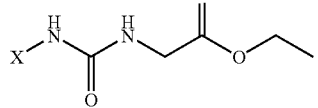 | 195-197 | A | 2.96 |
| 184 |  | 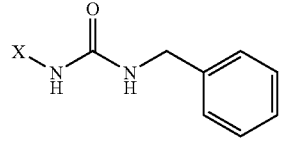 | 200-210 | | |
| 185 | 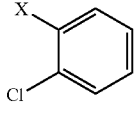 | 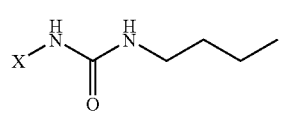 | | | |

TABLE A-continued
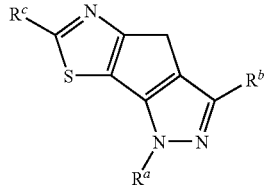
(IA)
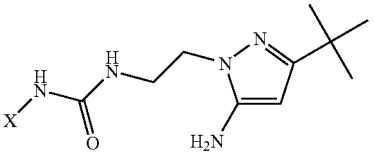
| Ex. no. | R$^c$ = | R$^a$ | mp [° C.] | HPLC method | RT [min] |
|---|---|---|---|---|---|
| 186 | 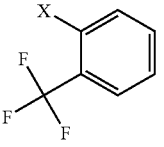 | 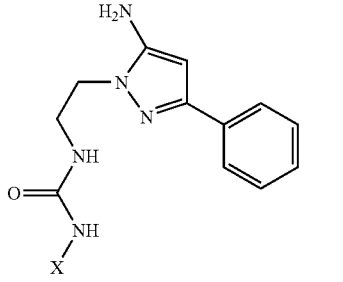 | | A | 2.60 |
| 187 | 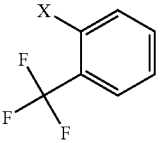 | 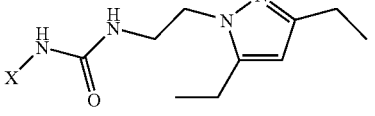 | | A | 2.67 |
| 188 | 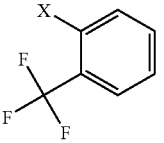 | 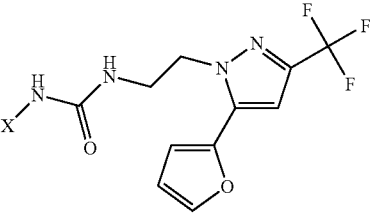 | | B | 1.84 |
| 189 | 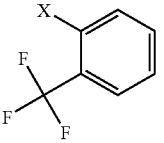 | 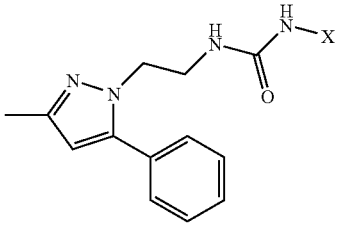 | | A | 3.42 |
| 190 | 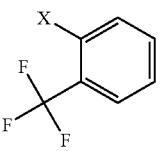 | | | A | 3.08 |

TABLE A-continued
(IA)
| Ex. no. | R$^c$ = | R$^a$ | mp [° C.] | HPLC method | RT [min] |
|---|---|---|---|---|---|
| 191 | 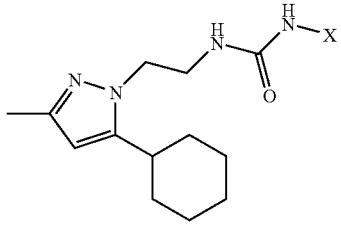 | 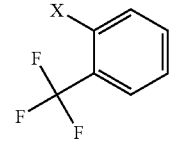 | | A | 2.99 |
| 192 | 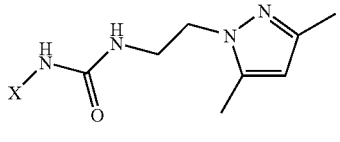 | 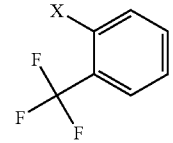 | | A | 2.56 |
| 193 | 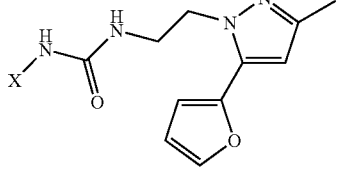 | 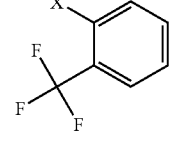 | | B | 2.03 |
| 194 | 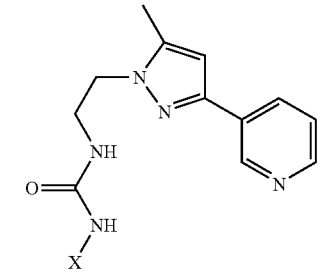 | 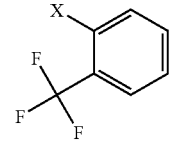 | | B | 1.71 |
| 195 | 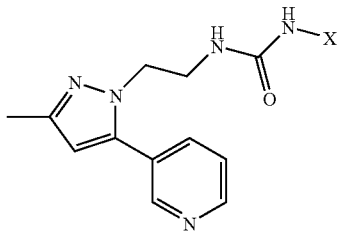 | 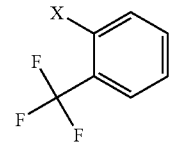 | | B | 1.67 |

TABLE A-continued
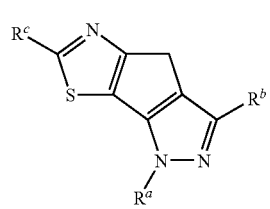
(IA)
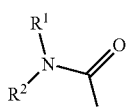
| Ex. no. | R<sup>c</sup> = | R<sup>a</sup> | mp [° C.] | HPLC method | RT [min] |
|---|---|---|---|---|---|
| 196 | | | | A | 2.50 |
| 197 | | | | A | 2.44 |
| 198 | | | | | |
| 199 | | | | A | 2.46 |
| 200 | | | | A | 2.42 |
| 201 | | | | A | 2.34 |
| 202 | | | | A | 2.45 |

TABLE A-continued (IA)

| Ex. no. | R$^c$ = X | R$^a$ | mp [° C.] | HPLC method | RT [min] |
|---|---|---|---|---|---|
| 203 | | | | A | 2.42 |
| 204 | | | | A | 2.50 |
| 205 | | | | A | 2.47 |
| 206 | | | | A | 2.48 |
| 207 | | | | B | 1.75 |
| 208 | | | | A | 2.56 |

TABLE A-continued (IA)

| Ex. no. | $R^c =$ | $R^a$ | mp [° C.] | HPLC method | RT [min] |
|---|---|---|---|---|---|
| 209 | | | | A | 2.50 |
| 210 | | | | A | 2.40 |
| 211 | | | | A | 2.61 |
| 212 | | | | A | 2.41 |
| 213 | | | 212-215 | A | 2.62 |

TABLE A-continued (IA)

| Ex. no. | R$^c$ = | R$^a$ | mp [° C.] | HPLC method | RT [min] |
|---|---|---|---|---|---|
| 214 | | | | A | 2.63 |
| 215 | | | | A | 2.48 |
| 216 | | | | A | 2.62 |
| 217 | | | | A | 2.43 |
| 218 | | | | B | 1.72 |

TABLE A-continued

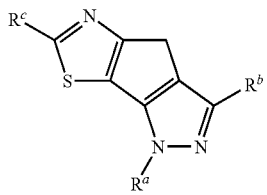

(IA)

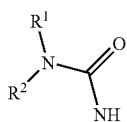

| Ex. no. | $R^c$ = | X | $R^a$ | mp [° C.] | HPLC method | RT [min] |
|---|---|---|---|---|---|---|
| 219 | (pyrazole with NH2, t-Bu, CH2-NH-C(O)-NH-X) | | 2-CF3-phenyl | | B | 1.74 |
| 220 | (pyrazole with NH2, phenyl, CH2-NH-C(O)-NH-X) | | 2-CF3-phenyl | | B | 1.79 |
| 221 | (pyrazole with NH2, NH, CH2-NH-C(O)-NH-X) | | 2-CF3-phenyl | | B | 1.62 |
| 222 | (pyrazole with NH2, ethyl, CH2-NH-C(O)-NH-X) | | 2-CF3-phenyl | | A | 2.48 |
| 223 | X-NH-C(O)-NH-propyl | | 4-X-3-CF3-benzamide-NHMe | | B | 1.76 |

Biological Test

The compounds of formula (I) mentioned by way of example are characterised by an affinity for PI3-kinase, i.e. in the test by an $IC_{50}$ value of below 800 nmol/litre.

In order to determine the inhibitory activity of the compounds on PI3Kγ, an in-vitro kinase assay was used. The expression and purification of $G\beta_1\gamma_2$-His and p101-GST/p110γ from Sf9-cells (*Spodoptera frugiperda* 9) has already been described (Maier et al., J. Biol. Chem. 1999 (274) 29311-29317). Alternatively, the following method was used to determine the activity:

10 μl of the compound to be tested were placed on 96 well PVDF filter plates (0.45 μM) and incubated for 20 min with 30 μl lipid vesicles ($PIP_2$ (0.7 μg/well), phosphatidylethanolamine (7.5 μg/well), phosphatidylserine (7.5 μg/well), sphingomyelin (0.7 μg/well) and phosphatidylcholine (3.2 μg/well)) which contained 1-3 ng PI3K□ and 20-60 ng G□₁□₂-His. The reaction was started by the addition of 10 μl reaction buffer (40 mM Hepes, pH 7.5, 100 mM NaCl, 1 mM EGTA, 1 mM □-glycerophosphate, 1 mM DTT, 7 mM $MgCl_2$ and 0.1% BSA; 1 μM ATP and 0.2 μCi [□-³³P]-ATP) and incubated for 120 min at ambient temperature. The reaction solution was sucked through the filters by the application of a vacuum and washed with 200 μl PBS. After the plates had been dried at 50° C. the radioactivity remaining in the plates was determined after the addition of 50 µl scintillation liquid using a Top-Count measuring device.

Ranges Of Indications

It has been found that the compounds of formula (I) are characterised by a variety of possible applications in the therapeutic field. Particular mention should be made of those applications for which the compounds of formula (I) according to the invention are preferably used by virtue of their pharmaceutical activity as PI3-kinase modulators.

Generally speaking, these are diseases in whose pathology PI3-kinases are implicated, particularly inflammatory and allergic diseases. Particular mention should be made of inflammatory and allergic respiratory complaints, inflammatory diseases of the gastrointestinal tract, inflammatory diseases of the motor apparatus, inflammatory and allergic skin diseases, inflammatory eye diseases, diseases of the nasal mucosa, inflammatory or allergic ailments which involve autoimmune reactions or inflammation of the kidneys. The treatment may be symptomatic, adaptive, curative or preventative.

Respiratory complaints deserving special mention would be chronic and/or obstructive respiratory complaints. The compounds of formula I according to the invention may, by virtue of their pharmacological properties, bring about a reduction in Tissue damage Inflammation of the airways bronchial hyperreactivity the process of reconstruction of the lung as a result of inflammation worsening of the disease (progression).

The compounds according to the invention are particularly preferred for preparing a medicament for the treatment of chronic bronchitis, acute bronchitis, bronchitis caused by bacterial or viral infection or fungi or helminths, allergic bronchitis, toxic bronchitis, chronic obstructive pulmonary disease (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases such as e.g. pulmonary fibrosis, asbestosis and silicosis and alveolitis; hyperreactive airways, nasal polyps, pulmonary oedema such as e.g. toxic pulmonary oedema and ARDS/IRDS, pneumonitis of different origins, e.g. radiation-induced or caused by aspiration or infectious pneumonitis, collagenoses such as lupus erythematodes, systemic scleroderm, sarcoidosis or Boeck's disease.

The compounds of formula (I) are also suitable for the treatment of diseases of the skin, such as e.g. psoriasis, contact dermatitis, atopic dermatitis, alopecia areata (circular hair loss), erythema exsudativum multiforme (Stevens-Johnson Syndrome), dermatitis herpetiformis, scleroderm, vitiligo, nettle rash (urticaria), lupus erythematodes, follicular and surface pyoderm, endogenous and exogenous acne, acne rosacea and other inflammatory or allergic or proliferative skin diseases.

Moreover, the compounds of formula (I) are suitable for therapeutic use in cases of inflammatory or allergic complaints which involve autoimmune reactions, such as e.g. inflammatory bowel diseases, e.g. Crohn's disease or ulcerative colitis; diseases of the arthritis type, such as e.g. rheumatoid or psoriatic arthritis, osteoarthritis, rheumatoid spondylitis and other arthritic conditions or multiple sclerosis.

The following general inflammatory or allergic diseases may also be mentioned, which can be treated with medicaments containing compounds of formula (I):

inflammation of the eye, such as e.g. conjunctivitis of various kinds, e.g. caused by infections with fungi or bacteria, allergic conjunctivitis, irritable conjunctivitis, drug-induced conjunctivitis, keratitis, uveitis diseases of the nasal mucosa, such as e.g. allergic rhinitis/sinusitis or nasal polyps inflammatory or allergic conditions, such as e.g. systemic lupus erythematodes, chronic hepatitis, kidney inflammations such as glomerulonephritis, interstitial nephritis or idiopathic nephrotic syndrome.

Other diseases which may be treated with a drug containing compounds of formula (I) on the basis of their pharmacological activity include toxic or septic shock syndrome, atherosclerosis, middle ear infections (otitis media), hypertrophy of the heart, cardiac insufficiency, stroke, ischaemic reperfusion injury or neurodegenerative diseases such as Parkinson's disease or Alzheimer's.

Combinations

The compounds of formula (I) may be used on their own or in combination with other active substances of formula (I). If desired the compounds of formula (I) may also be used in combination with W, where W denotes a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors, preferably PI3-☐Kinase inhibitors. Moreover, double or triple combinations of W may be combined with the compounds of formula (I). Combinations of W might be, for example:

W denotes a betamimetic, combined with an active substance selected from among the anticholinergics, corticosteroids, PDE4-inhibitors, EGFR-inhibitors and LTD4-antagonists, W denotes an anticholinergic, combined with an active substance selected from among the betamimetics, corticosteroids, PDE4-inhibitors EGFR-inhibitors and LTD4-antagonists, W denotes a corticosteroid, combined with an active substance selected from among the PDE4-inhibitors, EGFR-inhibitors and LTD4-antagonists W denotes a PDE4-inhibitor, combined with an active substance selected from among the EGFR-inhibitors and LTD4-antagonists W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinoline-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazole-3-yl]-2-methyl-2-butylamino}ethanol
5-hydroxy-8-(1-hydroxy-2-isopropylaminobutyl)-2H-1,4-benzoxazin-3-(4H)-on
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2.4.6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1,1-dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other specified compounds are:
tropenol 2,2-diphenylpropionate methobromide
scopine 2,2-diphenylpropionate methobromide
scopine 2-fluoro-2,2-diphenylacetate methobromide
tropenol 2-fluoro-2,2-diphenylacetate methobromide
tropenol 3,3',4,4'-tetrafluorobenzilate methobromide
scopine 3,3',4,4'-tetrafluorobenzilate methobromide
tropenol 4,4'-difluorobenzilate methobromide
scopine 4,4'-difluorobenzilate methobromide
tropenol 3,3'-difluorobenzilate methobromide
scopine 3,3'-difluorobenzilate methobromide
tropenol 9-hydroxy-fluorene-9-carboxylate methobromide
tropenol 9-fluoro-fluorene-9-carboxylate methobromide
scopine 9-hydroxy-fluorene-9-carboxylate methobromide
scopine 9-fluoro-fluorene-9-carboxylate methobromide
tropenol 9-methyl-fluorene-9-carboxylate methobromide
scopine 9-methyl-fluorene-9-carboxylate methobromide
cyclopropyltropine benzilate methobromide
cyclopropyltropine 2,2-diphenylpropionate methobromide
cyclopropyltropine 9-hydroxy-xanthene-9-carboxylate methobromide
cyclopropyltropine 9-methyl-fluorene-9-carboxylate methobromide
cyclopropyltropine 9-methyl-xanthene-9-carboxylate methobromide
cyclopropyltropine 9-hydroxy-fluorene-9-carboxylate methobromide
cyclopropyltropine methyl 4,4'-difluorobenzilate methobromide
tropenol 9-hydroxy-xanthene-9-carboxylate methobromide
scopine 9-hydroxy-xanthene-9-carboxylate methobromide
tropenol 9-methyl-xanthene-9-carboxylate-methobromide
scopine 9-methyl-xanthene-9-carboxylate-methobromide
tropenol 9-ethyl-xanthene-9-carboxylate methobromide
tropenol 9-difluoromethyl-xanthene-9-carboxylate methobromide
scopine 9-hydroxymethyl-xanthene-9-carboxylate methobromide As corticosteroids it is preferable to use compounds selected from among prednisolone, prednisone, butixocort propionate, flunisolide, beclomethasone, triamcinolone, budesonide, fluticasone, mometasone, ciclesonide, rofleponide, dexamethasone, betamethasone, deflazacort, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-1'-hydroxy-16-methyl-3-oxo-17-propionyloxy-androsta-1,4-diene-17-carbothionate,
etiprednol-dichloroacetate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW- 842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-5-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxyphenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)ethoxy]-7-methoxy-quinazoline 4-[(3-chloro-4-fluoro-phenyl)amino]-6-[2-(2,2-dimethyl-6-oxo-morpholin-4-yl)ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxyethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxyethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl-piperidin-4-yloxy}-7-methoxy-quinazoline 4-[(3-chloro-4-fluoro-phenyl)amino]-6-{1-[(N-methyl-N-2-methoxyethylamino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methylamino)-cyclohexan-1-yloxy]-7-methoxy-quinazoline 4-[(3-chloro-4-fluoro-phenyl)amino]-6-[cis-4-(N-acetyl-N-methyl-amino)cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methylamino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PAF-antagonists used are preferably compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepine 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PI3-kinase-δ-inhibitors used are preferably compounds selected from among: IC87114, 2-(6-aminopurin-9-ylmethyl)-3-(2-chlorophenyl)-6,7-dimethoxy-3H-quinazolin-4-one; 2-(6-aminopurin-o-ylmethyl)-6-bromo-3-(2-chlorophenyl)-3H-quinazolin-4-one; 2-(6-aminopurin-o-ylmethyl)-3-(2-chlorophenyl)-7-fluoro-3H-quinazolin-4-one; 2-(6-aminopurin-9-ylmethyl)-6-chloro-3-(2-chlorophenyl)-3H-quinazolin-4-one; 2-(6-aminopurin-9-ylmethyl)-3-(2-chlorophenyl)-5-fluoro-3H-quinazolin-4-one; 2-(6-aminopurin-o-ylmethyl)-5-chloro-3-(2-chlorophenyl)-3H-quinazolin-4-one; 2-(6-aminopurin-9-ylmethyl)-3-(2-chlorophenyl)-5-methyl-3H-quinazolin-4-one; 2-(6-aminopurin-9-ylmethyl)-8-chloro-3-(2-chlorophenyl)-3H-quinazolin-4-one; 2-(6-aminopurin-9-ylmethyl)-3-biphenyl-2-yl-5-chloro-3H-quinazolin-4-one; 5-chloro-2-(9H-purin-6-ylsulphanylmethyl)-3-o-tolyl-3H-quinazolin-4-one; 5-chloro-3-(2-fluorophenyl)-2-(9H-purin-6-yl-sulphanylmethyl)-3H-quinazolin-4-one; 2-(6-aminopurin-9-ylmethyl)-5-chloro-3-(2-fluorophenyl)-3H-quinazolin-4-one; 3-biphenyl-2-yl-5-chloro-2-(9H-purin-6-ylsulphanylmethyl)-3H-quinazolin-4-one; 5-chloro-3-(2-methoxyphenyl)-2-(9H-purin-6-yl-sulphanylmethyl)-3H-quinazolin-4-one; 3-(2-chlorophenyl)-5-fluoro-2-(9H-purin-6-ylsulphanylmethyl)-3H-quinazolin-4-one; 3-(2-chlorophenyl)-6,7-dimethoxy-2-(9H-purin-6-yl-sulphanylmethyl)-3H-quinazolin-4-one; 6-bromo-3-(2-chlorophenyl)-2-(9H-purin-6-yl-sulphanylmethyl)-3H-quinazolin-4-one; 3-(2-chlorophenyl)-8-trifluoromethyl-2-

(9H-purin-6-ylsulphanylmethyl)-3H-quinazolin-4-one; 3-(2-chlorophenyl)-2-(9H-purin-6-ylsulphanylmethyl)-3H-benzo[g]quinazolin-4-one; 6-chloro-3-(2-chlorophenyl)-2-(9H-purin-6-yl-sulphanylmethyl)-3H-quinazolin-4-one; 8-chloro-3-(2-chlorophenyl)-2-(9H-purin-6-yl-sulphanylmethyl)-3H-quinazolin-4-one; 3-(2-chlorophenyl)-7-fluoro-2-(9H-purin-6-yl-sulphanylmethyl)-3H-quinazolin-4-one; 3-(2-chlorophenyl)-7-nitro-2-(9H-purin-6-yl-sulphanylmethyl)-3H-quinazolin-4-one; 3-(2-chlorophenyl)-6-hydroxy-2-(9H-purin-6-yl-sulphanylmethyl)-3H-quinazolin-4-one; 5-chloro-3-(2-chlorophenyl)-2-(9H-purin-6-yl-sulphanylmethyl)-3H-quinazolin-4-one; 3-(2-chlorophenyl)-5-methyl-2-(9H-purin-6-ylsulphanylmethyl)-3H-quinazolin-4-one; 3-(2-chlorophenyl)-6,7-difluoro-2-(9H-purin-6-yl-sulphanylmethyl)-3H-quinazolin-4-one; 3-(2-chlorophenyl)-6-fluoro-2-(9H-purin-6-yl-sulphanylmethyl)-3H-quinazolin-4-one; 2-(6-aminopurin-9-ylmethyl)-3-(2-isopropylphenyl)-5-methyl-3H-quinazolin-4-one; 2-(6-aminopurin-9-ylmethyl)-5-methyl-3-o-tolyl-3H-quinazolin-4-one; 3-(2-fluorophenyl)-5-methyl-2-(9H-purin-6-ylsulphanylmethyl)-3H-quinazolin-4-one; 2-(6-aminopurin-9-ylmethyl)-5-chloro-3-o-tolyl-3H-quinazolin-4-one; 2-(6-aminopurin-9-ylmethyl)-5-chloro-3-(2-methoxyphenyl)-3H-quinazolin-4-one; 2-(2-amino-9H-purin-6-ylsulphanylmethyl)-3-cyclopropyl-5-methyl-3H-quinazolin-4-one; 3-cyclopropylmethyl-5-methyl-2-(9H-purin-6-ylsulphanylmethyl)-3H-quinazolin-4-one; 2-(6-aminopurin-9-ylmethyl)-3-cyclopropylmethyl-5-methyl-3H-quinazolin-4-one; 2-(2-amino-9H-purin-6-ylsulphanylmethyl)-3-cyclopropylmethyl-5-methyl-3H-quinazolin-4-one; 5-methyl-3-phenethyl-2-(9H-purin-6-ylsulphanylmethyl)-3H-quinazolin-4-one; 2-(2-amino-9H-purin-6-ylsulphanylmethyl)-5-methyl-3-phenethyl-3H-quinazolin-4-one; 3-cyclopentyl-5-methyl-2-(9H-purin-6-ylsulphanylmethyl)-3H-quinazolin-4-one; 2-(6-aminopurin-9-ylmethyl)-3-cyclopentyl-5-methyl-3H-quinazolin-4-one; 3-(2-chloropyridin-3-yl)-5-methyl-2-(9H-purin-6-ylsulphanylmethyl)-3H-quinazolin-4-one; 2-(6-aminopurin-9-ylmethyl)-3-(2-chloropyridin-3-yl)-5-methyl-3H-quinazolin-4-one; 3-methyl-4-[5-methyl-4-oxo-2-(9H-purin-6-ylsulphanylmethyl)-4H-quinazolin-3-yl]-benzoic acid; 3-cyclopropyl-5-methyl-2-(9H-purin-6-ylsulphanylmethyl)-3H-quinazolin-4-one; 2-(6-aminopurin-9-ylmethyl)-3-cyclopropyl-5-methyl-3H-quinazolin-4-one; 5-methyl-3-(4-nitrobenzyl)-2-(9H-purin-6-ylsulphanylmethyl)-3H-quinazolin-4-one; 3-cyclohexyl-5-methyl-2-(9H-purin-6-ylsulphanylmethyl)-3H-quinazolin-4-one; 2-(6-aminopurin-9-ylmethyl)-3-cyclohexyl-5-methyl-3H-quinazolin-4-one; 2-(2-amino-9H-purin-6-ylsulphanylmethyl)-3-cyclohexyl-5-methyl-3H-quinazolin-4-one; 5-methyl-3-(E-2-phenylcyclopropyl)-2-(9H-purin-6-ylsulphanylmethyl)-3H-quinazolin-4-one; 3-(2-chlorophenyl)-5-fluoro-2-[(9H-purin-6-ylamino)methyl]-3H-quinazolin-4-one; 2-[(2-amino-9H-purin-6-ylamino)methyl]-3-(2-chlorophenyl)-5-fluoro-3H-quinazolin-4-one; 5-methyl-2-[(9H-purin-6-ylamino)methyl]-3-o-tolyl-3H-quinazolin-4-one; 2-[(2-amino-9H-purin-6-ylamino)methyl]-5-methyl-3-o-tolyl-3H-quinazolin-4-one; 2-[(2-fluoro-9H-purin-6-ylamino)methyl]-5-methyl-3-o-tolyl-3H-quinazolin-4-one; (2-chlorophenyl)dimethylamino-(9H-purin-6-ylsulphanylmethyl)-3H-quinazolin-4-one; 5-(2-benzyloxyethoxy)-3-(2-chlorophenyl)-2-(9H-purin-6-ylsulphanylmethyl)-3H-quinazolin-4-one; 3-(2-chlorophenyl)-5-fluoro-4-oxo-3,4-dihydro-quinazolin-2-ylmethyl 6-aminopurine-9-carboxylate; N-[3-(2-chlorophenyl)-5-fluoro-4-oxo-3,4-dihydro-quinazolin-2-ylmethyl]-2-(9H-purin-6-ylsulphanyl)-acetamide; 2-[1-(2-fluoro-9H-purin-6-ylamino)ethyl]-5-methyl-3-o-tolyl-3H-quinazolin-4-one; 5-methyl-2-[1-(9H-purin-6-ylamino)ethyl]-3-o-tolyl-3H-quinazolin-4-one; 2-(6-dimethylaminopurine-9-ylmethyl)-5-methyl-3-o-tolyl-3H-quinazolin-4-one; 5-methyl-2-(2-methyl-6-oxo-1,6-dihydro-purin-7-ylmethyl)-3-o-tolyl-3H-quinazolin-4-one; 5-methyl-2-(2-methyl-6-oxo-1,6-dihydro-purin-9-ylmethyl)-3-o-tolyl-3H-quinazolin-4-one; 2-(amino-dimethylaminopurine-9-ylmethyl)-5-methyl-3-o-tolyl-3H-quinazolin-4-one; 2-(2-amino-9H-purin-6-ylsulphanylmethyl)-5-methyl-3-o-tolyl-3H-quinazolin-4-one; 2-(4-amino-1,3,5-triazin-2-ylsulphanylmethyl)-5-methyl-3-o-tolyl-3H-quinazolin-4-one; 5-methyl-2-(7-methyl-7H-purin-6-ylsulphanylmethyl)-3-o-tolyl-3H-quinazolin-4-one; 5-methyl-2-(2-oxo-1,2-dihydro-pyrimidin-4-ylsulphanylmethyl)-3-o-tolyl-3H-quinazolin-4-one; 5-methyl-2-purin-7-ylmethyl-3-o-tolyl-3H-quinazolin-4-one; 5-methyl-2-purin-9-ylmethyl-3-o-tolyl-3H-quinazolin-4-one; 5-methyl-2-(9-methyl-9H-purin-6-ylsulphanylmethyl)-3-o-tolyl-3H-quinazolin-4-one; 2-(2,6-diamino-pyrimidin-4-ylsulphanylmethyl)-5-methyl-3-o-tolyl-3H-quinazolin-4-one; 5-methyl-2-(5-methyl-[1,2,4]triazolo[1.5-a]pyrimidin-7-ylsulphanylmethyl)-3-o-tolyl-3H-quinazolin-4-one; 5-methyl-2-(2-methylsulphanyl-9H-purin-6-ylsulphanylmethyl)-3-o-tolyl-3H-quinazolin-4-one; 2-(2-hydroxy-9H-purin-6-ylsulphanylmethyl)-5-methyl-3-o-tolyl-3H-quinazolin-4-one; 5-methyl-2-(1-methyl-1H-imidazol-2-ylsulphanylmethyl)-3-o-tolyl-3H-quinazolin-4-one; 5-methyl-3-o-tolyl-2-(H-[1,2,4]triazol-3-ylsulphanylmethyl)-3H-quinazolin-4-one; 2-(2-amino-6-chloro-purin-9-ylmethyl)-5-methyl-3-o-tolyl-3H-quinazolin-4-one; 2-(6-aminopurin-7-ylmethyl)-5-methyl-3-o-tolyl-3H-quinazolin-4-one; 2-(7-amino-1,2,3-triazolo[4,5-d]pyrimidin-3-ylmethyl)-5-methyl-3-o-tolyl-3H-quinazolin-4-one; 2-(7-amino-1,2,3-triazolo[4,5-d]pyrimidin-1-yl-methyl)-5-methyl-3-o-tolyl-3H-quinazolin-4-one; 2-(6-amino-9H-purin-2-ylsulphanylmethyl)-5-methyl-3-o-tolyl-3H-quinazolin-4-one; 2-(2-amino-6-ethylamino-pyrimidin-4-ylsulphanylmethyl)-5-methyl-3-o-tolyl-3H-quinazolin-4-one; 2-(3-amino-5-methylsulphanyl-1,2,4-triazol-1-ylmethyl)-5-methyl-3-o-tolyl-3H-quinazolin-4-one; 2-(5-amino-3-methylsulphanyl-1,2,4-triazol-1-ylmethyl)-5-methyl-3-o-tolyl-3H-quinazolin-4-one; 5-methyl-2-(6-methylaminopurin-9-ylmethyl)-3-o-tolyl-3H-quinazolin-4-one; 2-(6-benzylaminopurin-9-ylmethyl)-5-methyl-3-o-tolyl-3H-quinazolin-4-one; 2-(2,6-diaminopurine-9-ylmethyl)-5-methyl-3-o-tolyl-3H-quinazolin-4-one; 5-methyl-2-(9H-purin-6-ylsulphanylmethyl)-3-o-tolyl-3H-quinazolin-4-one; 3-isobutyl-5-methyl-2-(9H-purin-6-ylsulphanylmethyl)-3H-quinazolin-4-one; N-{2-[5-methyl-4-oxo-2-(9H-purin-6-ylsulphanylmethyl)-4H-quinazolin-3-yl]-phenyl}-acetamide; 5-methyl-3-(E-2-methyl-cyclohexyl)-2-(9H-purin-6-ylsulphanylmethyl)-3H-quinazolin-4-one; 2-[5-methyl-4-oxo-2-(9H-purin-6-ylsulphanylmethyl)-4H-quinazolin-3-yl]-benzoic acid; 3-{2-[(2-dimethylaminoethyl)methylamino]phenyl}-5-methyl-2-(9H-purin-6-ylsulphanylmethyl)-3H-quin-azolin-4-one; 3-(2-chlorophenyl)-5-methoxy-2-(9H-purin-6-ylsulphanylmethyl)-3H-quinazolin-4-one; 3-(2-chlorophenyl)-5-(2-morpholin-4-yl-ethylamino)-2-(9H-purin-6-ylsulphanylmethyl)-3H-quinazolin-4-one; 3-benzyl-5-methoxy-2-(9H-purin-6-ylsulphanylmethyl)-3H-quinazolin-4-one; 2-(6-aminopurin-9-ylmethyl)-3-(2-benzyloxyphenyl)-5-methyl-3H-quinazolin-4-one; 2-(6-aminopurin-9-ylmethyl)-3-(2-hydroxyphenyl)-5-methyl-3H-quinazolin-4-one; 2-(1-(2-amino-9H-purin-6-ylamino)ethyl)-5-methyl-3-o-tolyl-3H-quinazolin-4-one; 5-methyl-2-[1-(9H-purin-6-ylamino)propyl]-3-o-tolyl-3H-quinazolin-4-one; 2-(1-(2-fluoro-9H-purin-6-ylamino)propyl)-5-methyl-3-o-tolyl-3H- quinazolin-4-one; 2-(1-(2-amino-9H-purin-6-ylamino) propyl)-5-methyl-3-o-tolyl-3H-quinazolin-4-one; 2-(2-benzyloxy-1-(9H-purin-6-ylamino)ethyl)-5-methyl-3-o-tolyl-3H-quinazolin-4-one; 2-(6-aminopurin-9-ylmethyl)-5-methyl-3-{2-(2-(1-methylpyrrolidin-2-yl)-ethoxy)phenyl}-3H-quinazolin-4-one; 2-(6-aminopurin-9-ylmethyl)-3-(2-(3-dimethylaminopropoxy)-phenyl)-5-methyl-3H-quinazolin-4-one; 2-(6-aminopurin-9-ylmethyl)-5-methyl-3-(2-prop-2-ynyloxyphenyl)-3H-quinazolin-4-one; 2-(2-(1-(6-aminopurin-9-ylmethyl)-5-methyl-4-oxo-4H-quinazolin-3-yl]-phenoxy}-acetamide; 5-chloro-3-(3,5-difluoro-phenyl)-2-[1-(9H-purin-6-ylamino)-propyl]-3H-quinazolin-4-one; 3-phenyl-2-[1-(9H-purin-6-ylamino)-propyl]-3H-quinazolin-4-one; 5-fluoro-3-phenyl-2-[1-(9H-purin-6-ylamino)-propyl]-3H-quinazolin-4-one; 3-(2,6-difluoro-phenyl)-5-methyl-2-[1-(9H-purin-6-ylamino)-propyl]-3H-quinazolin-4-one; 6-fluoro-3-phenyl-2-[1-(9H-purin-6-ylamino)-ethyl]-3H-quinazolin-4-one; 3-(3,5-difluoro-phenyl)-5-methyl-2-[1-(9H-purin-6-ylamino)-ethyl]-3H-quinazolin-4-one; 5-fluoro-3-phenyl-2-[1-(9H-purin-6-ylamino)-ethyl]-3H-quinazolin-4-one; 3-(2,3-difluoro-phenyl)-5-methyl-2-[1-(9H-purin-6-ylamino)-ethyl]-3H-quinazolin-4-one; 5-methyl-3-phenyl-2-[1-(9H-purin-6-ylamino)-ethyl]-3H-quinazolin-4-one; 3-(3-chloro-phenyl)-5-methyl-2-[1-(9H-purin-6-ylamino)-ethyl]-3H-quinazolin-4-one; 5-methyl-3-phenyl-2-[(9H-purin-6-ylamino)-methyl]-3H-quinazolin-4-one; 2-[(2-amino-9H-purin-6-ylamino)methyl]-3-(3,5-difluoro-phenyl)-5-methyl-3H-quinazolin-4-one; 3-{2-[1,2]-diethylamino-ethyl)-methyl-amino]-phenyl)-5-methyl-2-[(9H-purin-6-ylamino)methyl]-3H-quinazolin-4-one; 5-chloro-3-(2-fluoro-phenyl)-2-[(9H-purin-6-ylamino)methyl]-3H-quinazolin-4-one; 5-chloro-2-[(9H-purin-6-ylamino)-methyl]-3-o-tolyl-3H-quinazolin-4-one; 5-chloro-3-(2-chloro-phenyl)-2-[(9H-purin-6-ylamino)-methyl]-3H-quinazolin-4-one; 6-fluoro-3-(3-fluoro-phenyl)-2-[1-(9H-purin-6-ylamino)ethyl]-3H-quinazolin-4-one; 2-[1-(2-amino-9H-purin-6-ylamino)-ethyl]-5-chloro-3-(3-fluoro-phenyl)-3H-quinazolin-4-one; and the pharmaceutically acceptable salts and solvates thereof.

Formulations

The compounds according to the invention may be administered by oral, transdermal, inhalative, parenteral or sublingual route. The compounds according to the invention are present as active ingredients in conventional preparations, for example in compositions consisting essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 0.1 and 5000, preferably between 1 and 500, more preferably between 5-300 mg/dose for oral administration, and between 0.001 and 50, preferably between 0.1 and 10 mg/dose for intravenous, subcutaneous or intramuscular administration. Examples of inhalable formulations include inhalable powders, propellant-containing metered-dose aerosols or propellant-free inhalable solutions. Within the scope of the present invention the term propellant-free inhalable solutions also includes concentrates or sterile ready-to-use inhalable solutions. For use by inhalation it is preferable to use powders, ethanolic or aqueous solutions. For inhalation, according to the invention, solutions containing 0.01 to 1.0, preferably 0.1 to 0.5% active substance are suitable. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable formulations include, for example, tablets, capsules, suppositories, solutions, syrups, emulsions or dispersible powders. Corresponding tablets may be obtained for example by mixing the active substance(s) with known excipients, for example inert diluents, such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The inhalable powders which may be used according to the invention may contain the active substance according to the invention either on its own or in admixture with suitable physiologically acceptable excipients.

If the active substances according to the invention are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. In some cases it may seem appropriate to add finer excipient fractions with an average particle size of 1 to 9 μm to the excipient mentioned above. These finer excipients are also selected from the group of possible excipients listed hereinbefore. Finally, in order to prepare the inhalable powders according to the invention, micronised active substances according to the invention, preferably with an average particle size of 0.5 to 10 μm, more preferably from 1 to 5 μm, are added to the excipient mixture. Processes for producing the inhalable powders according to the invention by grinding and micronising and finally mixing the ingredients together are known from the prior art.

The inhalable powders according to the invention may be administered using inhalers known from the prior art.

Inhalation aerosols containing propellant gas according to the invention may contain active substances according to the invention dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing the active substance according to the invention are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

The addition of editic acid (EDTA) or one of the known salts thereof, sodium edetate, as stabiliser or complexing agent may optionally be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance according to the invention, only benzalkonium chloride and sodium edetate. In another preferred embodiment, no sodium edetate is present.

A therapeutically effective daily dose is between 1 and 2000 mg, preferably 10-500 mg per adult.

The Examples which follow illustrate the present invention without restricting its scope:

Examples of Pharmaceutical Formulations

| A) Tablets | per tablet |
|---|---|
| active substance | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, granulated while wet and dried. The granulate, the rest of the corn starch and the magnesium stearate are screened and mixed together. The mixture is compressed to form tablets of a suitable shape and size.

| B) Tablets | per tablet |
|---|---|
| active substance | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) Coated tablets | per coated tablet |
|---|---|
| Active substance | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in a known manner with a covering consisting essentially of sugar and talc. The finished coated tablets are polished with wax

| D) Capsules | per capsule |
|---|---|
| Active substance | 50 mg |
| Corn starch | 268.5 mg |
| Magnesium stearate | 1.5 mg |
| | 320 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) Suppositories | |
|---|---|
| Active substance | 50 mg |
| Solid fat | 1650 mg |
| | 1700 mg |

The hard fat is melted. At 40° C. the ground active substance is homogeneously dispersed. It is cooled to 38° C. and poured into slightly chilled suppository moulds.

| G) Oral suspension | |
|---|---|
| active substance | 50 mg |
| hydroxyethylcellulose | 50 mg |
| sorbic acid | 5 mg |
| sorbitol (70%) | 600 mg |
| glycerol | 200 mg |
| flavouring | 15 mg |
| water ad | 5 ml |

Distilled water is heated to 70° C. Hydroxyethyl-cellulose is dissolved therein with stirring. After the addition of sorbitol solution and glycerol the mixture is cooled to ambient temperature. At ambient temperature, sorbic acid, flavouring and substance are added. To eliminate air from the suspension it is evacuated with stirring.

and 50 mg of active substance.

| H) Metered-dose aerosol (suspension) | |
|---|---|
| active substance | 0.3 wt. % |
| sorbitolan trioleate | 0.6 wt. % |
| HFA134A:HFA227 2:1 | 99.1 wt. % |

The suspension is transferred into a conventional aerosol container with a metering valve. Preferably, 50 µl of suspension are delivered per spray. The active substance may also be metered in higher doses if desired.

| I) Metered-dose aerosol (solution) | |
|---|---|
| active substance | 0.3 wt. % . % |
| abs. ethanol | 20 wt. % |
| aqueous HCl 0.01 mol/l | 2.0 wt. % |
| HFA134A | 77.7 wt. % |

The solution is produced in the usual way by mixing the individual ingredients together.

| J) Inhalable powder | |
|---|---|
| active substance | 80 µg |
| lactose monohydrate | ad 10 mg |

The powder for inhalation is produced in the usual way by mixing the individual ingredients together.

The invention claimed is:
1. A compound of the formula (I),

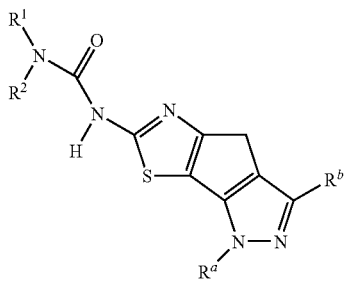

wherein
- $R^a$ denotes hydrogen or an optionally substituted group selected from among $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, $C_9$-$C_{13}$-spiro, $C_3$-$C_8$-heterocycloalkyl and $C_3$-$C_8$-heterocycloalkyl-$C_1$-$C_4$-alkyl ;
- $R^b$ denotes $NH_2$ OH,
- or an optionally substituted group selected from among $C_1$-$C_8$-alkyl, $C_3$-$C_8$-cycloalkyl, $C_2$-$C_8$-alkenyl, $C_2$-$C_8$-alkynyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, $C_9$-$C_{13}$-spiro, $C_3$-$C_8$-heterocycloalkyl, $CONH_2$, $C_6$-$C_{14}$-aryl-NH, $C_3$-$C_8$-heterocycloalkyl-NH- and OMe;
- $R^1$ denotes hydrogen or an optionally substituted group selected from among $C_1$-$C_8$-alkyl, $C_3$-$C_8$-cycloalkyl, $C_2$-$C_8$-alkenyl, $C_2$-$C_8$-alkynyl and $C_6$-$C_{14}$-aryl-$C_1$-$C_5$-alkyl-;
- or
- $R^2$ denotes hydrogen or an optionally substituted group selected from among $C_1$-$C_8$-alkyl, $C_3$-$C_8$-cycloalkyl, $C_2$-$C_8$-alkenyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl -$C_1$-$C_4$-alkyl, $C_5$-$C_{10}$-heteroaryl-$C_1$-$C_6$-alkyl, $C_9$-$C_{13}$-spiro, $C_3$-$C_8$-heterocycloalkyl, $C_3$-$C_8$-heterocycloalkyl-$C_1$-$C_6$-alkyl- and $C_6$-$C_{14}$-aryl-$C_1$-$C_6$-alkyl-;
- or
- $R^1$ and $R^2$ together form an optionally substituted five-, six- or seven-membered ring consisting of carbon atoms and optionally 1 to 2 heteroatoms, selected from among oxygen, sulphur and nitrogen,
- or
- $R^1$ and $R^2$ together form an optionally substituted nine- to thirteen-membered spirocyclic ring,
- or
- $R^2$ denotes a group selected from among general formulae (A1) to (A18)

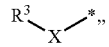 (A1)

 (A2)

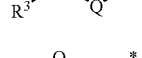 (A3)

 (A4)

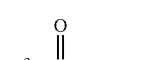 (A5)

 (A6)

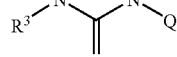 (A7)

 (A8)

 (A9)

 (A10)

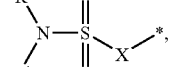 (A11)

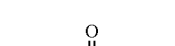 (A12)

 (A13)

-continued

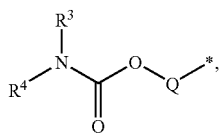
(A14)

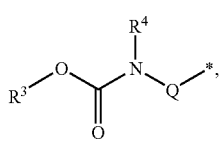
(A15)

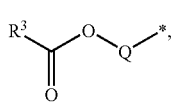
(A16)

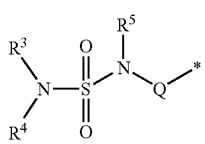
and
(A17)

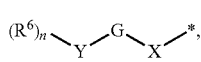
(A18)

wherein
X and Y may be linked to the same or different atoms of G, and

X denotes a bond or an optionally substituted group selected from among $C_1$-$C_7$-alkylene, $C_3$-$C_7$-alkenylene and $C_3$-$C_7$-alkynylene, or X together with $R^1$, $R^3$ or $R^4$ may form a $C_1$-$C_7$-alkylene bridge;

Y denotes a bond or optionally substituted $C_1$-$C_4$-alkylene;

Q denotes an optionally substituted group selected from among $C_1$-$C_7$-alkylene, $C_3$-$C_7$-alkenylene and $C_3$-$C_7$-alkynylene; or Q together with $R^1$, $R^3$ or $R^4$ may form a $C_1$-$C_7$-alkylene bridge;

$R^3$, $R^4$ and $R^5$ which may be identical or different, denote hydrogen or an optionally substituted group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_4$-alkyl, $NR^7R^8$, $NR^7R^8$-$C_1$-$C_4$-alkyl, $C_1$-$C_4$-alkoxy, $C_1$-$C_4$-alkoxy-$C_1$-$C_4$-alkyl, $C_6$-$C_{14}$-aryl and $C_5$-$C_{10}$-heteroaryl;

or in each case two of the substituents $R^3$, $R^4$ and $R^5$ together form an optionally substituted five-, six- or seven -membered ring, consisting of carbon atoms and optionally 1-2 heteroatoms, selected from among oxygen, sulphur and nitrogen;

G denotes a saturated, partially saturated or unsaturated ring system consisting of 3-10 C atoms, wherein optionally up to 6 C atoms are replaced by heteroatoms selected from among nitrogen, oxygen and sulphur;

$R^6$ which may be identical or different, denote hydrogen or an optionally substituted group selected from among $C_1$-$C_8$-alkyl, $C_2$-$C_6$-alkenyl $C_3$-$C_8$-cycloalkyl, $C_2$-$C_6$-haloalkyl, $C_6$-$C_{14}$-aryl, $C_5$-$C_{10}$-heteroaryl and and $C_3$-$C_8$-heterocycloalkyl, or a group selected from among =O, $NR^7R^8OR$, —CO—$C_1$-$C_3$-alkyl -$NR^7R^8$, —O—$C_1$-$C_3$-alkyl-$NR^7R^8$, $CONR^7R^8$, $NR^7COR^8$, —CO—$C_1$-$C_3$-alkyl-$NR^7(CO)$ $OR^8$, —O(CO)$NR^7R^8$, $NR^7(CO)NR^8R^9$, $NR^7(CO)$ $OR^8$, $(CO)OR^7$, —O(CO)$R^7$, $COR^7$, $(SO)R^7$, $(SO_2)R^7$, $(SO_2)NR^7R^8$, $NR^7(SO_2)R^8$, $NR^7(SO_2)NR^8R^9$, CN, —$C_1$-$C_3$-alkyl-$C_6$-$C_{14}$-aryl , —NH-CO—NH—$C_1$-$C_3$-alkyl and halogen;

n denotes 1, 2 or 3;

$R^7$, $R^8$ and $R^9$ which may be identical or different, denote hydrogen or an optionally substituted group selected from among $C_1$-$C_8$-alkyl, $C_3$-$C_8$-cycloalkyl, $C_1$-$C_6$-haloalkyl, $C_1$- $C_4$-alkyl-$C_3$-$C_8$-cycloalkyl, $C_3$-$C_8$-cycloalkyl-$C_1$-$C_3$-alkyl, $C_6$-$C_{14}$-aryl, $C_1$-$C_4$-alkyl-$C_6$-$C_{14}$-aryl, $C_6$-$C_{14}$-aryl-$C_1$-$C_4$-alkyl, $C_3$-$C_8$-heterocycloalkyl, $C_1$-$C_5$-alkyl-$C_3$-$C_8$-heterocycloalkyl, $C_3$-$C_8$-heterocycloalkyl-$C_1$-$C_4$-alkyl, $C_1$-$C_4$-alkyl(CO) and $C_1$-$C_4$-alkyl—O(CO)—;

or in each case two of the substituents $R^7$, $R^8$ and $R^9$ together optionally substituted five-, six- seven-membered ring, consisting of carbon atoms and optionally 1-2 heteroatoms, selected from among oxygen, sulphur and nitrogen; optionally in the form of the tautomers, the racemates, the enantiomers, the diastereomers and the mixtures thereof, as well as optionally the pharmacologically acceptable acid addition salts thereof;

with the proviso that the following compounds are excluded:
a) 1,1-dimethyl-3-(4-phenyl-4,7-dihydro-3-thia-1,4,5-triaza-cyclopenta[a]pentalen-2-yl) -urea
b) (4-phenyl-4,7-dihydro-3 -thia- 1 ,4,5-triaza-cyclopenta [a]pentalen-2-yl)-urea
c) 1-(2-dimethylamino-ethyl)-3-(4-phenyl-4,7-dihydro-3-thia-1,4,5-triaza -cyclopenta[a]pentalen-2-yl)-urea
d) 1-(2-dimethylamino-ethyl)-1-methyl-3-(4-phenyl-4,7-dihydro-3-thia-1,4,5-triaza -cyclopenta[a]pentalen-2-yl)-urea
e) 4-methyl-piperazine-1-carboxylic acid (4-phenyl-4,7-dihydro-3-thia-1,4,5-triaza -cyclopenta[a]pentalen-2-yl)-amide
f) 1-[4-(2-chloro-phenyl)-4,7-dihydro-3-thia-1,4,5-triaza-cyclopenta[a]pentalen-2-yl]-3-(2-dimethylamino-ethyl)-urea
g) 3-[4-(2-chloro-phenyl)-4,7-dihydro-3-thia-1,4,5 -triaza-cyclopenta[a]pentalen-2-yl]-1-(2-dimethylamino-ethyl)- 1-methyl-urea
h) 1-[4-(2-chloro-phenyl)-4,7-dihydro-3-thia-1,4,5-triaza-cyclopenta[a]pentalen-2-yl]-3-methyl-urea
i) 1-[4-(2-chloro-phenyl)-4,7-dihydro-3-thia-1,4,5-triaza-cyclopenta[a]pentalen-2-yl]-3-(2-imidazol-1-yl-ethyl)-urea
j) 3-4-(2-chloro-phenyl)-4,7-dihydro-3-thia-1,4,5-triaza-cyclopenta[a]pentalen-2-yl]-1,1-dimethyl-urea, and
k) piperidine-1-carboxylic acid (4-phenyl-4,7-dihydro-3-thia-1,4,5-triaza -cyclopenta[a]pentalen-2-yl)-amide.

2. The compound according to claim 1
wherein
X, Y, Q and G may have the meaning specified and
$R^a$ denotes hydrogen or a group selected from among $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, $C_9$-$C_{13}$-spiro, $C_3$-$C_8$-heterocycloalkyl and $C_3$-$C_8$-heterocycloalkyl-$C_1$-$C_4$-alkyl, which may optionally be substituted by one or more of the groups, which may be identical or different, selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, C$_1$-C$_4$-alkoxy, CN, NO$_2$, NR$^{10}$R$^{11}$, OR$^{10}$, COR$^{10}$, COOR$^{10}$, CONR$^{10}$R$^{11}$, NR$^{10}$COR$^{11}$, NR$^{10}$(CO)NR$^{11}$R$^{12}$, O(CO)NR$^{10}$R$^{11}$, NR$^{10}$(CO)OR$^{11}$, SO$_2$R$^{10}$, SOR$^{10}$, SO$_2$NR$^{10}$R$^{11}$, NR$^{10}$SO$_2$NR$^{11}$R$^{12}$ and NR$^{10}$SO$_2$R$^{11}$;

R$^{10}$, R$^{11}$ and R$^{12}$ which may be identical or different, denote hydrogen or a group selected from among C$_1$-C$_6$-alkyl, C$_2$-C$_6$-alkenyl, C$_2$-C$_6$-alkynyl, C$_3$-C$_8$-cycloalkyl and C$_1$-C$_6$ haloalkyl;

or in each case two of the groups

R$^{10}$, R$^{11}$ and R$^{12}$ together form a five-, six- or seven-membered ring, consisting of carbon atoms and optionally 1-2 heteroatoms, selected from among oxygen, sulphur and nitrogen;

R$^b$ denotes hydrogen, NH$_2$ or OH, or an optionally substituted group selected from among C$_1$-C$_8$-alkyl, C$_3$-C$_8$-cycloalkyl, C$_2$-C$_8$-alkenyl, C$_2$-C$_8$-alkynyl, C$_3$-C$_8$-cycloalkenyl, C$_1$-C$_6$-haloalkyl, C$_6$-C$_{14}$-aryl, C$_6$-C$_{14}$-aryl-C$_1$-C$_5$-alkyl, C$_5$-C$_{10}$-heteroaryl, C$_3$-C$_8$-cycloalkyl-C$_1$-C$_4$-alkyl, C$_3$-C$_8$-cycloalkenyl-C$_1$-C$_4$-alkyl, C$_5$-C$_{10}$-heteroaryl-C$_1$-C$_4$-alkyl, C$_9$-C$_{13}$-spiro, C$_3$-C$_8$-heterocycloalkyl, CONH$_2$, C$_6$-C$_{14}$-aryl-NH, C$_3$-C$_8$-heterocycloalkyl-NH- ; and OMe which may optionally be substituted by one or more of the groups, which may be identical or different, selected from among C$_1$-C$_6$-alkyl, C$_2$-C$_6$-alkenyl, C$_2$-C$_6$-alkynyl, C$_3$-C$_8$-cycloalkyl, C$_1$-C$_6$-haloalkyl, halogen, OH, OMe, CN, NH$_2$, NHMe and NMe$_2$;

R$^1$ denotes hydrogen or a group selected from among C$_1$-C$_8$-alkyl, C$_3$-C$_8$-cycloalkyl, C$_2$-C$_8$-alkenyl, C$_2$-C$_8$-alkynyl and C$_6$-C$_{14}$-aryl-C$_1$-C$_5$-alkyl, which may optionally be substituted by one or more of the groups, which may be identical or different, selected from among halogen, NH$_2$, OH, CN, C$_1$-C$_6$-alkyl, OMe, -NH(CO)-alkyl and -(CO)O-alkyl;

R$^2$ denotes hydrogen or a group selected from among C$_1$-C$_8$ alkyl, C$_3$-C$_8$-cycloalkyl, C$_2$-C$_8$-alkenyl, C$_3$-C$_8$-cycloalkenyl, C$_1$-C$_6$-haloalkyl, C$_6$-C$_{14}$-aryl, C$_6$-C$_{14}$-aryl-C$_1$-C$_5$-alkyl, C$_5$-C$_{10}$-heteroaryl, C$_3$-C$_8$-cycloalkyl-C$_1$-C$_4$-alkyl, C$_3$-C$_8$-cycloalkenyl-C$_1$-C$_4$-alkyl, C$_5$-C$_{10}$-heteroaryl-C$_1$-C$_6$-alkyl, C$_9$-C$_{13}$-spiro, C$_3$-C$_8$-heterocycloalkyl, C$_3$-C$_8$-heterocycloalkyl-C$_1$-C$_6$-alkyl and C$_6$-C$_{14}$-aryl-C$_1$-C$_6$-alkyl, which may optionally be substituted by one or more of the groups, which may be identical or different, selected from among halogen, NH$_2$, OH, CN, C$_1$-C$_6$-alkyl, OMe, —NH(CO)-alkyl, =O, COOH and —(CO)O-alkyl, or R$^1$ and R$^2$ together form a five-, six- or seven-membered ring consisting of carbon atoms and optionally 1 to 2 heteroatoms, selected from among oxygen, sulphur and nitrogen, which may optionally be substituted by one or more of the groups, which may be identical or different, selected from among halogen, NH$_2$, OH, CN, C$_1$-C$_6$-alkyl, OMe, —NH(CO)—C$_1$-C$_4$-alkyl, and —(CO)O-C$_1$-C$_4$-alkyl, or R$^1$ and R$^2$ together form an optionally substituted nine- to thirteen-membered spirocyclic ring, or R$^2$ denotes a group selected from among general formulae (A1) to (A18)

 (A1)

 (A2)

 (A3)

 (A4)

 (A5)

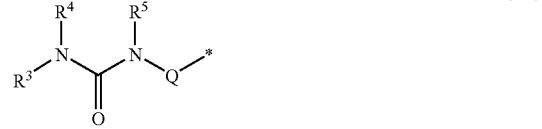 (A6)

 (A7)

 (A8)

 (A9)

 (A10)

 (A11)

 (A12)

 (A13)

-continued

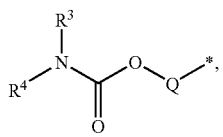 (A14)

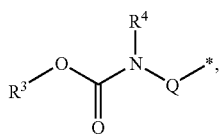 (A15)

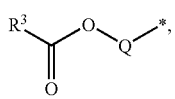 (A16)

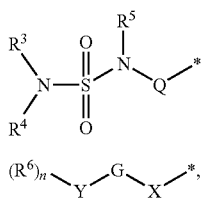 (A17)

and $(R^6)_n$—Y—G—X—* (A18)

wherein $R^3$, $R^4$ and $R^5$ which may be identical or different, denote hydrogen or a group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_4$-alkyl, $NR^7R^8$, $NR^7R^8$-$C_1$-$C_4$-alkyl, $C_1$-$C_4$-alkoxy, $C_1$-$C_4$-alkoxy-$C_1$-$C_4$-alkyl, $C_6$-$C_{14}$-aryl and $C_5$-$C_{10}$-heteroaryl, which may optionally be substituted by one or more of the groups, which may be identical or different, selected from among halogen, $NH_2$, OH, CN, $NR_9R_{10}$, —NH(CO)—$C_1$-$C_4$-alkyl and MeO, or in each case two of the substituents $R^3$, $R^4$ and $R^5$ together form a five-, six- or seven-membered ring, consisting of carbon atoms and optionally 1-2 heteroatoms, selected from among oxygen, sulphur and nitrogen; which may optionally be substituted by one or more of the groups, which may be identical or different, selected from among halogen, $NH_2$, OH, CN, $NR^9R^{10}$, —NH(CO)-$C_1$-$C_4$-alkyl and MeO;

$R^6$ which may be identical or different, denote hydrogen or a group, selected from among, $C_1$-$C_8$-alkyl, $C_2$-$C_6$-alkenyl $C_3$-$C_8$-cycloalkyl, $C_2$-$C_6$-haloalkyl, $C_6$-$C_{14}$-aryl, $C_5$-$C_{10}$-heteroaryl and $C_3$-$C_8$-heterocycloalkyl, which may optionally be substituted by one or more of the groups, which may be identical or different, selected from among, $NH_2$, NHMe, $NMe_2$, OH, OMe, CN, -$C_1$-$C_3$-alkyl-$C_6$-$C_{14}$-aryl, —NH-CO—NH—$C_1$-$C_3$-alkyl, $C_1$-$C_6$-alkyl and —(CO)O -$C_1$-$C_6$-alkyl or a group selected from among =O $NR^7R^8$, $OR^7$, —CO-$C_1$-$C_3$-alkyl -$NR^7R^8$, —O-$C_1$-$C_3$-alkyl -$NR^7R^8$, $CONR^7R^8$, $NR^7COR^8$, —CO-$C_1$-$C_3$-alkyl-$NR^7$(CO)$OR^8$, —O(CO)$NR^7R^8$, $NR^7$(CO)$NR^8R^9$, $NR^7$(CO)$OR^8$, (CO) $OR^7$, —O(CO)$R^7$, $COR^7$, (SO)$R^7$, $(SO_2)R^7$, $(SO_2)NR^7R^8$, $NR^7(SO_2)R_8$, $NR^7(SO_2)NR^8R^9$, CN and halogen;

$R^7$, $R^8$ and $R^9$ which may be identical or different, denote hydrogen or a group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_3$-alkyl, $C_6$-$C_{14}$-aryl, $C_1$-$C_4$-alkyl-$C_6$-$C_{14}$-aryl, $C_6$-$C_{14}$-aryl-$C_1$-$C_4$-alkyl, $C_3$-$C_8$-heterocycloalkyl, $C_1$-$C_5$-alkyl-$C_3$-$C_8$-heterocycloalkyl, $C_3$-$C_8$-heterocycloalkyl-$C_1$-$C_4$-alkyl, $C_1$-$C_4$-alkyl(CO)- and $C_1$-$C_4$-alkyl-O(CO), which may optionally be substituted by one or more of the groups, which may be identical or different, selected from among halogen, $NH_2$, OH, CN, OMe, NHMe, $NMe_2$, $C_1$-$C_6$-alkyl and (CO)O $C_1$-$C_6$-alkyl, or in each case two of the substituents $R^7$, $R^8$, $R^9$ together form a five-, six- or seven-membered ring, consisting of carbon atoms and optionally 1-2 heteroatoms, selected from among oxygen, sulphur and nitrogen; which may optionally be substituted by one or more of the groups, which may be identical or different, selected from among halogen, $NH_2$, OH, CN, OMe, NHMe, $NMe_2$, $C_1$-$C_6$-alkyl and (CO)O $C_1$-$C_6$-alkyl.

3. The compound according to claim 2, wherein $R^a$ and $R^1$ to $R^{12}$ may have the meaning specified and $R^b$ denotes hydrogen.

4. The compound according to claim 2, wherein $R^1$ to $R^{12}$ may have the meaning specified and $R^a$ denotes $C_6$-$C_{14}$-aryl or a $C_5$-$C_6$-heterocycloalkyl, wherein $R^a$ may optionally be substituted by one or more of the groups, which may be identical or different, selected from among $C_1$-$C_6$-alkyl, $C_2$-$C_6$-alkenyl, $C_2$-$C_6$-alkynyl, $C_3$-$C_8$-cycloalkyl, $C_{1\text{-}C6}$-haloalkyl, halogen, OH, $C_1$-$C_4$-alkoxy, CN, $NO_2$, $NR^{10}R^{11}$, $OR^{10}$, $COR^{10}$, $COOR^{10}$, $CONR^{10}R^{11}$, $NR^{10}COR^{11}$, $NR^{10}(CO)NR^{11}R^{12}$, $O(CO)NR^{10}R^{11}$, $NR^{10}(CO)OR^{11}$, $SO_2R^{10}$, SOR$^{10}$, $SO_2NR^{10}R^{11}$, $NR^{10}SO_2NR^{11}R^{12}$ and $NR^{10}SO_2R^{11}$, $R^b$ denotes hydrogen, $NH_2$ or OH, or a group selected from among $C_3$-$C_8$-cycloalkyl, $C_6$-$C_{14}$-aryl, $C_5$-$C_{10}$-heteroaryl, $C_6$-$C_{14}$-aryl-NH, $C_1$-$C_8$-alkyl, $C_2$-$C_8$-alkenyl, $C_2$-$C_8$-alkynyl and and $C_1$-$C_6$ haloalkyl which may optionally be substituted by one or more of the groups, which may be identical or different, selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, OMe, CN, $NH_2$, NHMe and and $NMe_2$.

5. The compound according to claim 4, wherein $R^a$ and $R^b$ may have the meaning specified and $R^1$ denotes hydrogen, $C_1$-$C_5$-alkyl or $C_3$-$C_8$-cycloalkyl, $R^2$ denotes hydrogen or an optionally substituted group selected from among $C_1$-$C_5$ alkyl, $C_6$-$C_{14}$-alkyl-$C_1$-$C_5$-alkyl, $C_3$-$C_8$-cycloalkyl-$C_1$-$C_4$-alkyl, $C_5$-$C_{10}$-heteroaryl-$C_1$-$C_6$-alkyl, $C_3$-$C_8$-heterocycloalkyl and $C_3$-$C_8$-heterocycloalkyl-$C_1$-$C_6$-alkyl, or $R^1$ and $R^2$ together form an optionally substituted five- or six-membered ring consisting of carbon atoms and optionally 1 to 2 nitrogen atoms, or $R^1$ and $R^2$ together form an optionally substituted nine- to thirteen-membered spirocyclic ring, or $R^1$ and $R^2$ which may be identical or different, denote a group selected from among general formulae (A2), (A3), (A8), (A 10), (A11) and (A 12), wherein X denotes a bond or an optionally substituted $C_1$-$C_3$-alkylene;

X together with $R^1$, $R^3$ $R^4$ or may form a $C_1$-$C_7$-alkylene bridge;

Q denotes an optionally substituted $C_1$-$C_3$-alkylene, or

Q together with $R^1$, $R^3$ or $R^4$ or may form a $C_1$-$C_7$-alkylene bridge;

$R^3$, $R^4$ and $R^5$ which may be identical or different, denote hydrogen or an optionally substituted group selected from among $C_1$-$C_4$-alkyl, $C_1$-$C_4$-alkoxy, $C_3$-$C_6$-cycloalkyl and $C_5$-$C^{10}$-heteroaryl, or in each case two of the substituents $R^3$, $R^4$ and $R^5$ together form an optionally substituted five- or six -membered ring, consisting of carbon atoms and optionally 1-2 heteroatoms, selected from among oxygen and nitrogen.

6. The compound according to claim 4,
wherein
$R^a$ and $R^b$ may have the meaning specified and
$R^1$ denotes H, Me
$R^2$ denotes hydrogen or a group of general formulae (A 18),
wherein X denotes a bond or an optionally substituted group selected from among $C_1$-$C_7$-alkylene, $C_3$-$C_7$-alkenylene and $C_3$-$C_7$-alkynylene;

Y denotes a bond, methylene or ethylene;

X and Y may be linked to the same or different atoms of G, and

G denotes a saturated, partially saturated or unsaturated ring system consisting of 3-10 C atoms, wherein optionally up to 6 C atoms are replaced by heteroatoms selected from among nitrogen, oxygen and sulphur;

$R^6$ which may be identical or different, denotes hydrogen or an optionally substituted group selected from among $C_1$-$C_4$-alkyl, $C_2$-$C_6$-alkenyl, $C_3$-$C_6$-cycloalkyl, $C_6$-$C_{14}$-aryl, $C_5$-$C_6$-heterocycloalkyl; and $C_5$-$C_6$-heteroaryl or a group selected from among =O, $NR^7R^8$, $OR^7$, —O—$C_1$-$C_3$-alkyl -$NR^7R^8$, $CONR^7R^8$, $CO$-$C_1C_3$-alkyl-$NR^7R^8$, $NR^7COR^8$, $NR^7(CO)OR^8$, —$CO$—$C_1$-$C_3$-alkyl -$NR^7(CO)OR^8$, $NR^7(CO)NR^8R^9$, $NR^7(CO)OR^8$, $(CO)OR^7$, $COR^7$, $(SO_2)R^7$, —$C_1$-$C_3$-alkyl-$C_6$-$C_{14}$-aryl, —$NH$-$CO$-$NH$-$C_1$-$C_3$-alkyl and CN;

n denotes 1 or 2;

$R^7$, $R^8$, and $R^9$ which may be identical or different, denote hydrogen or an optionally substituted group selected from among $C_1$-$C_5$-alkyl, $C_1$-$C_4$-alkyl-$C_6$-$C_{14}$-aryl, $C_3$-$C_6$-heterocycloalkyl and $C_1$-$C_5$-alkyl-$C_3$-$C_8$-heterocycloalkyl, or in each case two of the substituents $R^7$, $R^8$, $R^9$ together form an optionally substituted five- or six-membered ring, consisting of carbon atoms and optionally 1-2 heteroatoms, selected from among oxygen and nitrogen.

7. A pharmaceutical composition comprising a pharmaceutically effective amount of a compound according to claim 1.

8. The pharmaceutical composition according to claim 7 for inhalative administration.

9. The pharmaceutical composition according to claim 7 for oral administration.

10. The pharmaceutical composition according to claim 7, comprising as a further active substance, one or more compounds which are selected from the categories of the betamimetics, anticholinergics, corticosteroids, other PDE4-inhibitors, LTD4-antagonists, EGFR-inhibitors, dopamine agonists, Hi-antihistamines, PAF-antagonists and PI3-kinase inhibitors or double or triple combinations thereof.

11. A compound selected from:

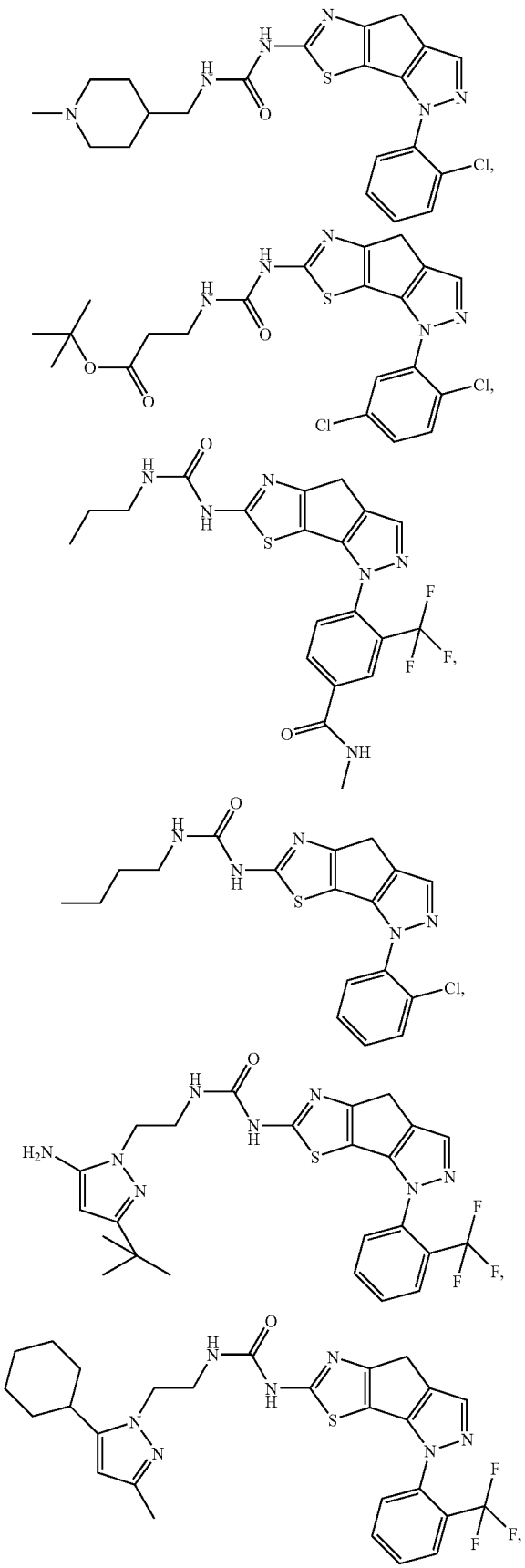

-continued
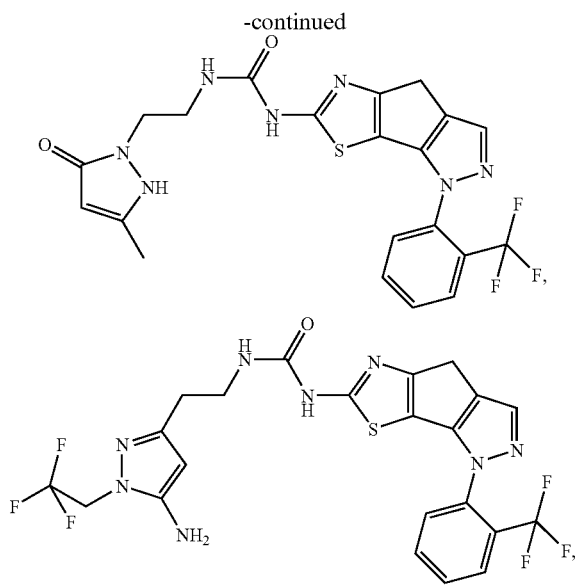
-continued
and
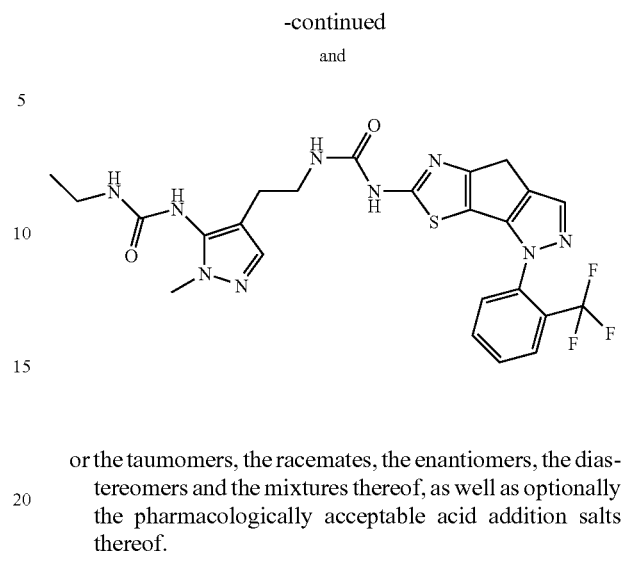
or the taumomers, the racemates, the enantiomers, the diastereomers and the mixtures thereof, as well as optionally the pharmacologically acceptable acid addition salts thereof.
* * * * *